(12) United States Patent
Bach et al.

(10) Patent No.: US 8,097,585 B2
(45) Date of Patent: Jan. 17, 2012

(54) METHODS OF TREATING INFLAMMATION BY ADMINISTRATION OF HEME OXYGENASE-1 AND PRODUCTS OF HEME DEGRADATION

(75) Inventors: Fritz H. Bach, Manchester-by-the-sea, MA (US); Pascal O. Berberat, Heidelberg (DE); Simon C. Robson, Weston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 861 days.

(21) Appl. No.: 10/511,612

(22) PCT Filed: Apr. 15, 2003

(86) PCT No.: PCT/US03/11411
§ 371 (c)(1),
(2), (4) Date: Aug. 5, 2005

(87) PCT Pub. No.: WO03/088748
PCT Pub. Date: Oct. 30, 2003

(65) Prior Publication Data
US 2006/0003922 A1    Jan. 5, 2006

Related U.S. Application Data

(60) Provisional application No. 60/372,762, filed on Apr. 15, 2002.

(51) Int. Cl.
*A61K 38/16* (2006.01)
(52) U.S. Cl. .............. 514/6; 514/2; 514/12; 435/7.1
(58) Field of Classification Search ............... None
See application file for complete search history.

(56) References Cited

U.S. PATENT DOCUMENTS

| | | | |
|---|---|---|---|
| 4,053,590 A | 10/1977 | Bonsen et al. | |
| 4,264,739 A | 4/1981 | Grabner et al. | |
| 4,923,817 A | 5/1990 | Mundt et al. | |
| 4,979,939 A | 12/1990 | Shiber | |
| 5,084,380 A | 1/1992 | Carney | |
| 5,180,366 A | 1/1993 | Woods | |
| 5,240,912 A | 8/1993 | Todaro | |
| 5,293,875 A | 3/1994 | Stone | |
| 5,449,665 A | 9/1995 | Sollevi et al. | |
| 5,476,764 A | 12/1995 | Bitensky | |
| 5,498,421 A | 3/1996 | Grinstaff et al. | |
| 5,588,960 A | 12/1996 | Edwards et al. | |
| 5,632,162 A | 5/1997 | Billy et al. | |
| 5,664,563 A | 9/1997 | Schroeder et al. | |
| 5,709,874 A | 1/1998 | Hanson et al. | |
| 5,731,326 A | 3/1998 | Hart et al. | |
| 5,756,492 A | 5/1998 | Buelow et al. | |
| 5,763,431 A | 6/1998 | Jackson | |
| 5,792,325 A | 8/1998 | Richardson, Jr. | |
| 5,882,674 A | 3/1999 | Herrmann et al. | |
| 5,885,621 A | 3/1999 | Head et al. | |
| 5,914,316 A | 6/1999 | Brown et al. | |
| 5,985,307 A | 11/1999 | Hanson et al. | |
| 6,066,333 A | 5/2000 | Willis et al. | |
| 6,069,132 A | 5/2000 | Revanker | |
| 6,203,991 B1 | 3/2001 | Nabel et al. | |
| 6,251,418 B1 | 6/2001 | Ahern et al. | |
| 6,313,144 B1 | 11/2001 | McCullough et al. | |
| 6,316,403 B1 | 11/2001 | Pinsky et al. | |
| 6,406,716 B2 | 6/2002 | Caruso et al. | |
| 6,436,365 B2 | 8/2002 | Dinkelborg et al. | |
| 6,450,989 B2 | 9/2002 | Dubrul et al. | |
| 6,508,784 B1 | 1/2003 | Shu | |
| 6,508,787 B2 | 1/2003 | Widmann et al. | |
| 7,045,140 B2 | 5/2006 | Motterlini et al. | |
| 7,238,469 B2 * | 7/2007 | Bach et al. ................ 435/1.1 |
| 7,364,757 B2 * | 4/2008 | Otterbein et al. ............ 424/699 |
| 2002/0155166 A1 | 10/2002 | Choi et al. | |
| 2002/0169201 A1 | 11/2002 | Falchuk | |
| 2003/0009127 A1 | 1/2003 | Trescony et al. | |
| 2003/0039638 A1 | 2/2003 | Bach et al. | |
| 2003/0064114 A1 | 4/2003 | Motterlini et al. | |
| 2003/0068387 A1 | 4/2003 | Buelow et al. | |
| 2003/0219496 A1 | 11/2003 | Otterbein et al. | |
| 2003/0219497 A1 | 11/2003 | Otterbein et al. | |
| 2004/0005367 A1 | 1/2004 | Otterbein et al. | |
| 2004/0052866 A1 | 3/2004 | Otterbein et al. | |
| 2004/0067261 A1 | 4/2004 | Haas et al. | |
| 2004/0131703 A1 | 7/2004 | Bach et al. | |
| 2004/0197271 A1 | 10/2004 | Kunka et al. | |
| 2004/0228930 A1 | 11/2004 | Billiar et al. | |
| 2004/0258772 A1 | 12/2004 | Otterbein et al. | |
| 2005/0048133 A1 | 3/2005 | Pinsky et al. | |
| 2005/0215468 A1 | 9/2005 | Bar-Or et al. | |
| 2005/0250688 A1 | 11/2005 | Pinsky et al. | |
| 2006/0003922 A1 | 1/2006 | Bach et al. | |
| 2007/0202083 A1 | 8/2007 | Bach et al. | |
| 2008/0167609 A1 | 7/2008 | Otterbein et al. | |
| 2008/0171021 A1 | 7/2008 | Bach et al. | |

FOREIGN PATENT DOCUMENTS

FR          2816212 A1    5/2002

(Continued)

OTHER PUBLICATIONS

Ryter et al., Am. J. Physiol. Heart Circ. Physiol., vol. 279, pp. H2889-H2897, 2000.*

Abidin et al., "The Combined Effect of Carbon Monoxide and Normobarid Hyperoxia on Animals," *Kosmicheskaya Biologiya I Aviakosmicheskaya Meditsina*, vol. 6:63-67 (1978).

Agarwal, Anupam et al., "Renal Response to Tissue Injury: Lessons from Heme Oxygenase-1 Gene Ablation and Expression," *J. Am. Soc. Nephrol.*, vol. 11:965-973 (2000).

(Continued)

*Primary Examiner* — Hope A Robinson

(74) *Attorney, Agent, or Firm* — Nelson Mullins Riley & Scarborough LLP; Megan E. Williams

(57) ABSTRACT

The present invention relates to the treatment of disorders using heme oxygenase-1 and heme degradation products.

31 Claims, 27 Drawing Sheets

FOREIGN PATENT DOCUMENTS

| | | |
|---|---|---|
| JP | 53-81611 | 7/1978 |
| JP | 56-79957 | 6/1981 |
| JP | 10-506388 | 6/1998 |
| WO | WO-94/22482 A1 | 10/1994 |
| WO | WO-95/35105 A1 | 12/1995 |
| WO | WO-98/08523 A1 | 3/1998 |
| WO | WO-98/13058 A1 | 4/1998 |
| WO | WO-99/47512 A1 | 9/1999 |
| WO | WO-99/49880 A1 | 10/1999 |
| WO | WO-00/36113 | 6/2000 |
| WO | WO-00/61166 | 10/2000 |
| WO | WO-02/09731 A1 | 2/2002 |
| WO | WO-02/092075 A2 | 11/2002 |
| WO | WO-03/000114 A2 | 1/2003 |
| WO | WO-2004/004817 A1 | 1/2004 |

OTHER PUBLICATIONS

Akagi, Reiko et al., "Fundamental Role of Heme Oxygenase in the Protection Against Ischemic Acute Renal Failure," *Jpn. J. Pharmacol.*, vol. 88:127-132 (2002).

Allred, Elizabeth N. et al., "Effects of Carbon Monoxide on Myocardial Ischemia," *Environmental Health Perspectives*, vol. 91:89-132 (1991).

American Cancer Society, "Colorectal Cancer Treatment: An Overview," retrieved online at cancer.org/docroot/NWS/content/NW_1_1x_Colorectal_cancer_treatment (2000).

American Thoracic Society, "Single-breath Carbon Monoxide Diffusing Capacity (Transfer Factor)," *American Journal of Respiratory and Critical Care Medicine*, vol. 152:2185-2198 (1995).

American Thoracic Society, "Single Breath Carbon Monoxide Diffusing Capacity (Transfer Factor), Recommendations for a Standard Technique," *American Journal of Respiratory and Critical Care Medicine*, vol. 136 (5):1299-1307 (1987).

Appel, James Z., III et al., "The Pig as a Source of Cardiac Xenografts," *J. Card. Surg.*, vol. 16:345-356 (2001).

Arcasoy, Murat O. et al., "Erythropoietin (EPO) Stimulates Angiogenesis in Vivo and Promotes Wound Healing," *Blood*, vol. 98:822A-823A (2001).

Arita, Seiji et al., "Prevention of Primary Islet Isograft Nonfunction in Mice with Pravastatin," *Transplantation*, vol. 65(11):1429-1433 1998.

Arnush, Marc et al., "IL-1 Produced and Released Endogenously within Human Islets Inhibits βCell Function," *J. Clin. Invest.*, vol. 102(3):516-526 (1998).

Avihingsanon, Yingyos et al., "Expression of Protective Genes in Human Renal Allografts: A Regulatory Response to Injury Associated with Graft Rejection," *Transplantation*, vol. 73(7):1079-1085 (2002).

Bach, Fritz H. et al., "Accommodation of vascularized xenografts: Expression of 'protective genes' by donor endothelial cells in a host Th2 cytokine environment," *Nature Medicine*, vol. 3(2):196-204 (1997).

Bach, Fritz H., "Heme oxygenase-1 as a protective gene," *Wien Klin Wochenschr.*, vol. 114(Suppl. 4):1-3 (2002).

Bairn, Donald S. et al., "Treatment of Coronary Stenoses and Occlusions with Coronary Angioplasty," *Harrison's Principles of Internal Medicine*, 13th Edition, McGraw-Hill, Inc., Kurt J. Isselbacher Eds., vol. 1:986-987 (1994).

Bathoom, E. et al., "Anti-inflammatory effects of inhaled carbon monoxide in patients with COPD: A pilot study," *Eur. Respir. J.*, vol. 30:1131-1137 (2007).

Bathoom, E. et al., "Effects of low dose inhaled carbon monoxide in patients with COPD," Thematic Poster Session, 349. Recent advances in the treatment of COPD and acute lung injury, Hall B2-9—12:50-14:40, pp. 660s-663s (2006).

Bentley, Michael J. et al., "Successful Cardiac Transplantation With Methanol or Carbon Monoxide-Poisoned Donors," *Ann. Thorac. Surg.*, vol. 71:1194-1197 (2001).

Berney, Thierry et al., "Islet cell transplantation: the future?" *Langenbeck's Arch. Surg.*, vol. 385:373-378 (2000).

Billiar, Timothy R., "The diverging roles of carbon monoxide and nitric oxide in resuscitated hemorrhagic shock," *Critical Care Medicine*, vol. 27(12):2842-2843 (1999).

Bracho, G.E., II, et al., "Carbon Monoxide Protects against Organ Injury in Hemorrhagic Shock/Resuscitation," *Journal of Surgical Research*, vol. 107:267-338 (2002).

Brouard, Sophie et al., "Carbon Monoxide generated by Heme Oxygenase-1 (HO-1) suppresses endothelial cell apoptosis via activation of the p38 mitogen activated protein kinase (MAPK) pathway," *Acta Haematologica*, vol. 103(Suppl. 1):64, No. 254 (2000).

Brouard, Sophie et al., "Carbon Monoxide Generated by Heme Oxygenase 1 Suppresses Endothelial Cell Apoptosis," *J. Exp. Med.*, vol. 192(7):1015-1025 (2000).

Brouard, Sophie et al., "Heme Oxygenase-1-derived Carbon Monoxide Requires the Activation of Transcription Factor NF-κB to Protect Endothelial Cells from Tumor Necrosis Factor-α-mediated Apoptosis," *The Journal of Biological Chemistry*, vol. 277(20):17950-17961 (2002).

Brouard, S. et al., "Molecular mechanism underlying the anti-apoptotic effect of Heme oxygenase-1 derived carbon monoxide," *Xenotransplantation*, vol. 8(Suppl. 1):22 2001).

Brown, S.D. et al., "In vivo binding of carbon monoxide to cytochrome c oxidase in rat brain," *Journal of Applied Physiology*, vol. 68(2):604-610 (1990).

Calabrese, F. et al., "Carbon Monoxide (CO) Prevents Apoptotic Events Related to Ischemia/Reperfusion (IR) Injury in an hDAF Pig-to-Primate Xenotransplantation Model," *Xenotransplantation*, vol. 10:488 (2003).

Campbell, J. Argyll, "Cancer of Skin and Increase in Incidence of Primary Tumours of Lung in Mice Exposed to Dust Obtained from Tarred Roads," *The British Journal of Experimental Pathology*, vol. 15(5):287-294 (1934).

Campbell, J. Argyll, "Living at Very High Altitudes and Maintenance of Normal Health," *The Lancet*, vol. 1:370-373 (1930).

Campbell, J. Argyll, "The Effect of Carbon Monoxide and Other Agetns Upon the Rate of Tumour Growth," *J. Pathology & Bacteriology*, vol. 35:379-394 (1932).

Cantrell, James M. et al., "Low-dose Carbon. Monoxide Does Not Reduce Vasoconstriction in Isolated Rat Lungs," *Experimental Lung Research*, vol. 22:21-32 (1996).

Caplan, Michael S. et al., "Role of Asphyxia and Feeding in a Neonatal Rat Model of Necrotizing Enterocolitis," *Pediatric Pathology*, vol. 14:1017-1028 I1994).

Cardell, Lars-Olaf et al., "Bronchodilation in vivo by carbon monoxide, a cyclic GMP related messenger," *British Journal of Pharmacology*, vol. 124:1065-1068 (1998).

Carlsson, Per-Ola et al., "Measurements of Oxygen Tension in Native and Transplanted Rat Pancreatic Islets," *Diabetes*, vol. 47:1027-1032 (1998).

Carraway, M.S. et al., "Induction of ferritin and heme oxygenase-1 by endotoxin in the lung," *Am. J. Physiol. Lung Cell Mol. Physiol.*, vol. 275:L583-L592 (1998).

Cecil Textbook of Medicine (21st Ed.) vol. 1:273-279, 357-372, 387-419, 425-427, 436-448, 466-475, 507-512, 1060-1074 (2000).

Cecil Textbook of Medicine (21st Ed.) vol. 2:1492-1499, 2042-2047, 2079-2081 (2000).

Chapman, Jeffrey T. et al., "Carbon monoxide attenuates aeroallergen-induced inflammation in mice," *Am. J. Physiol. Lung Cell. Mol. Physiol.*, vol. 281:L209-L216 (2001).

Chapman, Jeff T. et al., "Exogenous Carbon Monoxide Attenuates Aeroallergen-induced Eosinophilic Inflammation in Mice," *American Journal of Respiratory and Critical Care Medicine*, vol. 159(3):A218 (1999).

Chapman, Jeffrey T. et al., "Exhaled Monoxides as a Pulmonary Function Test," *Clinics in Chest Medicine*, vol. 22(4):817-836 (2001).

Chen, Yen-Chou et al., "Nitric Oxide and Prostaglandin $E_2$ Participate in Lipopolysaccharide/Interferon-γ-Induced Heme Oxygenase 1 and Prevent RAW264.7 Macrophages from UV-Irradiation-Induced Cell Death," *Journal of Cellular Biochemistry*, vol. 86:331-339 (2002).

Chin, Beek Yoke et al., "Transcriptional regulation of the HO-1 gene in cultured macrophages exposed to model airborne particulate matter," *Am. J. Physiol. Lung Cell. Mol. Physiol.*, vol. 284:L473-L480 (2003).

Choi, Augustine M.K. et al., "Emerging Role of Carbon Monoxide in Physiologic and Pathophysiologic States," *Antioxidants & Redox Signaling*, vol. 4(2):227-228 (2002).

Choi, Augustine M.K. et al., "Heme Oxygenase-1: Function, Regulation, and Implication of a Novel Stress-inducible Protein in Oxidant-induced Lung Injury," *Am. J. Respir. Cell Mol. Biol.*, vol. 15:9-19 (1996).

Choi, Augustine M.K., "Heme Oxygenase-1 Protects the Heart," *Circulation Research*, vol. 89:105-107 (2001).

Choi, Augustine M.K. et al., "'Therapeutic' Carbon Monoxide May be a Reality Soon," *American Journal of Respiratory and Critical Care Medicine*, vol. 171:1318-1319 (2005).

Christodoulides, Nick et al., "Vascular Smooth Muscle Cell Home Oxygenases Generate Guanylyl Cyclase-Stimulatory Carbon Monoxide," *Circulation*, vol. 91:2306-2309 (1995).

Clayton, Carolyn E. et al., "Inhaled carbon monoxide and hyperoxic lung injury in rats," *Am. J. Physiol. Cell Mol. Physiol.*, vol. 281:L949-L957 (2001).

ClinicalTrials.gov, "Carbon Monoxide to Prevent Lung Inflammation," retrieved online at clinicaltrials.gov/ct2/show?spons=%22National+Institutes+of+Health+Clinical+Center+(CC)%22&spons_ex=Y&rank=8 (2007).

ClinicalTrials.gov, "Modification of Chronic Inflammation by Inhaled Carbon Monoxide in Patients With Stable Chronic Obstructive Pulmonary Disease (COPD)," retrieved online at clinicaltrials.gov/ct2/show/NCT00122694?term=neut ophils&rank=74 (2006).

Corbett, John A. et al:, "Nitric oxide mediates cytokine-induced inhibition of insulin secretion by human islets-of Langerhans," *Proc. Natl. Acad. Sci. USA*, vol. 90:1731-1735 (1993).

Cozzi, E. et al., "Donor Preconditioning with Carbon Monoxide (CO) in Pig-to-Primate Xenotransplantation," *Xenotransplantation*, vol. 10:528 (2003).

Crapo, Robert O. et al., "Single-Breath Carbon Monoxide Diffusing Capacity," *Clinics in Chest Medicine*, vol. 22(4):637-649 (2001).

Czlonkowska, Anna et al., "Immune processes in the pathogenesis of Parkinson's disease—a potential role for microglia and nitric oxide," *Med. Sci. Monit.*, vol. 8(8):RA165-177 (2002).

Davidson, Jeffrey M. et al., "Inflammatory Modulation and Wound Repair," *The Journal of Investigative Dermatology*, pp. xi-xii (2003).

Deng, Xiaoying et al., "Carbon Monoxide Potentiates Cerulein-Induced Pancreatitis in Chronic Alcohol-Fed Rats," *Gastroenterology*, vol. 124(4):A618-A619 (2003).

Dioum, Elhadji M. et al., "NPAS2: A Gas-Responsive Transcription Factor," *Science*, vol. 298:2385-2387 (2002).

Dolinay, T. et al., "Can Inhalation Carbon Monoxide be Utilized as a Therapeutic Modality in Human Diseases?" *Breath Analysis for Clinical Diagnosis and Therapeutic Monitoring*, World Scientific, Anton Amann, Ed., pp. 203-236 (2005).

Dolinay, Tarnas et al., "Inhaled Carbon Monoxide Confers Antiinflammatory Effects Against Ventilator-induced Lung Injury," *Am. J. Respir. Crit. Care Med.*, vol. 170:613-620 (2004).

Donnelly, Louise E. et al., "Expression of Heme Oxygenase in Human Airway Epithelial Cells," *Am. J. Respir. Cell Mol. Biol.*, vol. 24:295-303 (2001).

Downard, Patrick J. et al., "Heme Oxygenase-Dependent Carbon Monoxide Production Is a Hepatic Adaptive Response to Sepsis," *Journal of Surgical Research*, vol. 71:7-12 (1997).

Dyck, E. Danielle et al., "Carbon Monoxide (CO) Attenuates Lipopolysaccharide (LPS)-Induced Cytokine Expression of IL-6," *Acta Haematologica*, vol. 103(Suppl. 1):64 (2000).

Ellenhorn, Matthew J. et al., "Carbon Monoxide," *Medical Toxicology, Diagnosis and Treatment of Human Poisoning*, Elsevier, Chpt. 34, pp. 820-829 (1988).

Farrugia, Gianrico et al., "Heme Oxygenase, Carbon Monoxide, and Interstitial Cells of Cajal," *Microsc. Res. Tech.*, vol. 47:321-324 (1999).

Favory, Raphaël et al., "Myocardial Dysfunction and Potential Cardiac Hypoxia in Rats Induced by Carbon Monoxide Inhalation," *Am. J. Respir. Crit. Care Med.*, vol. 174:320-325 (2006).

Friebe, Andreas et al., "YC-1 Potentiates Nitric Oxide- and Carbon Monoxide-Induced Cyclic GMP Effects in Human Platelets," *Molecular Pharmacology*, vol. 54:962-967 (1998).

Fujii, Hiromi et al., "Protective role of heme oxygenase-1 in the intestinal tissue injury in an experimental model of sepsis," *Crit. Care Med.*, vol. 31(3):893-902 (2003).

Fujita, Tomoyuki et al., "Paradoxical rescue from ischemic lung injury by inhaled carbon monoxide drive by derepression of fibrinolysis," Nature Medicine, vol. 7(5):598-604 (2001).

Gaine, Sean P. et al., "Induction of Heme Oxygenase-1 with Hemoglobin Depresses Vasoreactivity in Rat Aorta," *Journal of Vascular Research*, vol. 36:114-119 (1999).

Goldberg, Mark A. et al., "Similarities between the Oxygen-sensing Mechanisms Regulating the Expression of Vascular Endothelial Growth Factor and Erythropoietin," *The Journal of Biological Chemistry*, vol. 269(6):4355-4359 (1994).

Goto, Jun et al., "Heme Oxygenase-1 Reduces Murine Monocrotaline-Induced Pulmonary Inflammatory Responses and Resultant,Right Ventricular Overload," *Antioxidants & Redox Signaling*, vol. 4(4):563-568 (2002).

Grau, Cai et al., "Effect of Carbon Monoxide Breathing on Hypoxia and Radiation Response in the SCCVII Tumor in Vivo," *Int. J. Radiation Oncology Biol. Phys.*, vol. 29(3):449-454 (1994).

Grau, Cai et al., "Influence of Carboxyhemoglobin Level on Tumor Growth, Blood Flow, and Radiation Response in an Experimental Model," *Int J. Radiation Oncology Biol. Phys.*, vol. 22:421-424 (1992).

Günther, Lukas et al., "Carbon Monoxide Protects Pancreatic β-Cells From Apoptosis and Improves Islet Function/Survival After Transplantation," *Diabetes*, vol. 51:994-999 (2002).

Guo, Xin et al., "Modulation of heme oxygenase in tissue injury adn its implication in protection against gastrointestinal diseases," *Life Sciences*, vol. 69:3113-3119 (2001).

Hantson, Philippe et al., "Organ Transplantation From Victims of Carbon Monoxide Poisoning," *Annals of Emergency Medicine*, vol. 27(5):673-674 (1996).

Harmey, Judith H. et al., "Vascular endothelial growth factor (VEGF), a survival factor for tumour cells: implications for anti-angiogenic therapy," *BioEssays*, vol. 24:280-283 (2002).

Hartsfield, Cynthia L., "Cross Talk Between Carbon Monoxide and Nitric Acid," *Antioxidants & Redox Signaling*, vol. 4(2):301-307 (2002).

Hartsfield, Cynthia L. et al., "Differential signaling pathways of HO-1 gene expression in pulmonary and systemic vascular cells," *Am. J. Physiol.*, vol. 277(6 pt. 1):L1133-L1141 (1999).

Hartsfield, Cynthia L. et al., "Mitogen activated protein kinase (MAPK) is modulated by both endogenous and exogenous carbon monoxide," *The FASEB Journal*, vol. 12(4):A187 (1998).

Hartsfield, Cynthia L. et al., "Regulation of heme oxygenase-1 gene expression in vascular smooth muscle cells by nitric oxide;" *Am. J. Physiol. Lung Cell Mol. Physiol.*, vol. 273:L980-L988 (1997).

Hashiba, T. et al., "Adenovirus-mediated transfer of heme oxygenase-1 cDNA attenuates severe lung injury induced by the influenza virus in mice," *Gene Therapy*, vol. 8:1499-1507 (2001).

Hayes, Harry Jr., "A Review of Modern Concepts of Healing of Cutaneous Wounds," *J. Dermatol. Surg. Oncol.*, vol. 3:188-193 (1977).

Hébert, Marie-Josée et al., "Transplantation of Kidneys from a Donor with Carbon Monoxide Poisoning," *The New England Journal of Medicine*, vol. 326(23):1571 (1992).

Hisada, Takeshi et al., "Involvement of haemoxygenase-1 in oxone-induced airway inflammation and hyperresponsiveness," *European Journal of Pharmacology*, vol. 399:229-234 (2000).

Horváth, I. et al., "'Haemoxygenase-1 induction and exhaled markers of oxidative stress in lung disease,' summary of the ERS Research Seminar in Budapest, Hungary, Sep. 1999," *European Respiratory Journal*, vol. 18:420-430 (2001).

Huizinga, Jan D., "Physiology and Pathophysiology of the Interstitial Cell of Cajal: From Bench to Bedside II. Gastric motility: lessons from mutant mice on slow waves and innervation," *Am. J. Physiol. Gastrointest. Liver Physiol.*, vol. 281:G1129-G1134 (2001).

Iberer, Florian et al., "Cardiac Allograft Harvesting after Carbon Monoxide Poisoning. Report on a Successful Orthotopic Heart Transplantation," *J. Heart Lung Transplant*, vol. 12:499-500 (1993).

Johnson, J.I. et al., "Relationships between drug activity in NCI preclinical in vitro and in vivo models and early clinical trials," *British Journal of Cancer*, vol. 84(10):1424-1431 (2001).

Jośko, Jadwiga et al., "Vascular endothelial growth factor (VEGF) and its effect on angiogenesis," *Med. Sci. Monit.*, vol. 6(5):1047-1052 (2000).

Katori, Masamichi et al., "Heme Oxygenase-1 System in Organ Transplantation," *Transplantation*, vol. 74:905-912 (2002).

Kaufman, Dixon B. et al., "Differential Roles of Mac-1+Cells, and CD4+ and CD8+T Lymphocytes in Primary Nonfunction and Classic Rejection of Islet Allografts," *J. Exp. Med.*, vol. 172:291-302 (1990).

Koerner, Michael M. et al., "Extended Donor Criteria: Use of Cardiac Allografts after Carbon Monoxide Poisoning," *Transplantation*, vol. 63(9):1358-1360 (1997).

Kozma, Fruzsina et al., "Role of carbon monoxide in heme-induced vasodilation," *European Journal of Pharmacology*, vol. 323:R1-R2 (1997).

Krause, K. et al., "Recombinant human erythropoietin and VEGF have equal angiogenic potency: investigation in a novel in vitro assay of human vascular tissue," *European Heart Journal*, vol. 22:154 (2001).

Kyokane, Takanori et al., "Carbon Monoxide From Heme Carabolism Protects Against Hepatobiliary Dysfunction in Endotoxin-Treated Rat Liver," *Gastroenterology*, vol. 120:1227-1240 (2001).

Lacy, Paul E. et al., "Transplantation of Pancreatic Islets," *Ann. Rev. Immunol.*, vol. 2:183-198 (1984).

Lee et al., "Intestinal Motility and Absorption in Acute Carbon Monoxide Poisoning," *The Seoul Journal of Medicine*, vol. 15(2):95-105 (1974).

Lee, Patty J. et al., "Regulation of Heme Oxygenase-1 Expression in Vivo and in Vitro in Hyperoxic Lung Injury," *Am. J. Respir. Cell Mol. Biol.*, vol. 14:556-568 (1996).

Lefer, David J. et al., "A Comparison of Vascular Biological Actions of Carbon Monoxide and Nitric Oxide," *Methods and Findings in Experimental and Clinical Pharmacology*, vol. 15(9):617-622 (1993).

Leikin, Jerrold B. et al., "The Toxic Patient as a Potential Organ Donor," *Am. J. Emerg. Med.*, vol. 12:151-154 (1994).

Li, Li et al., "Protection against ozone-induced pulmonary inflammation and cell death by endotoxin pretreatment in mice: Role of HO-1," *Inhalation Toxicology*, vol. 12:1225-1238 (2000).

Libby, Peter et al., "Chronic Rejection," *Immunity*, vol. 14:387-397 (2001).

Liu, Yuxiang et al., "Carbon Monoxide and Nitric Oxide Suppress the Hypoxic Induction of Vascular Endothelial Growth Factor Gene via the 5' Enhancer," *The Journal of Biological Chemistry*, vol. 273(24):15257-15262 (1998).

Madhavan, Malathy et al., "Serum bilirubin distribution and its relation to cardiovascular risk in children and young adults," *Atherosclerosis*, vol. 131:107-113 (1997).

Mandrup-Poulsen, Thomas et al., "Human Tumor Necrosis Factor Potentiates Human Interleukin 1-Mediated Rat Pancreatic β-Cell Cytotoxicity," *The Journal of Immunology*, vol. 139(12):4077-4082 (1987).

Mansouri, Ali et al., "Alteration of Platelet Aggregation by Cigarette Smoke and Carbon Monoxide," *Thrombosis and Haemostasis*, vol. 48(3):286-288 (1982).

Mayer, Michael, "Association of Serum Bilirubin Concentration with Risk of Coronary Artery Disease," *Clinical Chemistry*, vol. 46(11):1723-1727 (2000).

Maxwell, L.C. et al., "Studies in Cancer Chemotherapy XI. The Effect of CO, HCN, and Pituitrin Upon Tumor Growth," *The Journal of Pharmacology and Experimental Therapeutics*, vol. 49:270-282 (1933).

Mayr, Florian B. et al., "Effects of Carbon Monoxide Inhalation during Experimental Endotoxernia in Humans," *Am. J. Respir. Crit. Care. Med.*, vol. 171:354-360 (2005).

Mazzola, S. et al., "Carbon monoxide pretreatment prevents respiratory derangement and ameliorates hyperacute endotoxic shock in pigs," *The FASEB Journal*, vol. 19(14):1-18 (2005).

Meilin, S. et al., "Effects of carbon monoxide on the brain may be mediated by nitric oxide," *J. Appl. Physiol.*, vol. 81(3):1078-1083 (1996).

Melo, Luis G. et al., "Gene Therapy Strategy for Long-Term Myocardial Protection Using Adeno-Associated Virus-Mediated Delivery of Heme Oxygenase Gene," *Circulation*, vol. 105:602-607 (2002).

Miller, Steven M. et al., "Heme Oxygenase 2 Is Present in Interstitial Cell Networks of the Mouse Small Intestine," *Gastroenterology*, vol. 114:239-244 (1998).

Minamino, Tohru et al., "Targeted expression of heme oxygenase-1 prevents the pulmonary inflammatory and vascular responses to hypoxia," *PNAS*, vol. 98(15):8798-8803 (2001).

Moore, Beverley A. et al., "Carbon Monoxide Suppresses the Development of Ileus Associated with Surgical Manipulation of the Small Intestine," *Gastroenterology*, vol. 122:A61-A62 (2002).

Moore, Beverley A. et al., "Inhaled Carbon Monoxide Suppresses the Development of Postoperative Ileus in the Murine Small Intestine," *Gastroenterology*, vol. 124:377-391 (2003).

Moore, Beverley A. et al., "Carbon Monoxide Protects against Intestinal Dysmotility Associated with Small Bowel Transplantation," *Gastroenterology*, vol. 122:A38 (2002).

Moore, Beverley A. et al., "Pre-treatment with Low Concentration of Carbon Monoxide (250 to 75 ppm) for 3 hr. prior to Laparotomy Protects Against Postoperative Ileus," *Gastroenterology*, vol. 124(4, Suppl. 1):A798 (2003).

Mori, Yoshio et al., "Evaluation of Hypothermic Heart Preservation with University of Wisconsin Solution in Heterotopically and Orthotopically Transplanted Canine Hearts," *J. Heart Lung Transplant*, vol. 13:688-695 (1994).

Morita, Shunsuke, "Cardiovascular disease and heme oxygenase carbon monoxide system," *Igaku no Ayumi* (Advances in Medicine), vol. 197(9):737-741 (2001).

Morse, Danielle et al., "Carbon Monoxide-dependent signaling," *Crit. Care Med.*, vol. 30(1):S12-S17 (2002).

Morse, Danielle et al., "Heme Oxygenase-1, From Bench to Bedside," *Am. J. Respir. Crit. Care Med.*, vol. 172:660-670 (2005).

Morse, Danielle et al., "Suppression of Inflammatory Cytokine Production by Carbon Monoxide Involves the JNK Pathway and AP-1," *The Journal of Biological Chemistry*, vol. 278(39):36993-36998 (2003).

Motterlini, Roberto et al., "Carbon Monoxide-Releasing Molecules, Characterization of Biochemical and Vascular Activities," *Circ. Res.*, vol. 90:e17-e24 (2002).

Myers, Robert P. et al., "Cirrhotic Cardiomyopathy and Liver Transplantation," *Liver Transplantation*, vol. 6(4, Suppl. 1):S44-S52 (2000).

Nachar, Raúl A. et al., "Low-Dose Inhaled Carbon Monoxide Reduces Pulmonary Vascular Resistance During Acute Hypoxemia in Adult Sheep," *High Altitude Medicine & Biology*, vol. 2(3):377-386 (2001).

Nagata, M. et al., "Destruction of Islet Isografts by Severe Nonspecific Inflammation," *Transplantation Proceedings*, vol. 22(2):855-856 (1990).

Nakagami, Tatsuyoshi et al., "A beneficial role of bile pigments as an endogenous tissue protector: Anti-complement effects of biliverdin and conjugated bilirubin," *Biochimica et Biophysica Acta*, vol. 1158:189-193 (1993).

Nakao, Atsunori et al., "A Single Intraperitoneal Dose of Carbon Monoxide-Saturated Ringer's Lactate Solution Ameliorates Postoperative Ileus in Mice," *The Journal of Pharmacology and Experimental Therapeutics*, vol. 319(3):1265-1275 (2006).

Nakao; A. et al., "Immunomodulatory effects of inhaled carbon monoxide on rat syngeneic small bowel graft motility," *Gut*, vol. 52:1278-1285 (2003).

Nakao, Atsunori et al., "Protective effect of carbon monoxide inhalation for cold-preserved small intestinal grafts," *Surgery*, vol. 134:285-292 (2003).

Nath, Karl A. et al., "Heme protein-induced chronic renal inflammation: Suppressive effect of induced heme oxygenase-1," *Kidney International*, vol. 59:106-117 (2001).

Ning, Wen et al., "TGF-$\beta_1$ stimulates HO-1 via the p38 mitogen-activated protein kinase in A549 pulmonary epithelial cells," *Am. J. Physiol. Lung Cell Mol. PHysiol.*, vol. 283:L1094-L1102 (2002).

Novotný, Ladislav et al., "Inverse Relationship Between Serum Bilirubin and Atherosclerosis in Men: A Meta-Analysis of Published Studies," *Exp. Biol. Med.*, vol. 228:566-571 (2003).

Omaye, Stanley T., "Metabolic modulation of carbon monoxide toxicity," *Toxicology*, vol. 180:139-150 (2002).

Otani, Kazuhiro et al., "Administration of Bacterial Lipopolysaccharide to Rats Induces Heme Oxygenase-1 and Formation of Antioxidant Bilirubin in the Intestinal Mucosa," *Digestive Diseases and Sciences*, vol. 45(12):2313-2319 (2000).

Otterbein, Leo E. et al., "Carbon Monoxide, a Gaseous Molecule with Anti-Inflammatory Properties," *Disease Markers in Exhaled Breath*, Claude Lenfant, Ed., Marcel Dekker, Inc., vol. 170, Chpt. 6, pp. 133-156 (2003).

Otterbein, Leo E. et al., "Carbon monoxide has anti-inflammatory effects involving the mitogen-activated protein kinase pathway," *Nature Medicine*, vol. 6(4):422-428 (2000).

Otterbein, Leo E. et al., "Carbon monoxide inhibits TNF$\alpha$-induced apoptosis and cell growth in mouse fibroblasts," *American Journal of Respiratory and Critical Cam Medicine*, vol. 159(3):A285 (1999).

Otterbein, Leo E., "Carbon Monoxide: Innovative Anti-inflammatory Properties of an Age-Old Gas Molecule," *Antioxidants & Redox Signaling*, vol. 4(2):309-319 (2002).

Otterbein, Leo E. et al., "Carbon Monoxide Mediates Anti-inflammatory Effects Via the P38 Mitogen Activated Protein Kinase Pathway," *Acta Haematologica*, vol. 103(Suppl. 1) No. 256 (2000).

Otterbein, Leo E. et al., "Carbon Monoxide Modulates Lipopolysaccharide (LPS)-Induced Inflammatory Responses in Vivo and in Vitro," *American Journal of Respiratory and Critical Care Medicine*, vol. 159(3):A481 (1999).

Otterbein, Leo E. et al., "Carbon Monoxide Protects Against Oxidant-Induced Lung Injury in Mice Via the p38 Mitogen Activated Protein Kinase Pathway," *Acta Haematologica*, vol. 103(Suppl. 1) No. 332 (2000).

Otterbein, Leo E. et al., "Carbon monoxide provides protection against hyperoxic lung injury," *Am. J. Physiol. Lung Cell. Mol. Physiol.*, vol. 276:L688-L694 (1999).

Otterbein, Leo E. et al., "Carbon Monoxide Provides Protection Against Hyperoxic Lung Injury in Rats," *American Journal of Respiratory and Critical Care Medicine*, vol. 159(3):A218 (1999).

Otterbein, Leo E. et al., "Carbon monoxide suppresses arteriosclerotic lesions associated with chronic graft rejection and with balloon injury," *Nature Medicine*, vol. 9(2):183-190 (2003).

Otterbein, Leo E. et al., "Exogenous administration of heme oxygenase-1 by gene transfer provides protection against hyperoxia-induced lung injury," *The Journal of Clinical Investigation*, vol. 103(7):1047-1054 (1999).

Otterbein, Leo E. et al., "Heme oxygenase-1: unleashing the protective properties of heme," *Trends in Immunology*, vol. 24(8):449-455 (2003).

Otterbein, Leo E. et al., "Heme oxygenase: colors of defense against cellular stress," *Am. J. Physiol. Lung Cell. Mol. Physiol.*, vol. 279:L1029-L1037 (2000).

Otterbein, Leo et al., "Hemoglobin Provides Protection against Lethal Endotoxemia in Rats: The Role of Heme Oxygenase-1," *Am. J. Respir. Cell Mol. Biol.*, vol. 13:595-601 (1995).

Otterbein, Leo et al., "Mechanism of hemoglobin-induced protection against endotoxemia in rats: a ferritin-independent pathway," *Am. J. Physiol. Lung Cell. Mol. Physiol.*, vol. 272:L268-L275 (1997).

Otterbein, Leo E. et al., "Protective Effects of Heme Oxygenase-1 in Acute Lung Injury," *Chest*, vol. 116:61S-63S (1999).

Otterbein, Leo E. et al., "Carbon monoxide at low concentrations induces growth arrest and modulates tumor growth in mice," *Exp. Biol. Med.*, vol. 228(5):633 (2003).

Otterbein, Leo E., "Anti-Inflammatory Effects of Carbon Monoxide in the Lung," CRISP Grant No. 5R01HL071797-05 (2003).

Otterbein, Leo E., "Carbon Monoxide to Prevent Circulatory Collapse," CRISP Grant No. 1R01HL076167-01 (2004).

Otterbein, Leo E., "Carbon Monoxide to Prevent Circulatory Collapse," CRISP Grant No. 7R01HL076167-02 (2004).

Otterbein, Leo E., "Anti-Inflammatory Effects of Carbon Monoxide in the Lung," CRSIP Grant No. 5R01HL071797-04 (2005).

Otterbein, Leo E., "Anti-Inflammatory Effects of Carbon Monoxide in the Lung," CRSIP Grant No. 7R01HL071797-03 (2004).

Otterbein, Leo E., "Anti-Inflammatory Effects of Carbon Monoxide in the Lung," CRISP Grant No. 5R01HL071797-02 (2004).

Otterbein, Leo E., "Carbon Monoxide to Prevent Circulatory Collapse," CRSIP Grant No. 5R01HL076167-04 (2006).

Otterbein, Leo E., "Anti-Inflammatory Effects of Carbon Monoxide in the Lung," CRISP Grant No. 1R01HL071797-01A1 (2003).

Otterbein, Leo E., "Anti-Inflammatory Effects of Carbon Monoxide in the Lung," CRISP Grant No. 5R01HL071797-05 (2006).

Otterbein, Leo E., "Carbon Monoxide to Prevent Circulatory Collapse," CRSIP Grant No. 5R01HL076167-03 (2005).

Otterbein, Leo E., "Carbon Monoxide to Prevent Circulatory Collapse," CRSIP Grant No. 5R01HL076167-05 (2007).

Pannen, Benedikt H.J. et al., "Protective Role of Endogenous Carbon Monoxide in Hepatic Microcirculatory Dysfunction after Hemorrhagic Shock in Rats," *J. Clin. Invest.*, vol. 102(6):1220-1228 (1998).

Paredi, P. et al., "Increased carbon monoxide in exhaled air of cystic fibrosis patients," *American Journal of Respiratory and Critical Care Medicine*, vol. 159(3):A218 (1999).

Peek, Giles J. et al., "Extracorporeal Membrane Oxygenation for Adult Respiratory Failure," *Chest*, vol. 112(3):759-764 (1997).

Petrache, Irina et al., "Heme oxygenase-1 inhibits TNF-$\alpha$-induced apoptosis in cultured fibroblasts," *Am. J. Physiol. Lung Cell. Mol. Physiol.*, vol. 278:L312-L319 (2000).

Piantadosi, C.A. et al., "Production of Hydroxyl Radical in the Hippocampus After CO Hypoxia or Hypoxic Hypoxia in the Rat," *Free Radical Biology & Medicine*, vol. 22(4):725-732 (1997).

Pileggi, Antonello et al., "Heme Oxygenase-1 Induction in Islet Cells Results in Protection From Apoptosis and Improved in Vivo Function After Transplantation," *Diabetes*, vol. 50:1983-1991 (2001).

Poss, Kenneth D. et al., "Heme oxygenase 1 is required for mammalian iron reutilization," *Proc. Natl. Acad. Sci. USA*, vol. 94:10919-10924 (1997).

Poss, Kenneth D. et al., "Reduced stress defense in heme oxygenase 1-deficient cells," *Proc. Natl. Acad. Sci. USA*, vol. 94:10925-10930 (1997).

Potter, Huntington et al., "The inflammation-induced pathological chaperones ACT and apo-E are necessary catalysts of Alzheimer amyloid formation," *Neurobiology*, vol. 22:923-930 (2001).

Pozzoli, G. et al., "Carbon Monoxide as a Novel Neuroendocrine Modulator: Inhibition of Stimulated Corticotropin-Releasing Hormone Release from Acute Rat Hypothalamic Explants," *Endocrinology*, vol. 135(5):2314-2317 (1994).

Rabinovitch, Alex et al., "Transfection of Huma Pancreatic Islets With an Anti-Apoptotic Gene (*bcl*-2) Protects $\beta$-Cells From Cytokine-Induced Destruction," *Diabetes*, vol. 48:1223-1229 (1999).

Raman, Kathleen G. et al., "Inhaled carbon monoxide inhibits intimal hyperplasia and provides added benefit with nitric oxide," *J. Vasc. Surg.*, vol. 44:151-158 (2006).

Ramlawi, Basel et al., "Inhaled Carbon Monoxide Prevents Graft-Induced Intimal Hyperplasia in Swine," *Journal of Surgical Research*, vol. 138:121-127 (2007).

Rensing, Hauke et al., "Differential activation pattern of redox-sensitive transcription factors and stress-inducible dilator systems heme oxygenase-1 and inducible nitric oxide synthase in hemorrhagic and endktoxic shock," *Crit. Care Med.*, vol. 29(10):1962-1971 (2001).

Ringel, S.P. et al., "Carbon Monoxide-induced Parkinsonism," *Journal of the neurological Sciences*, vol. 16:245-251 (1972).

Roberts, James R. et al., "Successful Heart Transplantation From a Victim of Carbon-Monoxide Poisoning," *Annals of Emergency Medicine*, vol. 26(5):652-655 (1995).

Rücker, Martin et al., "Reduction of inflammatory response in composite flap transfer by local stress conditioning-induced heat-shock protein 32," *Surgery*, vol. 129:292-301 (2001).

Ryter, Stefan W. et al., "Heme Oxygenase-1/Carbon Monoxide From Basic Science to Therapeutic Applications," *Physiol. Rev.*, vol. 86:583-650 (2006).

Ryter, Stefan W. et al., "Heme oxygenase/carbon monoxide signaling pathways: Regulation and functional significance," *Molecular and Cellular Biochemistry*, vol. 234/235:249-263 (2002).

Ryter, Stefan W. et al., "Heme Oxygenase-1: Molecular Mechanisms of Gene Expression in Oxygen-Related Stress," *Antioxidants & Redox Signaling*, vol. 4(4):625-632 (2002).

Ryter, Stefan W. et al., "Regulation of endothelial heme oxygenase activity during hypoxia is dependent on chelatable iron," *Am. J. Physiol. Heart Circ. Physiol.*, vol. 279:H2889-H2897 (2000).

Ryter, Stefan et al., "Mitogen activated protein kinase (MAPK) pathway regulates heme oxygenase-1 gene expression by hypoxia in vascular cells," *Exp. Biol. Med.*, vol. 228(5):607 (2003).

Ryter, Stefan W. et al., "Therapeutic applications of carbon monoxide in lung disease," *Current Opinion in Pharmacology*, vol. 6:257-262 (2006).

Sarady, Judit K. et al., "Carbon Monoxide Modulates Endotoxin-Induced Production of Granulocyte Macrophage Colony-Stimulating Factor in Macrophages," *Am. J. Respir. Cell Mol. Biol.*, vol. 27:739-745 (2002).

Sarady, Judit K. et al., "Cytoprotection by heme oxygenase/CO in the lung," *Disease Markers in Exhaled Breath, Basic Mechanisms and Clinical Applications*, Nandor Marczin, Ed., IOS Press, pp. 73-78 (2002).

Sasidhar, Madhu et al., "Exogenous Carbon Monoxide Attenuates Mitogen Activated Protein Kinase (MAPK) Activation in Rat Pulmonary Artery Endothelial Cells Exposed to Hypoxia," *American Journal of Respiratory and Critical Care Medicine*, vol. 159(3):A352 (1999).

Sass, Gabriele et al., "Heme Oxygenase-1 and Its Reaction Product, Carbon Monoxide, Prevent Inflammation-Related Apoptotic Liver Damage in Mice," *Hepatology*, vol. 38:909-918 (2003).

Sato, K. et al., "Heme Oxygenase-1 or Carbon Monoxide Prevents the Inflammatory Response Associated with Xenograft Rejection," *Acta Haematologica*, vol. 103(Suppl. 1) No. 345 (2000).

Sato, Koichiro et al., "Carbon monoxide can fully substitute Heme Oxygenase-1 in suppressing the rejection of mouse to rat cradiac transplants," *Acta Haematologica*, vol. 103(Suppl. 1) No. 348 (2000).

Sato, Koichiro et al., "Carbon Monoxide Generated by Heme Oxygenase-1 Suppresses the Rejection of Mouse-to-Rat Cardiac Transplants," *The Journal of Immunology*, vol. 166;4185-4194 (2001).

Schipper, H.M. et al., "Expression of Heme Oxygenase-1 in the Senescent and Alzheimer-diseased Brain," *Ann. Neurol.*, vol. 37:758-768 (1995).

Sethi, Jigme E. et al., "Differential Modulation by Exogenous Carbon Monoxide of TNF-α Stimulated Mitogen-Activated Protein Kinases in Rat Pulmonary Artery Endothelial Cells," *Antioxidants & Redox Signaling*, vol. 4(2):241-248 (2002).

Seyfried, S. et al., "HO-1 Induction protects mice from immune-mediated liver injury," *Naunyn-Schmiedebert's Archives of Pharmacology*, vol. 367:R80 (2003).

Shapiro, A.M. James et al., "Islet Transplantation in Seven Patients with Type 1 Diabetes Mellitus Using a Glucocorticoid-Free Immunosuppressive Regimen," *The New England Journal of Medicine*, vol. 343(4):230-238 (2000).

Shennib, Hani et al., "Successful Transplantation of a Lung Allograft from a Carbon Monoxide-poisoning Victim," *J. Heart Lung Transplant*, vol. 11:68-71 (1992).

Singhal, Aneesh B. et al., "Effects of Normobaric Hyperoxia in a Rat Model of Focal Cerebral Ischemia-Reperfusion," *Journal of Cerebral Blood Flow & Metabolism*, vol. 22:861-868 (2002).

Siow, Richard C.W. et al., "Heme oxygenase-carbon monoxide signalling pathway in atherosclerosis: anti-atherogenic actions of bilirubin and carbo monoxide," *Cardiovascular Research*, vol. 41:385-394 (1999).

Slebos, Dirk-Jan et al., "Heme oxygenase-1 and carbon monoxide in pulmonary medicine," *Respiratory Research*, vol. 4(7):1-13 (2003).

Smith, Julian A. et al., "Successful Heart Transplantation with Cardiac Allografts Exposed to Carbon Monoxide Poisoning," *J. Heart Lung Transplant*, vol. 11:698-700 (1992).

Soares, M.P. et al., "Expression of heme oxygenase-1 can determine cardiac xenograft survival," *Nature Medicine*, vol. 4(9):1073-1077 (1998).

Soares, Miguel P. et al., "Heme oxygenase-1, a protective gene that prevents the rejection of transplanted organs," *Immunological Reviews*, vol. 184:275-285 (2001).

Soares, Miguel P. et al., "Heme Oxygenase-1 and/or Carbon Monoxide can Promote Organ Graft Survival," *Disease Markers in Exhaled Breath*, N. Marczin and M.H. Yacoub, Eds., IOS Press, pp. 267-273 (2002).

Soares, Miguel P. et al., "Modulation of Endothelial Cell Apoptosis by Heme Oxygenase-1-Derived Carbon Monoxide," *Antioxidants & Redox Signaling*, vol. 4(2):321-329 (2002).

Song, Ruiping et al., "Carbon Monoxide Induces Cytoprotection in Rat Orthotopic Lung Transplantation via Anti-Inflammatory and Anti-Apoptotic Effects," *American Journal of Pathology*, vol. 163(1):231-242 (2003).

Song, Ruiping et al., "Carbon Monoxide Inhibits Human Airway Smooth Muscle Cell Proliferation via Mitogen-Activated Protein Kinase Pathway," *Am. J. Respir. Cell Mol. Biol.*, vol. 27:603-610 (2002).

Song, Ruiping et al., "Regulation of IL-1β-induced GM-CSF production in human airway smooth muscle cells by carbon monoxide," *Am. J. Physiol. Lung Cell Mol. Physiol.*, vol. 284:L50-L56 (2003).

Stewart, Richard D. et al., "The Effect of Carbon Monoxide on Humans," *Journal of Occupational Medicine*, vol. 18(5):304-309 (1976).

Stewart, Richard D., "The Effects of Low Concentrations of Carbon Monoxide in Man," *Scandinavian Journal of Respiratory Diseases Suppl.*, vol. 91:56-62 (1974).

Stocker, Roland et al., "Bilirubin Is an Antioxidant of Possible Physiological Importance," *Science*, vol. 235(4792):1043-1046 (1987).

Stupfel, Maurice et al., "Physijological and Biochemical Effects on Rats and Mice Exposed to Small Concentrations of Carbon Monoxide for Long Periods," *Annals of the New York Academy of Sciences*, vol. 174:342-368 (1970).

Suganuma, Masami et al., "A New Process of Cancer Prevention Mediated through Inhibition of Tumor Necrosis Factor α Expression," *Cancer Research*, vol. 56:3711-3715 (1996).

Tamayo, Luis et al., "Carbon monoxide inhibits Hypoxic pulmonary vasoconstriction in rats by a cGMP-independent mechanism," *Pflügers Arch.—Eur. J. Physiol.*, vol. 434:698-704 (1997).

Tamion, Fabienne et al., "Intestinal preconditioning prevents systemic inflammatory response in hemorrhagic shock. Role of HO-1," *Am. J. Physiol. Gastrointest. Liver Physiol.*, vol. 283:G408-G414 (2002).

Taylor, Peter C., "Anti-TNF Therapy for Rheumatoid Arthritis and Other Inflammatory Diseases," *Molecular Biotechnology*, vol. 19:153-168 (2001).

Tenderich, Gero et al., "Hemodynamic Follow-up on Cardiac Allografts from Poisoned Donors," *Transplantation*, vol. 66(9):1163-1167 (1998).

Tenhunen, Raimo et al., "The Enzymatic Conversion of Heme to Bilirubin by Microsomal Heme Oxygenase," *Proc. Natl. Acad. Sci. USA*, vol. 61(2):748-755 (1968).

Thiemermann, Christoph, "Inhaled CO: Deadly gas or novel therapeutic?" *Nature Medicine*, vol. 7(5):534-535 (2001).

Thom, Stephen R. et al., "Therapeutic Carbon Monoxide May be Toxic," *American Journal of Respiratory and Critical Care Medicine*, vol. 171:1318 (2005).

Tobiasch, Edda et al., "Heme Oxygenase-1 Protects Pancreatic β Cells From Apoptosis Caused by Various Stimuli," *Journal of Investigative Medicine*, vol. 49(6):566-571 (2001).

Toda, Koichi et al., "Exogenous Carbon Monoxide Protects Endothelial Cells Against Oxidant Stress and Improves Graft Function after Lung Transplantation," *Circulation*, vol. 98(17):I265 (1998).

Togane, Yuko et al., "Protective roles of endogenous carbon monoxide in neointimal development elicited by arterial injury," *Am. J. Physiol. Heart Circ. Physiol.*, vol. 278:H623-H632 (2000).

Tulis, David A. et al., "Adenovirus-Mediated Heme Oxygenase-1 Gene Delivery Inhibits Injury-Induced Vascular Neointima Formation," *Circulation*, vol. 104:2710-2715 (2001).

Utz, J. et al., "Carbon monoxide relaxes ileal smooth muscle through activation okf guanylate cyclase," *Biochemical Pharmacology*, vol. 41(8):1195-1201 (1991).

Vachharajani, Tushar J. et al., "Heme oxygenase modulates selectin expression in different regional vascular beds," *Am. J. Physiol. Heart Circ. Physiol.*, vol. 278:H1613-H1617 (2000).

Vassalli, F. et al., "Inhibition of hypoxic pulmonary vasoconstriction by carbon monoxide in dogs," *European Respiratory Journal*, ERS Annual Congress, Geneva, Switzerland, Sep. 19-23, Abstract No. 1595 (1998).

Verma, Ajay et al., "Carbo Monoxide: A Putative Neural Messenger," *Science*, vol. 259:381-384 (1993).

Verran, Deborah et al., "Use of Liver Allografts from Carbon Monoxide Poisoned Cadaveric Donors," *Transplantation*, vol. 62(10):1514-1515 (1996).

Vitek, Libor et al., "Gilbert syndrome and ischemic heart disease: a protective effect of elevated bilirubin levels," *Atherosclerosis*, vol. 160:449-456 (2002).

Vreman, Hendrick J. et al., "Carbon Monoxide and Carboxyhemoglobin," *Advances in Pediatrics®*, vol. 42:303-334 (1995).

Wang Rui et al., "Carbon monoxide-induced vasorelaxation and the underlying mechanisms," *British Journal of Pharmacology*, vol. 121:927-934 (1997).

Wang, Rui, "Resurgance of carbon monoxide: an endogenous gaseous vasorelaxing factor," *Can. J. Physiol. Pharmacol.*, vol. 76:1-15 (1998).

Wang, W.P. et al., "Protective role of heme oxygenase-1 on trinitrobenzene sulfonic acid-induced colitis in rats," *Am. J. Physiol. Gastrointest. Liver Physiol.*, vol. 281:G586-G594 (2001).

WebMD, "Carbon Monoxide Poisoning: Symptoms," retrieved online at http://www.webmd.com/a-to-z-guides/carbon-monoxide-poisoning-symptoms, retrieved Jul. 11, 2005.

WebMD, "Carbon Monoxide Poisoning: What Happens," retrieved online at http://www.webmd.com/a-to-z-guides/carbon-monoxide-poisoning-what-happens, retrieved Jul. 11, 2005.

Weir, Gordon C. et al., "Islet transplantation as a treatment for diabetes," *Journal of the American Optometric Association*, vol. 69(11):727-732 (1998).

Weir, Gordon C. et al., "Scientific and Political Impediments to Successful Islet Transplantation," *Diabetes*, vol. 46:1247-1256 (1997).

Welty, S.E. et al., "Hyperoxic Lung Injury is Potentiated by SPC-Promotor Driven Expression of an HO-1 Transgene in Mice," *American Journal of Respiratory and Critical Care Medicine*, vol. 159(3):A218 (1999).

Weng, Yi-Hao et al., "Transpulmonary HO-1 Gene Delivery in Neonatal Mice," *American Journal of Respiratory and Critical Care Medicine*, vol. 159(3):A218 (1999).

Willoughby, D.A. et al., "Resolution of inflammation," *International Journal of Immunopharmacology*, vol. 22:1131-1135 (2000).

Yamashita, Kenichiro et al., "Effects of HO-1 induction and carbon monoxide on cardiac transplantation in mice," *Exp. Biot. Med.*, vol. 228(5):616 (2003).

Yet, Shaw-Fang et al., "Herne Oxygenase 1 in Regulation of Inflammation and Oxidative Damage," *Methods in Enzymology*, vol. 353:163-176 (2002).

Yuan, Shi et al., "Evidence of Increased Endogenous Carbon Monoxide Production in Newborn Rat Endotoxicosis," *Chin. Med. Sci. J.*, vol. 12(4):212-215 (1997).

Zegdi, Rachid et al., "Increased endogenous carbon monoxide production in severe sepsis," *Intensive Care Med.*, vol. 28:793-796 (2002).

Zhang, Xuchen et al., "Carbon Monoxide Inhibition of Apoptosis during Ischemia-Reperfusion Lung Injury Is Dependent on the p38 Mitogen-activated Protein Kinase Pathway and Involves Caspase 3," *The Journal of Biological Chemistry*, vol. 278(2):1248-1258 (2003).

Zhang, Xuchen et al., "Mitogen-activated protein kinases regulate HO-1 gene transcription after ischemia-reperfusion lung injury," *Am. J. Physiol. Cell Mol. Physiol.*, vol. 283:L815-L829 (2002).

Zhang, Y. Clare et al., "Adeno-Associated Virus-Mediated IL-10:Gene Therapy Inhibits Diabetes Recurrence in Syngeneic Islet Cell Transplantation of NOD Mice," *Diabetes*, vol. 52:708-716 (2003).

Zuckerbraun, Brian S. et al., "Carbon Monoxide Protects against Liver Failure through Nitric Oxide-induced Heme Oxygenase 1," *J. Exp. Med.*, vol. 198(11):1707-1716 (2003).

Zuckerbraun, Brian S. et al., "Carbon Monoxide Inhibits Intestinal Inducible nitric oxide synthase production and ameliorates intestinal inflammation in experimental NEC," *J. Am. College of Surgeons*, vol. 197:S50 (2003).

Zuckerbraun, Brian S. et al., "Carbon monoxide protects hepatocytes from TNF-alpha/actinomycin D induced cell death," *Critical Care Medicine*, vol. 29:A59 (2001).

Zuckerbraun, Brian S. et al., "Heme Oxygenase-1: A Cellular Hercules," *Hepatology*, vol. 37(4):742-744 (2003).

Zuckerbraun, Brian S. et al., "Carbon Monoxide Attenuates the Development of Necrotizing Enterocolitis in an Animal Model," *Surgical Infections*, vol. 3(1):83 (2002).

International Search Report for Application No. PCT/US3/11411, dated Aug. 12, 2003.

Japanese Office Action for Application No. 2003-585506, dated Nov. 26, 2009.

Supplementary European Search Report for Application No. 03746978.0, dated Sep. 24, 2009.

International Search Report for Application No. PCT/US2007/016032, dated Dec. 21, 2007.

International Search Report for Application No. PCT/US2007/016023, dated May 2, 2008.

Duckers, Henricus J. et al., "Heme oxygenase-1 protects against vascular construction and proliferation," *Nature Medicine*, vol. 7(6):693-698 (2001).

Keyse, Stephen et al., "Heme oxygenase is the major 32-kDa stress protein induced in human skin fibroblasts by UVA radiation, hydrogen peroxide, and sodium arsenite," *Proc. Natl. Acad. Sci. USA*, vol. 86:99-103 (1989).

Maines, Mahin D., "The Heme Oxygenase System: A Regulator of Second Messenger Gases," *Annu. Rev. Pharmacol. Toxicol.*, vol. 37:517-554 (1997).

Tenhunen, Raimo et al., "The enzymatic catabolism of hemoglobin: Stimulation of microsomal heme oxygenase by hemin," *J. Lab. Clin. Med.*, vol. 75(3):410-421 (1970).

\* cited by examiner

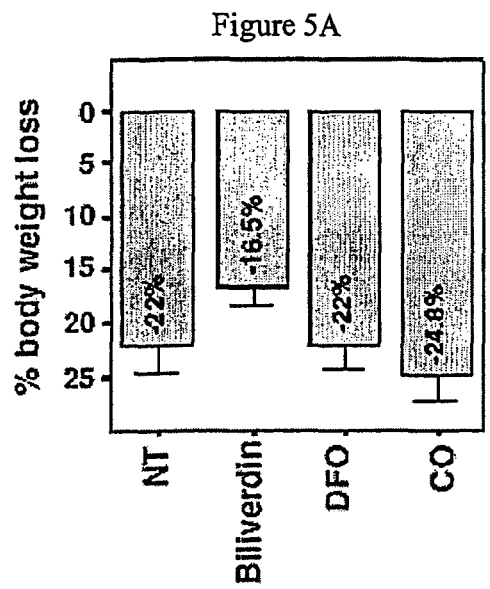
Figure 5A
Figure 5B
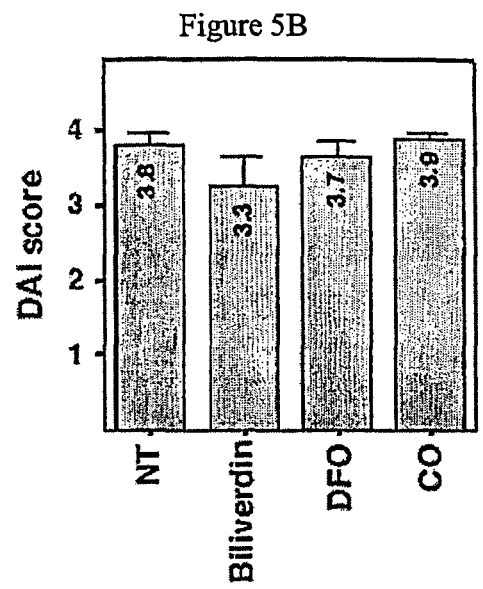
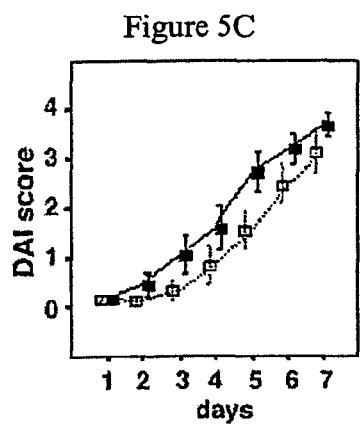
Figure 5C
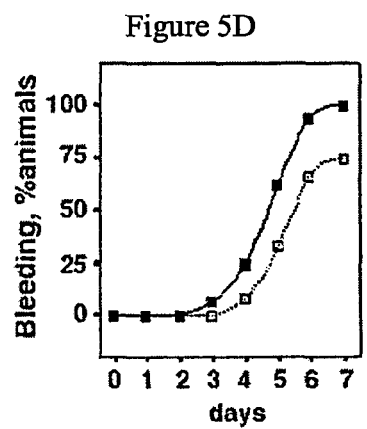
Figure 5D
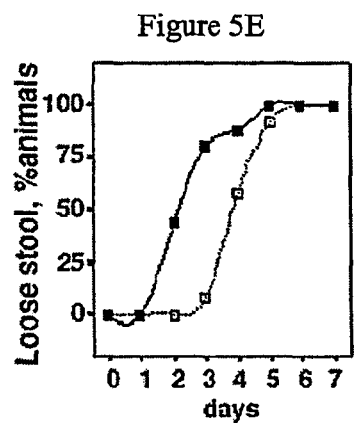
Figure 5E

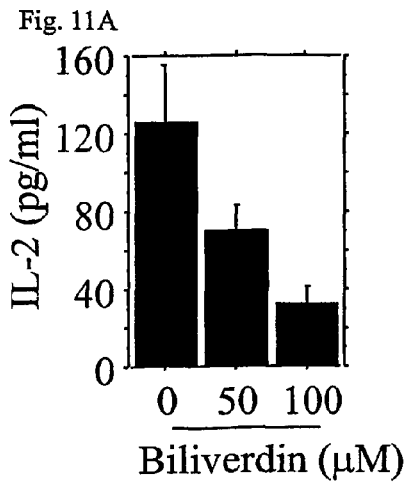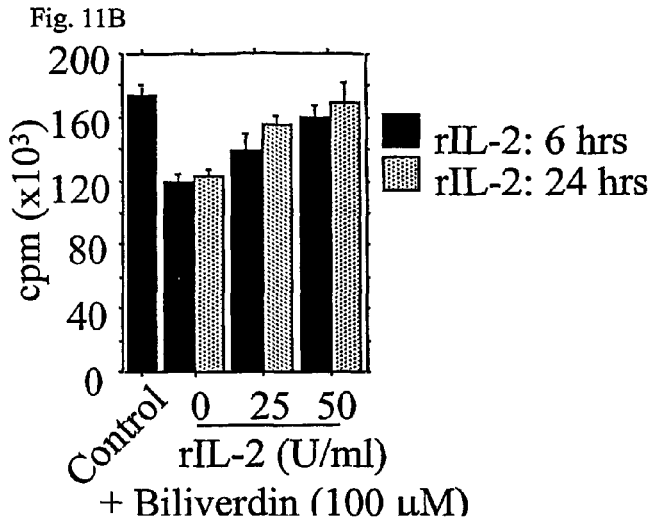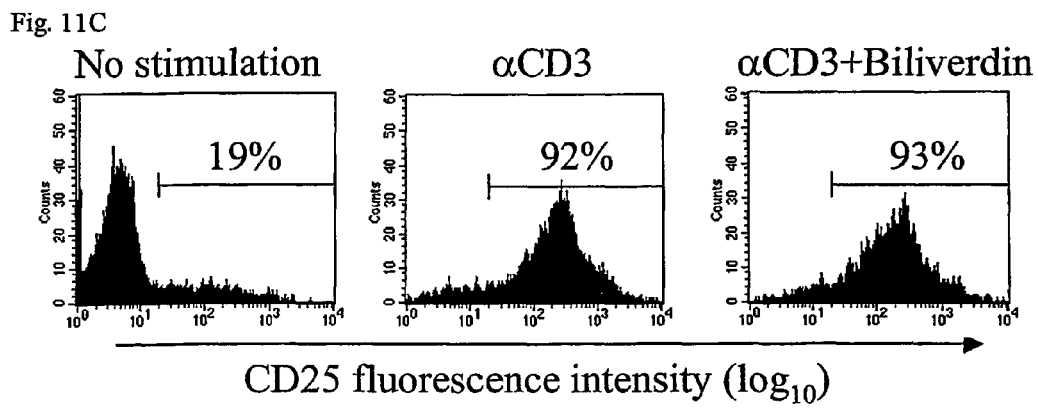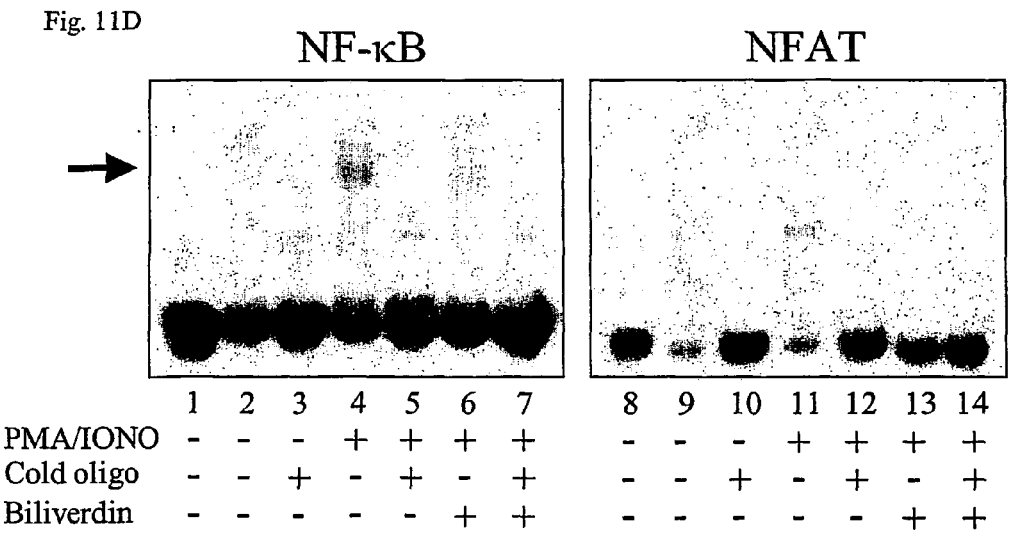

Figure 15
a) Control situation
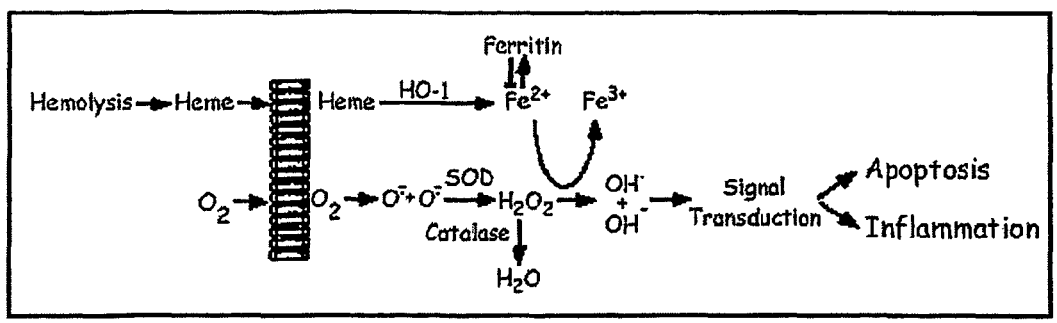
b) Recombinant H-ferritin adenovirus
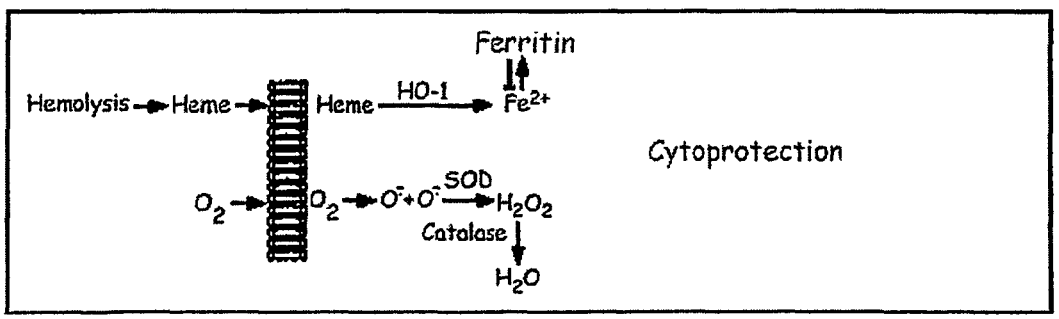

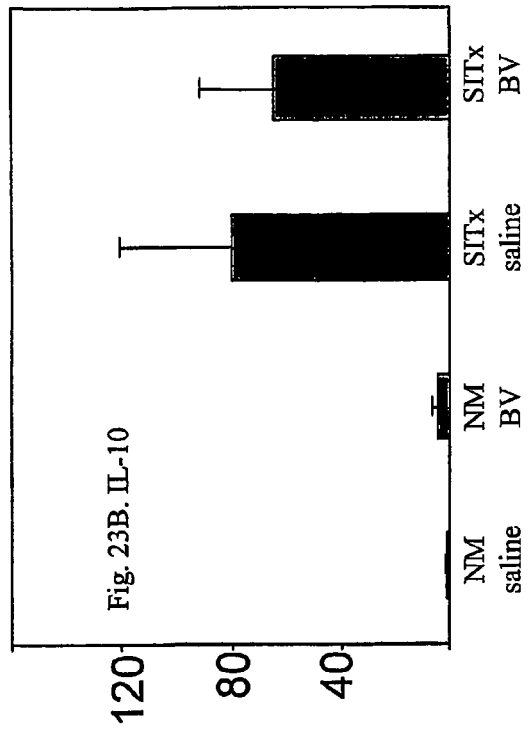
Fig. 23B. IL-10
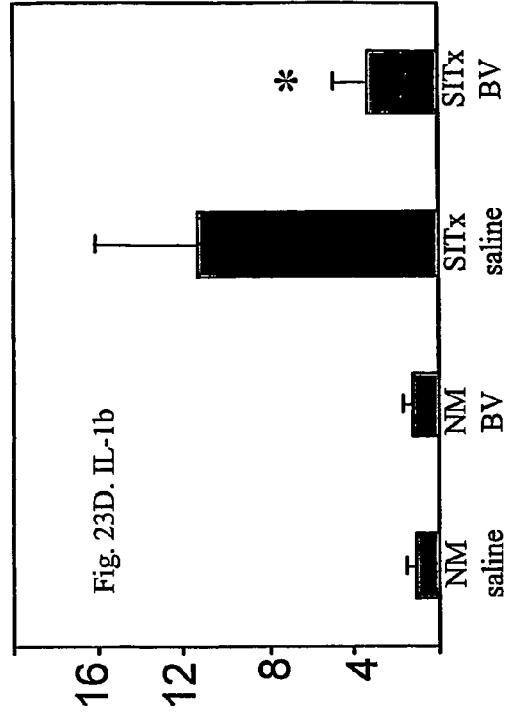
Fig. 23D. IL-1b
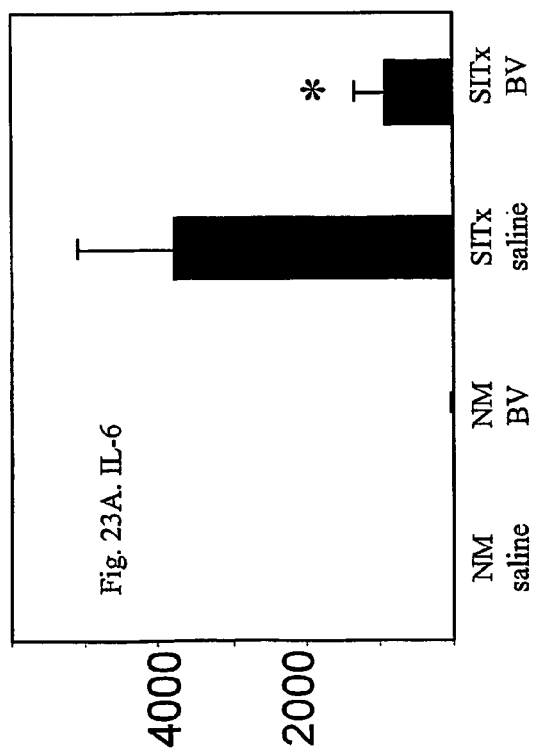
Fig. 23A. IL-6
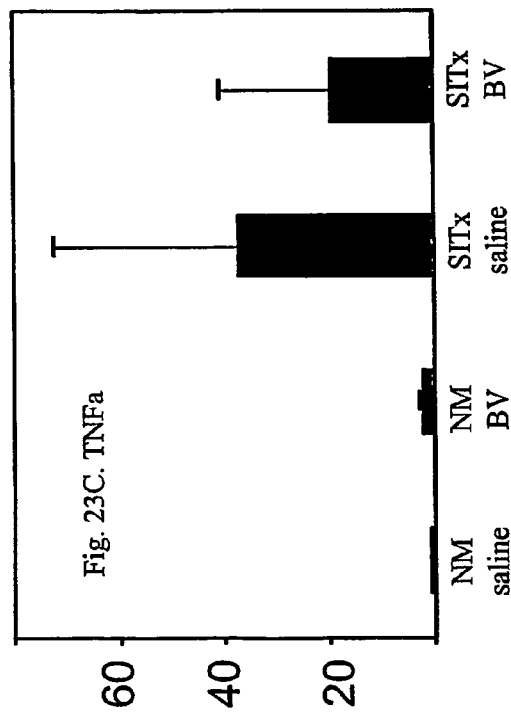
Fig. 23C. TNFa

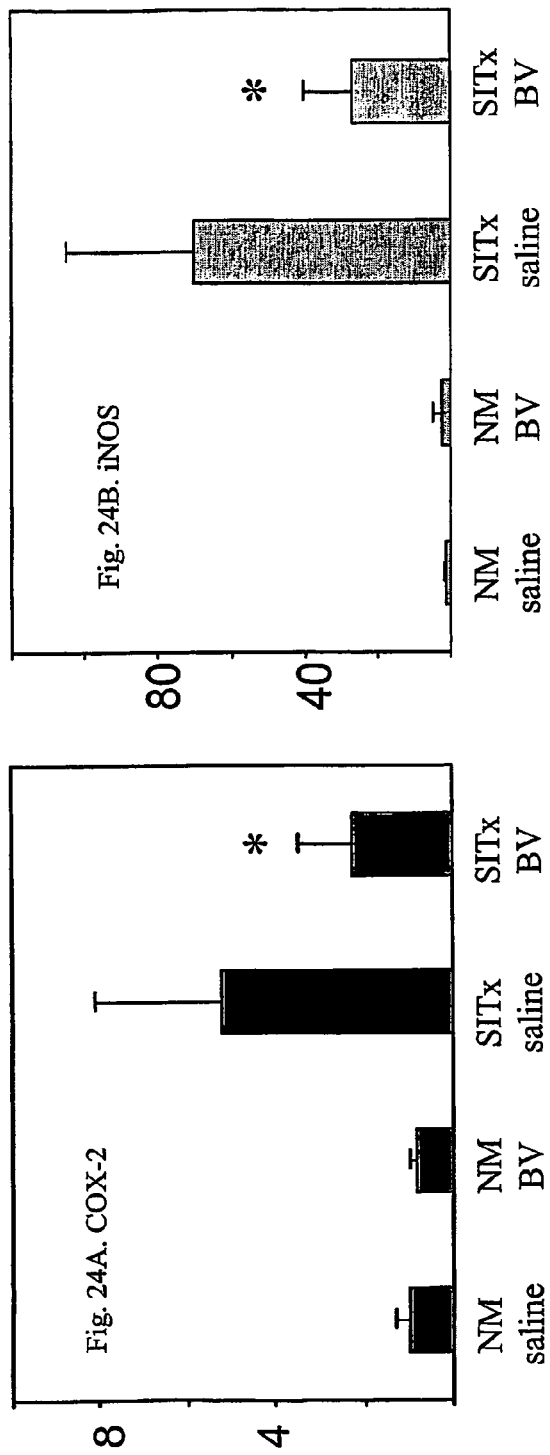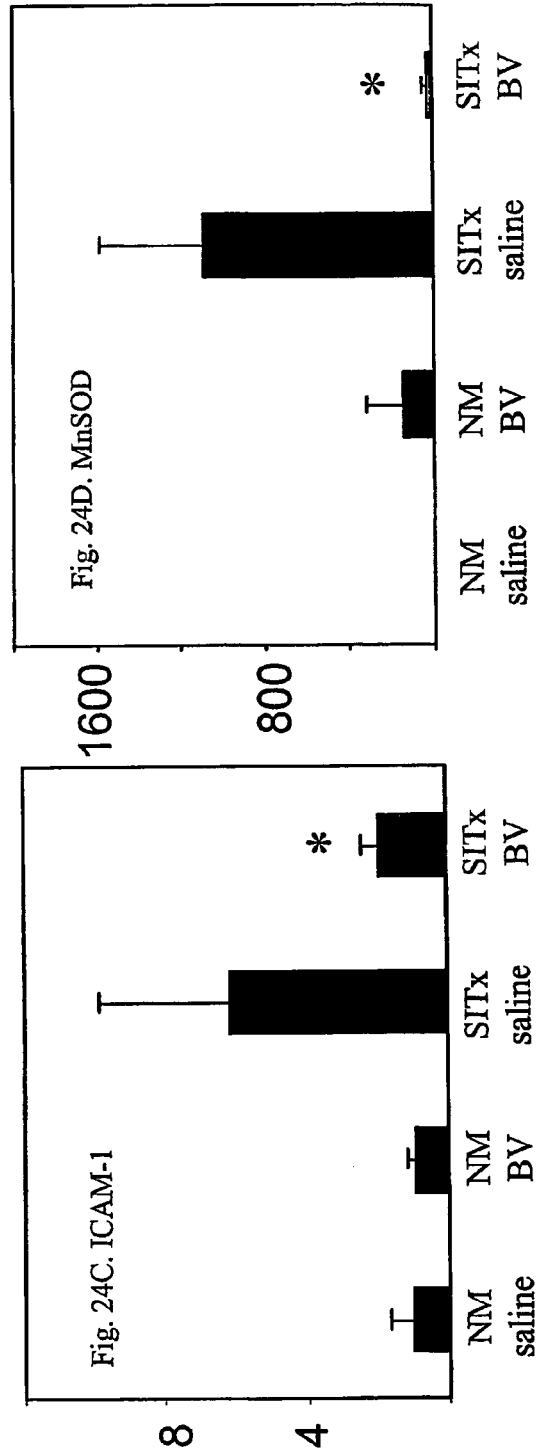
Fig. 24A. COX-2
Fig. 24B. iNOS
Fig. 24C. ICAM-1
Fig. 24D. MnSOD

METHODS OF TREATING INFLAMMATION BY ADMINISTRATION OF HEME OXYGENASE-1 AND PRODUCTS OF HEME DEGRADATION

CLAIM OF PRIORITY

This application is a National Stage of International Application No. PCT/US03/11411, filed Apr. 15, 2003, which claims priority under 35 USC §119(e) to U.S. Provisional Patent Application Ser. No. 60/372,762, filed on Apr. 15, 2002, the entire contents of which are hereby incorporated by reference.

FEDERALLY SPONSORED RESEARCH OR DEVELOPMENT

This invention was made with Government support under Grant No. HL58688 awarded by the National Institutes of Health. The Government has certain rights in the invention.

TECHNICAL FIELD

The present invention relates to the treatment of disorders using heme oxygenase-1 and heme degradation products.

BACKGROUND

Heme oxygenase-1 (HO-1) catalyzes the first step in the degradation of heme. HO-1 cleaves the α-meso carbon bridge of b-type heme molecules by oxidation to yield equimolar quantities of biliverdin IXa, carbon monoxide (CO), and free iron. Subsequently, biliverdin is converted to bilirubin via biliverdin reductase, and the release of $Fe^{2+}$ from heme induces the expression of the $Fe^{2+}$ sequestering protein ferritin, which acts as an anti-oxidant by limiting the ability of $Fe^{2+}$ to participate in the generation of free radicals through the Fenton reaction.

SUMMARY

The present invention is based, in part, on the discovery that the administration of degradation products of heme and/or HO-1 can attenuate inflammation and suppress the damage associated with ischemia.

Accordingly, the present invention features a method of reducing inflammation in a patient that includes identifying a patient suffering from or at risk for inflammation, and administering to the patient a treatment including inducing ferritin in the patient; expressing ferritin in the patient; and/or administering a pharmaceutical composition comprising HO-1, bilirubin, biliverdin, ferritin, iron, desferoxamine (DFO), salicylaldehyde isonicotinoyl hydrazone (SIH), iron dextran, and/or apoferritin to the patient, in an amount sufficient to reduce inflammation.

In one embodiment, the treatment is administering a pharmaceutical composition that includes biliverdin. The pharmaceutical composition can be administered to the patient at a dosage of, for example, about 1 to 1000 micromoles/kg/day, e.g., 10 to 500 μmols/kg/day, 20 to 200 μmols/kg/day, or 25 to 100 μmols/kg/day.

Alternatively or in addition, the treatment can include administering a pharmaceutical composition that includes bilirubin to the patient. The pharmaceutical composition can be administered to a patient to generate serum levels of bilirubin in a range of from about 1 to about 300 μmols/L, e.g., about 10 to about 200 μmols/L, or about 50 to about 100 μmols/L. Individual doses of bilirubin can be administered, which can fall within the range of about 1 to 1000 mg/kg, e.g., 10 to 500 mg/kg, 20 to 200 mg/kg, or 25 to 150 mg/kg.

Further, the treatment can include administering a pharmaceutical composition that includes apoferritin to the patient. The pharmaceutical composition can be administered to the patient at a dosage of, for example, about 1 to 1000 mg/kg, e.g., 10 to 500 mg/kg, 20 to 200 mg/kg, or 25 to 150 mg/kg.

The treatment can also include administering a pharmaceutical composition that includes DFO to the patient. The pharmaceutical composition can be administered to the patient at a dosage of, for example, about 0.1 to 1000 mg/kg, e.g., 0.5 to 800 mg/kg, 1 to 600 mg/kg, 2 to 400 mg/kg, or 2.5 to 250 mg/kg.

Further, the treatment can include administering a pharmaceutical composition that includes iron dextran to the patient. The pharmaceutical composition can be administered to the patient at a dosage of, for example, about 1 to 1000 mg/kg, e.g., 10 to 900 mg/kg, 100 to 800 mg/kg, 300 to 700 mg/kg, or 400 to 600 mg/kg. Alternatively, free iron, e.g., in the form of iron supplements, can be delivered to the patient.

The treatment can also include administering a pharmaceutical composition that includes salicylaldehyde isonicotinoyl hydrazone (SIH) to the patient. The pharmaceutical composition can be administered to the patient orally or parenterally at a dosage of, for example, about 0.02 to 100 mmol/kg, e.g., about 0.02 to 10 mmol/kg, e.g., 0.02 to 50 mmol/kg, or 0.2 to 20 mmol/kg.

The inflammation can be associated with a condition including, but not limited to, asthma, adult respiratory distress syndrome, interstitial pulmonary fibrosis, pulmonary emboli, chronic obstructive pulmonary disease, primary pulmonary hypertension, chronic pulmonary emphysema, congestive heart failure, peripheral vascular disease, stroke, atherosclerosis, ischemia-reperfusion injury, heart attacks, glomerulonephritis, conditions involving inflammation of the kidney, infection of the genitourinary tract, viral and toxic hepatitis, cirrhosis, ileus, necrotizing enterocolitis, specific and non-specific inflammatory bowel disease, rheumatoid arthritis, deficient wound healing, Alzheimer's disease, Parkinson's disease, graft versus host disease, or hemorrhagic, septic, or anaphylactic shock.

In an embodiment of the present invention, the inflammation is inflammation of the heart, lung, liver, pancreas, joints, eye, bronchi, spleen, brain, skin, and/or kidney. The inflammation can also be an inflammatory condition localized in the gastrointestinal tract. The inflammatory condition can be, for example, amoebic dysentery, bacillary dysentery, schistosomiasis, *campylobacter* enterocolitis, *yersinia* enterocolitis, *enterobius vermicularis*, radiation enterocolitis, ischaemic colitis, eosinophilic gastroenteritis, ulcerative colitis, indeterminate colitis, and Crohn's disease.

The method can further include the step(s) of inducing and/or expressing HO-1 in the patient and/or administering a pharmaceutical composition comprising carbon monoxide to the patient.

In another aspect, the invention features a method of transplanting an organ, which includes administering to a donor a treatment including inducing HO-1 or ferritin in the donor; expressing ferritin in the donor; and/or administering a pharmaceutical composition comprising HO-1, bilirubin, biliverdin, ferritin, desferoxamine, salicylaldehyde isonicotinoyl hydrazone, iron dextran, and/or apoferritin to the donor; obtaining an organ from the donor; and transplanting the organ into a recipient, wherein the treatment administered is sufficient to enhance survival or function of the organ after transplantation into the recipient. In certain embodiments, the method further includes the step(s) of inducing and/or expressing HO-1 in the donor and/or administering a pharmaceutical composition comprising carbon monoxide to the donor.

The invention also features a method of transplanting an organ, which includes providing an organ of a donor; administering to the organ ex vivo a treatment including inducing HO-1 or ferritin in the organ, expressing HO-1 or ferritin in the organ, and/or administering a pharmaceutical composition comprising HO-1, bilirubin, biliverdin, ferritin, desferoxamine, salicylaldehyde isonicotinoyl hydrazone, iron dextran, and/or apoferritin; and transplanting the organ into a recipient, wherein treatment administered to the organ is sufficient to enhance survival or function of the organ after transplantation. In certain embodiments, the method further includes the step(s) of inducing and/or expressing HO-1 in the organ and/or administering a pharmaceutical composition comprising carbon monoxide to the organ.

Further, the invention features a method of transplanting an organ, which includes providing an organ from a donor; transplanting the organ into a recipient; and before, during, or after the transplanting step, administering to the recipient a treatment including inducing HO-1 or ferritin in the recipient, expressing HO-1 or ferritin in the recipient, and/or administering a pharmaceutical composition comprising HO-1, bilirubin, biliverdin, ferritin, desferoxamine, salicylaldehyde isonicotinoyl hydrazone, iron dextran, and/or apoferritin to the recipient, wherein the treatment administered to the recipient is sufficient to enhance survival or function of the organ after transplantation of the organ to the recipient. In certain embodiments, the method further includes the step(s) of inducing and/or expressing HO-1 in the recipient and/or administering a pharmaceutical composition comprising carbon monoxide to the recipient.

In another aspect, the invention provides a method of performing angioplasty on a patient, which includes performing angioplasty on the patient; and before, during, or after the performing step, administering a treatment including inducing HO-1 or ferritin in the patient, expressing HO-1 or ferritin in the patient, and/or administering a pharmaceutical composition comprising HO-1, bilirubin, biliverdin, ferritin, desferoxamine, salicylaldehyde isonicotinoyl hydrazone, iron dextran, and/or apoferritin to the patient. In certain embodiments, the method further includes the step(s) of inducing and/or expressing HO-1 in the patient and/or administering a pharmaceutical composition comprising carbon monoxide to the patient.

The invention also features a method of performing vascular surgery on a patient, which includes performing vascular surgery on the patient; and before, during, or after performing the vascular surgery, administering to the patient at least one treatment including inducing HO-1 or ferritin in the patient, expressing ferritin in the patient, and/or administering a pharmaceutical composition comprising HO-1, bilirubin, biliverdin, ferritin, desferoxamine, salicylaldehyde isonicotinoyl hydrazone, iron dextran, and/or apoferritin. In certain embodiments, the method includes the step(s) of inducing and/or expressing HO-1 in the patient and/or administering a pharmaceutical composition comprising carbon monoxide to the patient.

In yet another aspect, the invention features a method of treating a cellular proliferative and/or differentiative disorder in a patient, which includes identifying a patient suffering from or at risk for a cellular proliferative and/or differentiative disorder; and administering to the patient at least one treatment including inducing ferritin in the patient, expressing ferritin in the patient, and/or administering a pharmaceutical composition comprising HO-1, bilirubin, biliverdin, ferritin, iron, desferoxamine, salicylaldehyde isonicotinoyl hydrazone, iron dextran, and/or apoferritin to the patient, in an amount sufficient to treat the cellular proliferative and/or differentiative disorder. In certain embodiments, the method further includes the step(s) of inducing and/or expressing HO-1 in the patient and/or administering a pharmaceutical composition comprising carbon monoxide to the patient.

In still another aspect, the invention features a method of reducing the effects of ischemia in a patient, which includes identifying a patient suffering from or at risk for ischemia; and
administering to the patient at least one treatment including inducing ferritin in the patient, expressing ferritin in the patient, and/or administering a pharmaceutical composition comprising HO-1, bilirubin, biliverdin, ferritin, iron, desferoxamine, salicylaldehyde isonicotinoyl hydrazone, iron dextran, and/or apoferritin to the patient, in an amount sufficient to reduce the effects of ischemia. In certain embodiments, the method further includes the step(s) of inducing and/or expressing HO-1 in the patient and/or administering a pharmaceutical composition comprising carbon monoxide to the patient.

The term "pharmaceutical composition" is used throughout the specification to describe a gaseous, liquid, or solid composition containing an active ingredient, e.g., HO-1 or ferritin (or an inducer of HO-1 or ferritin), bilirubin, and/or biliverdin, that can be administered to a patient and/or an organ. The invention contemplates use of any two, three, four, or five of these in combination or in sequence. The skilled practitioner will recognize which form of the pharmaceutical composition, e.g., gaseous, liquid, and/or solid, is preferred for a given application. Further, the skilled practitioner will recognize which active ingredient(s) should be included in the pharmaceutical composition for a given application.

The term "patient" is used throughout the specification to describe an animal, human or non-human, to whom treatment according to the methods of the present invention is provided. Veterinary applications are clearly anticipated by the present invention. The term includes but is not limited to mammals, e.g., humans, other primates, pigs, rodents such as mice and rats, rabbits, guinea pigs, hamsters, cows, horses, cats, dogs, sheep and goats.

The terms "effective amount" and "effective to treat," as used herein, refer to the administration of a pharmaceutical compositions(s) described herein in an amount or concentration and for period of time including acute or chronic administration and periodic or continuous administration that is effective within the context of its administration for causing an intended effect or physiological outcome. The terms "treat" or "treatment," are used herein to describe delaying the onset of, inhibiting, or alleviating the effects of a disease or condition, e.g., a disease or condition described herein.

Also within the invention is the use of HO-1 and/or any of the degradation products of heme, e.g., bilirubin, biliverdin, ferritin, iron, desferoxamine (DFO), salicylaldehyde isonicotinoyl hydrazone (SIH), iron dextran, and/or apoferritin, in the manufacture of a medicament for the treatment or prevention of inflammation or the damage associated with ischemia, e.g., transplantation-related ischemia. The medicament can be used in a method for treating or preventing inflammation in a patient suffering from or at risk for inflammation. The medicament can also be used in a method of organ transplantation, e.g., to reduce inflammation and ischemia-reperfusion injury. The medicament can also be used in a method of performing vascular surgery or angioplasty on a patient. The medicament can also be used in a method of treating a cellular proliferative and/or differentiative disorder in a patient. The medicament can also be used in a method of treating or preventing the effects of ischemia in a patient. The medicament can be in any form described herein, and can be administered alone or in combination with, e.g., CO.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 5A is a bar graph that illustrates the effect of treatment with biliverdin, DFO or carbon monoxide on weight loss associated with DSS-colitis, as observed on day 7 of the experiment. NT=no treatment; CO=carbon monoxide; DFO=desferoxamine.

FIG. 5B is a bar graph that illustrates the effect of treatment with biliverdin, DFO or carbon monoxide on the DSS-colitis disease activity index (DAI), as observed on day 7 of the experiment.

FIG. 5C is a line graph that illustrates the effect of treatment with biliverdin on the DSS-colitis DAI over a period of 7 days.

FIG. 5D is a line graph that illustrates the effect of treatment with biliverdin on intestinal bleeding associated with DSS-colitis over a period of 7 days.

FIG. 5E is a line graph that illustrates the effect of treatment with biliverdin on stool abnormalities associated with DSS-colitis over a period of 7 days.

FIG. 11A is a bar graph illustrating the suppressive effect of different doses of biliverdin on IL-2 secretion by splenocytes.

FIG. 111B is a bar graph illustrating the effect of adding exogenous IL-2 on the suppressive effect of different doses of biliverdin on IL-2 secretion by splenocytes.

FIG. 11C is a panel of three graphs showing the results of FACS analysis of CD25 expression in splenocytes stimulated with anti-CD3 mAb or anti-CD3 mAb plus biliverdin.

FIG. 11D is a pair of photographs illustrating the effect of biliverdin on nuclear translocation of NF-κB or NFAT, as measured by DNA-binding.

FIG. 15 is a schematic illustration of a model for the cytoprotective action of ferritin. Top panel: control; bottom panel: in cells transduced with recombinant H-ferritin adenovirus. SOD: superoxide dismutase.

FIGS. 23A-23D are bar graphs illustrating the effect of treatment with biliverdin on levels of IL-6, IL-10, TNFα and IL-1β, respectively, in a small intestine transplantation model. Real time RT-PCR analysis revealed a significant increase in mRNA expression of IL-6, IL-10, TNF-α and IL-1b in graft muscularis 4 hours after transplantation compared to unoperated animals. In the recipients treated with CO, the mean expressions for IL-6 and IL-1b mRNA, but not IL-10 or TNF-α, were significantly reduced. NM=Normal; BV=biliverdin; SITx-small intestine transplant FIGS. 24A-24D are bar graphs illustrating the effect of treatment with biliverdin on levels of COX-2; iNOS; ICAM-1, and MnSOD, respectively, in a small intestine transplantation model. iNOS and COX-2 gene expression was significantly upregulated in the muscularis of the transplanted intestine. BV treatment significantly reduced the expression of iNOS, COX-2, ICAM-1 and MnSOD mRNA in the graft muscularis extracts.

DETAILED DESCRIPTION

Figure 1A:
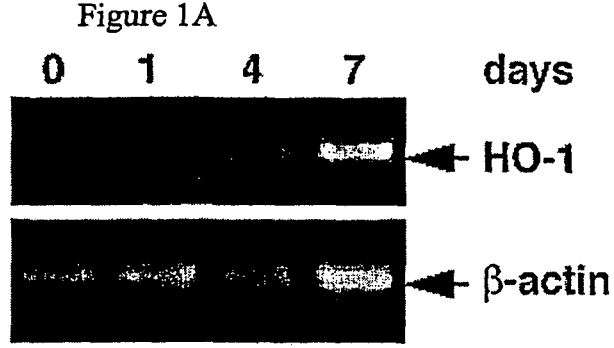
FIG. 1A is a photograph of a gel showing the results of semi-quantitative PCR analysis of HO-1 and β-actin mRNA levels after induction of DSS-colitis in control animals.

The present invention includes providing, e.g., administering, inducing and/or expressing any or all of the products of heme degradation in a patient to treat various diseases or conditions, e.g., inflammation, and/or to improve the outcome of various surgical procedures, e.g., transplant surgery. Optionally, heme oxygenase-1 (HO-1) can be provided to a patient in conjunction with administration of any or all of the products of heme degradation, e.g., carbon monoxide (CO), biliverdin, bilirubin, iron, and ferritin. Alternatively HO-1 can be provided to the patient instead of providing any or all of the products of heme degradation to the patient.

Use of Heme Oxygenase-1 and Products of Heme Degradation Heme Oxygenase-1

HO-1 can be provided to a patient by inducing or expressing HO-1 in the patient, or by administering exogenous HO-1 directly to the patient. As used herein, the term "induce(d)" means to cause increased production of a protein, e.g., HO-1 or ferritin, in the body of a patient, using the patient's own endogenous (e.g., non-recombinant) gene that encodes the protein.

HO-1 can be induced in a patient by any method known in the art. For example, production of HO-1 can be induced by hemin, by iron protoporphyrin, or by cobalt protoporphyrin. A variety of non-heme agents including heavy metals, cytokines, hormones, nitric oxide, $COCl_2$, endotoxin and heat shock are also strong inducers of HO-1 expression (Otterbein et al., Am. J. Physiol. Lung Cell Mol. Physiol. 279:L1029-L1037, 2000; Choi et al., Am. J. Respir. Cell Mol. Biol. 15:9-19, 1996; Maines, Annu. Rev. Pharmacol. Toxicol. 37:517-554, 1997; and Tenhunen et al., J. Lab. Clin. Med. 75:410-421, 1970). HO-1 is also highly induced by a variety of agents and conditions that create oxidative stress, including hydrogen peroxide, glutathione depletors, UV irradiation and hyperoxia (Choi et al., Am. J. Respir. Cell Mol. Biol. 15: 9-19, 1996; Maines, Annu. Rev. Pharmacol. Toxicol. 37:517-554, 1997; and Keyse et al., Proc. Natl. Acad. Sci. USA 86:99-103, 1989). A "pharmaceutical composition comprising an inducer of HO-1" means a pharmaceutical composition containing any agent capable of inducing HO-1 in a patient, e.g., any of the agents described herein, e.g., hemin, iron protoporphyrin, and/or cobalt protoporphyrin.

The present invention contemplates that HO-1 can be expressed in a patient via gene transfer. As used herein, the term "express(ed)" means to cause increased production of a protein, e.g., HO-1 or ferritin, in the body of a patient using an exogenously administered gene (e.g., a recombinant gene). The HO-1 or ferritin is preferably of the same species (e.g., human, mouse, rat, etc.) as the patient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retroviruses, adenoviruses, adeno-associated viruses (AAV), pox (e.g., vaccinia) viruses, human immunodeficiency virus (HIV), the minute virus of mice, hepatitis B virus, influenza virus, Herpes Simplex Virus-1, and lentiviruses) encoding HO-1 or ferritin would be administered to the patient orally, by inhalation, or by injection at a location appropriate for treatment of a condition described herein. Particularly preferred is local administration directly to the site of the condition. Similarly, plasmid vectors encoding HO-1 or ferritin can be administered, e.g., as naked DNA, in liposomes, or in microparticles.

Further, exogenous HO-1 protein can be directly administered to a patient by any method known in the art. Exogenous HO-1 can be directly administered in addition to, or as an alternative to the induction or expression of HO-1 in the patient as described herein. The HO-1 protein can be delivered to a patient, for example, in liposomes, and/or as a fusion protein, e.g., as a TAT-fusion protein (see, e.g., Becker-Hapak et al., Methods 24, 247-256, 2001). In the context of surgical procedures such as transplantation, it is contemplated that HO-1 can be induced and/or expressed in, and/or administered to donors, recipients, and/or the organ to be transplanted.

Heme Degradation Products

Additionally or alternatively, product(s) of heme degradation can be administered to patients to treat the diseases or conditions described herein. "Heme degradation products" include carbon monoxide, iron, biliverdin, bilirubin and (apo) ferritin. Any of the above can be provided to patients, e.g., as an active ingredient in a pharmaceutical composition or by other methods as described herein.

Biliverdin and Bilirubin

The terms "biliverdin" and "bilirubin" refer to the linear tetrapyrrole compounds that are produced as a result of heme degradation.

Pharmaceutical compositions comprising biliverdin and/or bilirubin are typically administered to patients in aqueous or solid forms. Biliverdin and bilirubin useful in the methods of the invention can be obtained from any commercial source, e.g., any source that supplies biochemicals for medical or laboratory use. In the preparation, use, or storage of biliverdin and bilirubin, it is recommended that the compounds be exposed to as little light as possible.

The amount of biliverdin and/or bilirubin to be included in pharmaceutical compositions and to be administered to patients will depend on absorption, distribution, inactivation, and excretion rates of the bilirubin and/or biliverdin, as well as other factors known to those of skill in the art. Effective amounts of biliverdin and/or bilirubin are amounts that are effective for treating a particular disease or condition.

Effective amounts of biliverdin can fall within the range of about 1 to 1000 micromoles/kg/day, e.g., at least 10 µmols/kg/day, e.g., at least 10, 20, 30, 40, 50, 60, 70, 80, 90, 100, 200, 300, 400, 500, 600, 700, 800, or 900 micromoles/kg/day. Preferred ranges include 10 to 500 µmols/kg/day, 20 to 200 µmols/kg/day, and 25 to 100 µmols/kg/day. Because biliverdin is rapidly converted to bilirubin in the body (via biliverdin reductase), the present invention contemplates that doses of biliverdin above 1000 micromoles/kg/day can be administered to patients. The entire dose of biliverdin can be administered as a single dose, in multiple doses, e.g., several doses per day, or by constant infusion.

Effective amounts of bilirubin can be administered to a patient to generate serum levels of bilirubin in a range of from about 1 to about 300 µmols/L, e.g., at least about 10 to about 200 µmols/L, or about 50 to about 100 µmols/L. To generate such serum levels, individual doses of bilirubin can be administered, which can fall within the range of about 1 to 1000 mg/kg, e.g., at least 10, 20, 30, 40, 50, 60, 70, 80, 90, 100, 200, 300, 400, 500, 600, 700, 800, or 900 mg/kg. Preferred ranges include 10 to 500 mg/kg, 20 to 200 mg/kg, and 25 to 150 mg/kg. The entire dose of bilirubin can be administered as a single dose, in multiple doses, e.g., several doses per day, or by constant infusion.

A skilled practitioner will appreciate that amounts of bilirubin and/or biliverdin outside of these ranges can be used depending upon the application. Acute, sub-acute, and chronic administration of pharmaceutical compositions comprising biliverdin and/or bilirubin are contemplated by the present invention, depending upon, e.g., the severity or persistence of the disease or condition in the patient. The compositions can be delivered to the patient for a time (including indefinitely) sufficient to treat the condition and exert the intended pharmacological or biological effect.

The present invention contemplates that biliverdin and/or bilirubin can be bound to carriers. Such carriers include, for example, albumin or cyclodextrin. Binding of biliverdin and/or bilirubin to such a carriers could increase the solubility of biliverdin and/or bilirubin, thereby preventing deposition of biliverdin and/or bilirubin in the tissues. The present invention contemplates that it is possible to individually administer unbound biliverdin and/or bilirubin and albumin to the patient to produce the desired effect.

Alternatively or in addition, it is contemplated that biliverdin reductase can be induced, expressed, and/or administered to a patient in situations where it is deemed desirable to increase bilirubin levels in the patient. The biliverdin reductase protein can be delivered to a patient, for example, in liposomes. Further, the present invention contemplates that increased levels of biliverdin reductase can be generated in a patient via gene transfer. An appropriate gene therapy vector (e.g., plasmid, adenovirus, adeno-associated virus (AAV), lentivirus, or any of the other gene therapy vectors mentioned herein) that encodes biliverdin reductase, with the coding sequence operably linked to an appropriate expression control sequence, would be administered to the patient orally, via inhalation, or by injection at a location appropriate for treatment of a condition described herein. In one embodiment of the present invention, a vector that encodes biliverdin reductase is administered to an organ affected by a condition described herein and biliverdin is subsequently or simultaneously administered to the organ, such that the biliverdin reductase breaks down the biliverdin to produce bilirubin in the organ.

Iron and Ferritin

The release of free iron by the action of HO-1 on heme stimulates the induction of apoferritin, which rapidly sequesters the iron to form ferritin. The present invention includes inducing or expressing ferritin in a patient to treat inflammation or ischemia or cell proliferation associated with various diseases or conditions in the patient. Ferritin can be induced in a patient by any method known in the art. For example, ferritin can be induced by administering iron dextran to the patient. As another example, ferritin levels in a patient can be increased by exposing the patient to ultraviolet radiation (Otterbein et al., Am. J. Physiol. Lung Cell Mol. Physiol. 279: L1029-L1037, 2000).

A "pharmaceutical composition comprising an inducer of ferritin" means a pharmaceutical composition containing any agent capable of inducing ferritin, e.g., heme, iron, and/or iron dextran, in a patient. Typically, a pharmaceutical composition comprising an inducer of ferritin is administered to a patient in aqueous or solid form. Inducers of ferritin, e.g., iron or iron dextran, useful in the methods of the invention can be obtained from any commercial source, e.g., a commercial source that supplies chemicals for medical or laboratory use.

An effective amount of an inducer of ferritin, e.g., iron or iron dextran, is an amount that is effective for treating a disease or condition. Effective doses of iron dextran can be administered once or several times per day, and each dose can fall within the range of about 1 to 1000 mg/kg, e.g., at least 2, 2.5, 5, 10, 20, 30, 40, 50, 60, 70, 80, 90, 100, 200, 250, 300, 400, 500, 600, 700, 800, or 900 mg/kg. Preferred ranges for iron dextran include 10 to 900 mg/kg, 100 to 800 mg/kg, 300 to 700 mg/kg, or 400 to 600 mg/kg. Free iron can be delivered to the patient, for example, as one or multiple doses of a commercially available iron supplement, e.g., a tablet containing iron.

Further, the present invention contemplates that increased levels of ferritin, e.g., H-chain ferritin, can be generated in a patient via gene transfer. An appropriate gene therapy vector (as described herein) would be administered to the patient orally or by injection or implantation at a location appropriate for treatment of a condition described herein. Further, exogenous ferritin can be directly administered to a patient by any method known in the art. Exogenous ferritin can be directly administered in addition to, or as an alternative to the induction or expression of ferritin in the patient as described herein. The ferritin protein can be delivered to a patient, for example, in liposomes, and/or as a fusion protein, e.g., as a TAT-fusion protein (see, e.g., Becker-Hapak et al., Methods 24:247-256, 2001).

Alternatively or in addition, it is contemplated that other iron-binding molecules can be administered to the patient to create or enhance the desired effect, e.g., to reduce free iron levels. As one example, the present invention contemplates that apoferritin can be administered to a patient, as well as any type of iron chelator, e.g., desferoxamine (DFO) or salicylaldehyde isonicotinoyl hydrazone (SIH) (see, e.g., Blaha et al., Blood 91(11):4368-4372, 1998) to create or enhance the desired effect.

Effective doses of DFO can be administered once or several times per day, and each dose can fall within the range of from about 0.1 to 1000 mg/kg, e.g., at least 2, 2.5, 5, 10, 20, 30, 40, 50, 60, 70, 80, 90, 100, 200, 250, 300, 400, 500, 600, 700, 800, or 900 mg/kg. Preferred ranges for DFO include 0.5 to 800 mg/kg, 1 to 600 mg/kg, 2 to 400 mg/kg, or 2.5 to 250 mg/kg.

Effective doses of SIH can be administered once or several times per day, and each dose can fall within the range of from about 0.02 to 100 mmol/kg, e.g., 0.02 to 50 mmol/kg, or 0.2 to 20 mmol/kg.

Effective doses of apoferritin can be administered once or several times per day, and each dose can fall within the range of about 1 to 1000 mg/kg, e.g., at least 2, 2.5, 5, 10, 20, 30, 40, 50, 60, 70, 80, 90, 100, 200, 250, 300, 400, 500, 600, 700, 800, or 900 mg/kg. Preferred ranges include 10 to 500 mg/kg, 20 to 200 mg/kg, and 25 to 150 mg/kg.

The skilled practitioner will recognize that any of the above, e.g., iron chelators, e.g., DFO or SIH, iron dextran, and apoferritin, can be administered as a single dose, in multiple doses, e.g., several doses per day, or by constant infusion. Further any of the above can be administered continuously, and for as long as necessary to produce the desired effect. Further, the skilled practitioner will recognize that any of the above can be administered in amounts outside the ranges given, depending upon the application.

Carbon Monoxide

The term "carbon monoxide" (or "CO") as used herein describes molecular carbon monoxide in its gaseous state, compressed into liquid form, or dissolved in aqueous solution. An effective amount of carbon monoxide for use in the present invention is an amount that is effective for treating a disease or condition. For gases, effective amounts of carbon monoxide generally fall within the range of about 0.0000001% to about 0.3% by weight, e.g., 0.0001% to about 0.25% by weight, preferably at least about 0.001%, e.g., 0.005%, 0.010%, 0.02%, 0.025%, 0.03%, 0.04%, 0.05%, 0.06%, 0.08%, 0.10%, 0.15%, 0.20%, 0.22%, or 0.24% by weight of carbon monoxide. For liquid solutions of CO, effective amounts generally fall within the range of about 0.0001 to about 0.0044 g CO/100 g liquid, e.g., 0.0001, 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. A skilled practitioner will appreciate that amounts outside of these ranges can be used depending upon the application.

A carbon monoxide composition can be a gaseous carbon monoxide composition. Compressed or pressurized gas useful in the methods of the invention can be obtained from any commercial source, and in any type of vessel appropriate for storing compressed gas. For example, compressed or pressurized gases can be obtained from any source that supplies compressed gases, such as oxygen, for medical use. The pressurized gas including carbon monoxide used in the methods of the present invention can be provided such that all gases of the desired final composition (e.g., CO, He, NO, $CO_2$, $O_2$, $N_2$) are in the same vessel. Optionally, the methods of the present invention can be performed using multiple vessels containing individual gases. For example, a single vessel can be provided that contains carbon monoxide, with or without other gases, the contents of which can be optionally mixed with the contents of other vessels, e.g., vessels containing oxygen, nitrogen, carbon dioxide, compressed air, or any other suitable gas or mixtures thereof.

Gaseous carbon monoxide compositions administered to a patient according to the present invention typically contain 0% to about 79% by weight nitrogen, about 21% to about 100% by weight oxygen and about 0.0000001% to about 0.3% by weight (corresponding to about 1 ppb or 0.001 ppm to about 3,000 ppm) carbon monoxide. Preferably, the amount of nitrogen in the gaseous composition is about 79% by weight, the amount of oxygen is about 21% by weight and the amount of carbon monoxide is about 0.0001% to about 0.25% by weight, preferably at least about 0.001%, e.g., 0.005%, 0.010%, 0.02%, 0.025%, 0.03%, 0.04%, 0.05%, 0.06%, 0.08%, 0.10%, 0.15%, 0.20%, 0.22%, or 0.24% by weight of carbon monoxide. It is noted that gaseous carbon monoxide compositions having concentrations of carbon monoxide greater than 0.3% (such as 1% or greater) can be used for short periods (e.g., one or a few breaths), depending upon the application.

A gaseous carbon monoxide composition can be used to create an atmosphere that comprises carbon monoxide gas. An atmosphere that includes appropriate levels of carbon monoxide gas can be created, for example, by providing a vessel containing a pressurized gas comprising carbon monoxide gas, and releasing the pressurized gas from the vessel into a chamber or space to form an atmosphere that includes the carbon monoxide gas inside the chamber or space. Alternatively, the gases can be released into an apparatus that culminates in a breathing mask or breathing tube, thereby creating an atmosphere comprising carbon monoxide gas in the breathing mask or breathing tube, ensuring the patient is the only person in the room exposed to significant levels of carbon monoxide.

Carbon monoxide levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026-2032, 1982; Ingi et al., Neuron 16:835-842, 1996). Sub-parts per million carbon monoxide levels can be detected by, e.g., gas chromatography and radioisotope counting. Further, it is known in the art that carbon monoxide levels in the sub-ppm range can be measured in biological tissue by a midinfrared gas sensor (see, e.g., Morimoto et al., Am. J. Physiol. Heart. Circ. Physiol 280:H482-H488, 2001). Carbon monoxide sensors and gas detection devices are widely available from many commercial sources.

A pharmaceutical composition comprising carbon monoxide can also be a liquid composition. A liquid can be made into a pharmaceutical composition comprising carbon monoxide by any method known in the art for causing gases to become dissolved in liquids. For example, the liquid can be placed in a so-called "$CO_2$ incubator" and exposed to a continuous flow of carbon monoxide, preferably balanced with carbon dioxide, until a desired concentration of carbon monoxide is reached in the liquid. As another example, carbon monoxide gas can be "bubbled" directly into the liquid until the desired concentration of carbon monoxide in the liquid is reached. The amount of carbon monoxide that can be dissolved in a given aqueous solution increases with decreasing temperature. As still another example, an appropriate liquid can be passed through tubing that allows gas diffusion, where the tubing runs through an atmosphere comprising carbon monoxide (e.g., utilizing a device such as an extracorporeal membrane oxygenator). The carbon monoxide diffuses into the liquid to create a liquid carbon monoxide composition.

The liquid can be any liquid known to those of skill in the art to be suitable for administration to patients (see, for example, Oxford Textbook of Surgery, Morris and Malt, Eds., Oxford University Press, 1994). In general, the liquid will be an aqueous solution. Examples of solutions include Phosphate Buffered Saline (PBS), Celsior™, Perfadex™, Collins solution, citrate solution, and University of Wisconsin (UW) solution (Oxford Textbook of Surgery, Morris and Malt, Eds., Oxford University Press, 1994).

The present invention contemplates that compounds that release CO into the body after administration of the compound (e.g., CO-releasing compounds, e.g., photoactivatable CO-releasing compounds), e.g., dimanganese decacarbonyl, tricarbonyldichlororuthenium (II) dimer, and methylene chloride (e.g., at a dose of between 400 to 600 mg/kg, e.g., about 500 mg/kg), can also be used in the methods of the present invention, as can carboxyhemoglobin and CO-donating hemoglobin substitutes. Agents capable of delivering doses of CO gas or liquid can also be utilized (e.g., CO releasing gums, creams, ointments or patches)

Any suitable liquid can be saturated to a set concentration of carbon monoxide via gas diffusers. Alternatively, premade solutions that have been quality controlled to contain set levels of carbon monoxide can be used. Accurate control of dose can be achieved via measurements with a gas permeable, liquid impermeable membrane connected to a carbon monoxide analyzer. Solutions can be saturated to desired effective concentrations and maintained at these levels.

A patient can be treated with a carbon monoxide composition by any method known in the art of administering gases and/or liquids to patients. The present invention contemplates the systemic administration of liquid or gaseous carbon monoxide compositions to patients (e.g., by inhalation and/or ingestion), and the topical administration of the compositions to the patient's organs, e.g., the gastrointestinal tract.

Gaseous carbon monoxide compositions are typically administered by inhalation through the mouth or nasal passages to the lungs, where the carbon monoxide can exert its effect directly or be readily absorbed into the patient's bloodstream. The concentration of active compound (CO) utilized in the therapeutic gaseous composition will depend on absorption, distribution, inactivation, and excretion (generally, through respiration) rates of the carbon monoxide as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed invention. Acute, sub-acute and chronic administration of carbon monoxide are contemplated by the present invention, depending upon, e.g., the severity or persistence of disease or condition in the patient. Carbon monoxide can be delivered to the patient for a time (including indefinitely) sufficient to treat the condition and exert the intended pharmacological or biological effect.

Examples of methods and devices that can be utilized to administer gaseous pharmaceutical compositions comprising carbon monoxide to patients include ventilators, face masks and tents, portable inhalers, intravenous artificial lungs (see, e.g., Hattler et al., Artif. Organs 18(11):806-812, 1994; and Golob et al., ASAIO J., 47(5):432-437, 2001), and normobaric chambers, as described in further detail below.

The present invention further contemplates that aqueous solutions comprising carbon monoxide can be created for systemic delivery to a patient, e.g., by oral delivery to a patient.

Alternatively or in addition, carbon monoxide compositions can be applied directly to the organs of a patient. For example, carbon monoxide compositions can be applied to the interior and/or exterior of the entire gastrointestinal tract, or to any portion thereof, by any method known in the art for insufflating gases into a patient. For example, gases, e.g., carbon dioxide, are often insufflated into the gastrointestinal tract and the abdominal cavity of patients to facilitate examination during endoscopic and laproscopic procedures, respectively (see, e.g., Oxford Textbook of Surgery, Morris and Malt, Eds., Oxford University Press, 1994). The skilled practitioner will appreciate that similar procedures could be used to administer carbon monoxide compositions directly to the gastrointestinal tract of a patient.

Aqueous carbon monoxide compositions can also be administered directly to the organs of a patient. Aqueous forms of the compositions can be administered by any method known in the art for administering liquids to patients. For example, the aqueous form can be administered orally, e.g., by causing the patient to ingest an encapsulated or unencapsulated dose of the aqueous carbon monoxide composition. As another example, liquids, e.g., saline solutions, can be injected into the gastrointestinal tract and the abdominal cavity of patients during endoscopic and laparoscopic procedures, respectively. The skilled practitioner will appreciate that similar procedures could be used to admister liquid carbon monoxide compositions directly to the organs of a patient.

Combination Therapy

The present invention contemplates that any of the treatments described herein, e.g., induction/expression/administration of HO-1 and/or ferritin, and the administration of CO, bilirubin, and/or biliverdin, can be used individually or in any combination in surgical procedures and to treat the disorders or conditions described herein. Further, the present invention contemplates that in any treatment regimen using any combination of the herein-described treatments, the treatments can be administered simultaneously on a single or multiple occasions, and/or individually at varying points in time, e.g., at different phases of a disease or condition. For example, a patient can receive both bilirubin and iron, or both of those plus CO, or bilirubin plus ferritin, or two or more inducers of HO-1.

Treatment of Patients with Pharmaceutical Compositions of the Present Invention

A patient can be treated with pharmaceutical compositions described herein by any method known in the art of administering liquids, solids, and/or gases to a patient.

Systemic Deliver of Pharmaceutical Compositions

Aqueous and Solid Pharmaceutical Compositions

The present invention contemplates that aqueous pharmaceutical compositions can be created for systemic delivery to a patient by injection into the body, e.g., intravenously, intraarterially, intraperitoneally, and/or subcutaneously. Aqueous pharmaceutical compositions can also be prepared for oral delivery, e.g., in encapsulated or unencapsulated form, to be absorbed in any portion of the gastrointestinal tract, e.g., the stomach or small intestine. Similarly, solid pharmaceutical compositions can be created for systemic delivery to a patient, e.g., in the form of a powder or an ingestible capsule.

Aqueous and solid pharmaceutical compositions typically include the active ingredient and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral and/or rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, e.g., sugars, polyalcohols such as mannitol or sorbitol, or sodium chloride can be included in the composition. Prolonged absorption of the injectable compositions can be brought about by including in the composition an agent which delays absorption, for example, aluminum monostearate and gelatin. Microbeads, microspheres, or any other physiologically-acceptable methods, e.g., encapsulation, can be used to delay release or absorption of the active ingredients.

Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying, and freeze-drying that yield a powder of the active ingredient plus any additional desired ingredient from a previously sterile-filtered solution thereof.

Oral compositions, which can be aqueous or solid, generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel™, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The active ingredients can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies specific for viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Gaseous Pharmaceutical Compositions

Gaseous pharmaceutical compositions, e.g., pharmaceutical compositions containing carbon monoxide, can be delivered systemically to a patient by inhalation-through the mouth or nasal passages to the lungs. The following methods and apparatus for administering carbon monoxide compositions are illustrative of useful systemic delivery methods for the gaseous pharmaceutical compositions described herein.

Ventilators

Medical grade carbon monoxide (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with house air in a blender to a desired concentration in ppm (parts per million). The patient will inhale the gas mixture through a ventilator, which will be set to a flow rate based on patient comfort and needs. This is determined by pulmonary graphics (i.e., respiratory rate, tidal volumes etc.). Fail-safe mechanism(s) to prevent the patient from unnecessarily receiving greater than desired amounts of carbon monoxide can be designed into the delivery system. The patient's carbon monoxide level can be monitored by studying (1) carboxyhemoglobin (COHb), which can be measured in venous blood, and (2) exhaled carbon monoxide collected from a side port of the ventilator. Carbon monoxide exposure can be adjusted based upon the patient's health status and on the basis of the markers. If necessary, carbon monoxide can be washed out of the patient by switching to 100% $O_2$ inhalation. Carbon monoxide is not metabolized; thus, whatever is inhaled will ultimately be exhaled except for a very small percentage that is converted to $CO_2$. Carbon monoxide can also be mixed with any level of $O_2$ to provide therapeutic delivery of carbon monoxide without consequential hypoxic conditions.

Face Mask and Tent

A carbon monoxide containing gas mixture is prepared as above to allow passive inhalation by the patient using a facemask or tent. The concentration inhaled can be changed and can be washed out by simply switching over to 100% $O_2$. Monitoring of carbon monoxide levels would occur at or near the mask or tent with a fail-safe mechanism that would prevent too high of a concentration of carbon monoxide from being inhaled.

Portable Inhaler

Compressed carbon monoxide can be packaged into a portable inhaler device and inhaled in a metered dose, for example, to permit intermittent treatment of a recipient who is not in a hospital setting. Different concentrations of carbon monoxide could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for carbon monoxide delivery. The catheter, when implanted, resides in one of the large veins and would be able to deliver carbon monoxide at given concentrations either for systemic delivery or at a local site. The delivery can be a local delivery of a high concentration of carbon monoxide for a short period of time at the site of the procedure, e.g., in proximity to the small intestine (this high concentration would rapidly be diluted out in the bloodstream), or a relatively longer exposure to a lower concentration of carbon monoxide (see, e.g., Hattler et al., Artif. Organs 18(11):806-812, 1994; and Golob et al., ASAIO J., 47(5):432-437, 2001).

Normobaric Chamber

In certain instances, it would be desirable to expose the whole patient to carbon monoxide. The patient would be inside an airtight chamber that would be flooded with carbon monoxide (at a level that does not endanger the patient, or at a level that poses an acceptable risk, or for non-human donors or brain-dead donors, at any desired level) without the risk of bystanders being exposed. Upon completion of the exposure, the chamber could be flushed with air (e.g., 21% $O_2$, 79% $N_2$) and samples could be analyzed by carbon monoxide analyzers to ensure no carbon monoxide remains before allowing the patient to exit the exposure system.

Topical Delivery of Pharmaceutical Compositions

Alternatively or in addition, pharmaceutical compositions can be applied directly to an organ, tissue, or area of the patient's body to be treated.

Aqueous and Solid Pharmaceutical Compositions

Aqueous and solid pharmaceutical compositions can also be directly applied to an organ of a patient, or to an area of the patient targeted for treatment, by any method known in the art for administering liquids or solids to patients. For example, an aqueous or solid composition can be administered orally, e.g., by causing the patient to ingest an encapsulated or unencapsulated dose of the aqueous or solid pharmaceutical composition, to treat the interior of the gastrointestinal tract or any portion thereof. Further, liquids, e.g., saline solutions, are often injected into the gastrointestinal tract and the abdominal cavity of patients during endoscopic and laparoscopic procedures, respectively. The skilled practitioner will appreciate that similar procedures could be used to administer aqueous pharmaceutical compositions directly to an organ or e.g., in the vicinity of an organ to be treated, to thereby expose the organ in situ to an aqueous pharmaceutical composition.

In the context of transplantation, in situ exposures can be performed by any method known in the art, e.g., by in situ flushing of the organ with a liquid pharmaceutical composition prior to removal from the donor (see Oxford Textbook of Surgery, Morris and Malt, Eds., Oxford University Press, 1994). Such exposures are described in further detail below.

Gaseous Pharmaceutical Compositions

A gaseous pharmaceutical composition can be directly applied to an organ of a patient, or to an area of the patient targeted for treatment, by any method known in the art for insufflating gases into a patient. For example, gases, e.g., carbon dioxide, are often insufflated into the gastrointestinal tract and the abdominal cavity of patients to facilitate examination during endoscopic and laparoscopic procedures, respectively (see, e.g., Oxford Textbook of Surgery, Morris and Malt, Eds., Oxford University Press, 1994). The skilled practitioner will appreciate that similar procedures could be used to administer gaseous pharmaceutical compositions directly to the interior of the gastrointestinal tract, or any portion thereof. Further, the skilled practitioner will appreciate that gaseous pharmaceutical compositions can be insufflated into the abdominal cavity of patients, e.g., in the vicinity of an organ to be treated, to thereby expose the organ in situ to a gaseous pharmaceutical composition.

Surgical Procedures: Transplantation

The present invention contemplates the use of the methods described herein to treat patients who undergo transplantation. The methods can be used to treat donors, recipients and/or the organ at any step of the organ harvesting, storage, and transplant process. For example, an organ can be harvested from a donor, treated with a pharmaceutical composition ex vivo in accordance with the present invention, and transplanted into a recipient. Alternatively or in addition, the organ can be treated in situ, while still in the donor (by treatment of the donor or by treating the organ). Optionally, a pharmaceutical composition can be administered to the recipient prior to, during, and/or after the surgery, e.g., after the organ is reperfused with the recipient's blood. The composition can be administered to the donor prior to or during the process of harvesting the organ from the donor.

The terms "transplantation" is used throughout the specification as a general term to describe the process of transferring an organ to a patient. The term "transplantation" is defined in the art as the transfer of living tissues or cells from a donor to a recipient, with the intention of maintaining the functional integrity of the transplanted tissue or cells in the recipient (see, e.g., *The Merck Manual*, Berkow, Fletcher, and Beers, Eds., Merck Research Laboratories, Rahway, N.J., 1992). The term includes all categories of transplants known in the art. Transplants are categorized by site and genetic relationship between donor and recipient. The term includes, e.g., autotransplantation (removal and transfer of cells or tissue from one location on a patient to the same or another location on the same patient), allotransplantation (transplantation between members of the same species), and xenotransplantation (transplantations between members of different species).

The term "donor" or "donor patient" as used herein refers to an animal (human or non-human) from whom an organ or tissue can be obtained for the purposes of storage and/or transplantation to a recipient patient. The term "recipient" or "recipient patient" refers to an animal (human or non-human) into which an organ or tissue can be transferred.

The terms "organ rejection," "transplant rejection," or "rejection" are art-recognized, and are used throughout the specification as a general term to describe the process of rejection of an organ, tissues, or cells in a recipient. Included within the definition are, for example, three main patterns of rejection that are usually identified in clinical practice: hyperacute rejection, acute rejection, and chronic rejection (see, e.g., *Oxford Textbook of Surgery*, Morris and Malt, Eds., Oxford University Press, 1994).

The term "organ(s)" is used throughout the specification as a general term to describe any anatomical part or member having a specific function in the animal. Further included within the meaning of this' term are substantial portions of organs, e.g., cohesive tissues obtained from an organ. Further still, included within the meaning of this term are portions of an organ as small as one cell of the organ. Such organs include but are not limited to kidney; liver; heart; intestine, e.g., large or small intestine; pancreas, e.g., islets; and lungs. Further included in this definition are bones, skin, and blood vessels.

Ex vivo exposure of an organ to a pharmaceutical composition can occur by exposing the organ to an atmosphere comprising a gaseous pharmaceutical composition, to a liquid pharmaceutical composition, e.g., a liquid perfusate, storage solution, or wash solution containing the pharmaceutical composition, or to both.

For example, in the context of exposing an organ to a gaseous pharmaceutical composition comprising carbon monoxide, the exposure can be performed in any chamber or area suitable for creating an atmosphere that includes appropriate levels of carbon monoxide gas. Such chambers include, for example, incubators and chambers built for the purpose of accommodating an organ in a preservation solution. An appropriate chamber can be a chamber wherein only the gases fed into the chamber are present in the internal atmosphere, such that the concentration of carbon monoxide can be established and maintained at a given concentration and purity, e.g., where the chamber is airtight. For example, a $CO_2$ incubator can be used to expose an organ to a carbon monoxide composition, wherein carbon monoxide gas is supplied in a continuous flow from a vessel that contains the gas.

As another example, in the context of exposing an organ to an aqueous pharmaceutical composition, the exposure can be performed in any chamber or space having sufficient volume for submerging the organ, completely or partially, in an aqueous pharmaceutical composition. As yet another example, the organ can be exposed by placing the organ in any suitable container, and causing a liquid pharmaceutical composition to "wash over" the organ, such that the organ is exposed to a continuous flow of the composition.

As another option, the organ can be perfused with an aqueous pharmaceutical composition. The term "perfusion" is an art-recognized term, and relates to the passage of a liquid, e.g., an aqueous pharmaceutical composition, through the blood vessels of the organ. Methods for perfusing organs ex vivo and in situ are well known in the art. An organ can be perfused with an aqueous pharmaceutical composition ex vivo, for example, by continuous hypothermic machine perfusion (see Oxford Textbook of Surgery, Morris and Malt, Eds., Oxford University Press, 1994). The aqueous pharmaceutical solution can be allowed to remain in the vasculature for a given length of time. Optionally, in in situ or ex vivo perfusions, the organ can be perfused with a wash solution, e.g., UW solution without a pharmaceutical composition, prior to perfusion with the aqueous pharmaceutical composition to remove the donor's blood from the organ. Such a process could be advantageous, for example, when using pharmaceutical compositions comprising carbon monoxide, to avoid competition for carbon monoxide by the donor's hemoglobin. As another option, the wash solution itself can be a pharmaceutical composition, e.g., a pharmaceutical composition comprising carbon monoxide.

As yet another example, in the context of pharmaceutical compositions comprising carbon monoxide, the organ can be placed, e.g., submerged, in a medium or solution that does not include carbon monoxide, and placed in a chamber such that the medium or solution can be made into a carbon monoxide composition via exposure to a carbon monoxide-containing atmosphere as described herein. As still another example, the organ can be submerged in a liquid that does not include carbon monoxide, and carbon monoxide can be "bubbled" into the liquid.

An organ can be harvested from a donor, and transplanted by any methods known to those of skill in the art (see, for example, Oxford Textbook of Surgery, Morris and Malt, Eds., Oxford University Press, 1994). The skilled practitioner will recognize that methods for transplanting and/or harvesting organs for transplantation can vary depending upon many circumstances, such as the age of the donor/recipient or the nature of the organ being transplanted.

The present invention contemplates that any or all of the above methods for exposing an organ to a pharmaceutical composition, e.g., washing, submerging, or perfusing, can be used in a given procedure, e.g., used in a single transplantation procedure.

Surgical Procedures: Balloon Angioplasty and Surgically-Induced Intimal Hyperplasia The present invention contemplates the use of the methods described herein to treat patients who undergo balloon angioplasty, or are otherwise at risk for intimal hyperplasia, e.g., due to vascular surgery. Intimal hyperplasia from vascular injury subsequent to procedures such as angioplasty, bypass surgery or organ transplantation continues to limit the success of these therapeutic interventions. The term "intimal hyperplasia" is an art-recognized term and is used herein to refer to the proliferation of cells, e.g., smooth muscle cells and/or myofibroblasts, within the intima. The skilled practitioner will appreciate that intimal hyperplasia can be caused by any number of factors, e.g., mechanical, chemical and/or immunological damage to the intima. Intimal hyperplasia can often be observed in patients, for example, following balloon angioplasty or vascular surgery, e.g., vascular surgery involving vein grafts. The term "angioplasty" is an art-recognized term and refers to any procedure involving the remodeling of an artery. Such procedures include, e.g., angioplasty using balloons ("balloon angioplasty"), lasers ("laser angioplasty"), and any other mode for performing angioplasty, e.g., using other suitable instruments, such as a microfabricated probe.

Individuals considered at risk for developing intimal hyperplasia may benefit particularly from the invention, primarily because prophylactic treatment can begin before there is any evidence of intimal hyperplasia. Individuals "at risk" include, e.g., patients that have or will undergo angioplasty, e.g., balloon angioplasty, or patients that have or will have any type of mechanical, chemical and/or immunological damage to the intima.

A patient can be treated according to the methods of the present invention before, during and/or after the surgical procedure or angioplasty. Further, if desired, vein(s) can be exposed to the pharmaceutical compositions described herein in situ and/or ex vivo, as described herein in the context of organ transplants. The vein can be exposed to a gaseous pharmaceutical composition, and/or to a liquid pharmaceutical composition, e.g., a liquid perfusate, storage solution, or wash solution having the active ingredient dissolved therein. For example, a liquid pharmaceutical composition can be instilled into an arterial segment, e.g., by retrograde perfusion, and can be allowed to remain in the segment for a given length of time.

Disorders and Conditions

The methods of the present invention can be used to treat one or more of the following inflammatory, respiratory, cardiovascular, renal, hepatobiliary, reproductive, and gastrointestinal disorders; shock; or cellular proliferative and/or differentiative disorders, or to reduce the effects of ischemia, or aid in wound healing.

Respiratory Disorders

Examples of respiratory conditions include, but are not limited to, asthma; Acute Respiratory Distress Syndrome (ARDS), e.g., ARDS caused by peritonitis, pneumonia (bacterial or viral), or trauma; idiopathic pulmonary diseases; interstitial lung diseases, e.g., Interstitial Pulmonary Fibrosis (IPF); pulmonary emboli; Chronic Obstructive Pulmonary Disease (COPD); emphysema; bronchitis; cystic fibrosis; lung cancer of any type; lung injury, e.g., hyperoxic lung injury, Primary Pulmonary Hypertension (PPH); secondary pulmonary hypertension; and sleep-related disorders, e.g., sleep apnea.

Cardiovascular Disorders

Cardiovascular disorders include disorders involving the cardiovascular system, e.g., the heart, the blood vessels, and/or the blood. A cardiovascular disorder can be caused, for example, by an imbalance in arterial pressure, a malfunction of the heart, or an occlusion of a blood vessel, e.g., by a thrombus. Examples of such disorders include congestive heart failure, peripheral vascular disease, pulmonary vascular thrombotic diseases such as pulmonary embolism, stroke, ischemia-reperfusion (I/R) injury to the heart, atherosclerosis, and heart attacks.

Renal Disorders

Disorders involving the kidney include, but are not limited to, pathologies of glomerular injury such as in situ immune complex deposition and cell-mediated immunity in glomerulonephritis; damage caused by activation of alternative complement pathway, epithelial cell injury; pathologies involving mediators of glomerular injury including cellular and soluble mediators; acute glomerulonephritis, such as acute proliferative glomerulonephritis, e.g., poststreptococcal glomerulonephritis and nonstreptococcal acute glomerulonephritis, rapidly progressive glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis) and chronic glomerulonephritis. Disorders of the kidney also include infections of the genitourinary tract.

Hepatobiliary Disorders

Disorders involving the liver include, but are not limited to, cirrhosis and infectious disorders such as viral hepatitis, including hepatitis A-E viral infection and infection by other hepatitis viruses, clinicopathologic syndromes, acute viral hepatitis, chronic viral hepatitis, and fulminant hepatitis; and drug- and toxin-induced liver disease, such as alcoholic liver disease.

Gastrointestinal Disorders

Gastrointestinal disorders include, but are not limited to, ileus (of any portion of the gastrointestinal tract, e.g., the large or small intestine); inflammatory bowel disease, e.g., specific inflammatory bowel disease, e.g., infective specific inflammatory bowel disease, e.g., amoebic or bacillary dysentery, schistosomiasis, *campylobacter* enterocolitis, *yersinia* enterocolitis, or *enterobius vermicularis*; non-infective specific inflammatory bowel disease, e.g., radiation enterocolitis, ischaemic colitis, or eosinophilic gastroenteritis; non-specific bowel disease, e.g., ulcerative colitis, indeterminate colitis, and Crohn's disease; necrotizing enterocolitis (NEC); and pancreatitis.

Cellular Proliferative and/or Differentiative Disorders

Examples of cellular proliferative and/or differentiative disorders include, but are not limited to, cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. The term "cancer" refers to cells having the capacity for autonomous growth. Examples of such cells include cells having an abnormal state or condition characterized by rapidly proliferating cell growth. The term is meant to include all types of cancerous growths, e.g., tumors, or oncogenic processes, or metastatic tissues. Also included are malignancies of the various organ systems, such as lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

Cancers which can be treated using the present compositions and methods include, for example, stomach, colon, rectal, liver, pancreatic, lung, breast, cervix uteri, corpus uteri, ovary, prostate, testis, bladder, renal, brain/central nervous system, head and neck, throat, Hodgkins disease, non-Hodgkins leukemia, skin melanoma, various sarcomas, small cell lung cancer, choriocarcinoma, mouth/pharynx, esophagus, larynx, melanoma, and kidney and lymphoma, among others.

Neurological Disorders

The methods of the present invention can also be used to treat neurological disorders. Neurological disorders include, but are not limited to disorders involving the brain, e.g., degenerative diseases affecting the cerebral cortex, including Alzheimer's disease, and degenerative diseases of basal ganglia and brain stem, including Parkinsonism and idiopathic Parkinson's disease (paralysis agitans). Further, the methods can be used to treat pain disorders.

Examples of pain disorders include, but are not limited to, pain response elicited during various forms of tissue injury, e.g., inflammation, infection, and ischemia, usually referred to as hyperalgesia (described in, for example, Fields, *Pain*, New York:McGraw-Hill, 1987); pain associated with musculoskeletal disorders, e.g., joint pain; tooth pain; headaches; pain associated with surgery; pain related to irritable bowel syndrome; or chest pain. Also included in this category are seizure disorders, e.g., epilepsy.

Inflammatory Disorders

The methods of the present invention can be used to treat inflammatory disorders. The terms "inflammatory disorder(s)" and "inflammation" are used to describe the fundamental pathological process consisting of a dynamic complex of reactions (which can be recognized based on cytologic and histologic studies) that occur in the affected blood vessels and adjacent tissues in response to an injury or abnormal stimulation caused by a physical, chemical or biologic agent, including the local reactions and resulting morphologic changes, the destruction or removal of the injurious material, and the responses that lead to repair and healing. Inflammation is characterized in some instances by the infiltration of cells immune cells such as monocytes/macrophages, natural killer cells, and/or lymphocytes (e.g., B and T lymphocytes) into the area of tissue. In addition, inflamed tissue may contain cytokines and chemokines that are produced by the cells that have infiltrated into the area. Often, inflammation is accompanied by thrombosis, including both coagulation and platelet aggregation. The term inflammation includes various types of inflammation such as acute, chronic, allergic (including conditions involving mast cells), alterative (degenerative), atrophic, catarrhal (most frequently in the respiratory tract), croupous, fibrinopurulent, fibrinous, immune, hyperplastic or proliferative, subacute, serous and serofibrinous. Inflammation localized in the gastrointestinal tract, or any portion thereof, kidneys, liver, heart, skin, spleen, brain, kidney, pulmonary tract, and the lungs is favorably treated by the methods of the present invention. Inflammation associated with shock, e.g., septic shock, hemorrhagic shock caused by any type of trauma, and anaphylactic shock is favorably treated by the methods of the present invention. Further, it is contemplated that the methods of the present invention can be used to treat rheumatoid arthritis, lupus, and other inflammatory and/or autoimmune diseases, heightened inflammatory states due to immunodeficiency, e.g., due to infection with HIV, and hypersensitivities.

Wound Healing

Based on the anti-inflammatory properties of HO-1 and heme degradation products, the present invention contemplates that the methods described herein can be used to promote wound healing (e.g., in transplanted, lacerated (e.g., due to surgery), or burned skin). They would typically be applied locally to the wound (e.g., as a wound dressing, lotion, or ointment), but could be delivered systemically as well.

Reproductive Disorders

The present invention contemplates that the methods described herein can also be used to treat or prevent certain reproductive disorders, e.g., impotence and/or inflammation associated with sexually transmitted diseases. Further, the methods of the present invention can be used to prevent premature uterine contractions, and can be used to prevent premature deliveries and menstrual cramps.

EXAMPLES

The invention is illustrated in part by the following examples, which is not to be taken as limiting the invention in any way.

Example 1

Acute Colitis

In these experiments, CoPP, biliverdin, CO, and DFO were tested in an acute colitis animal model.

Materials and Methods

Animals. Pathogen-free male C57BL/6 mice, 4-6 weeks of age (Taconic; C57BL/6×129 svj strain) were used in this example. Mice were kept for one week at 4 mice/cage and fed normal laboratory chow and drinking water ad libitum prior to the experiments. All mice weighed between 22.5 g and 27.7 g at the beginning of the trial. The animal experimentation protocol was reviewed and approved by the Animal Care and Use Committees of the Beth Israel Deaconess Medical Center.

Induction of Colitis. Colitis was induced by feeding mice 5% (wt/v) dextran sodium sulfate (DSS) (MW 40,000; ICN Biomedicals Inc., OH), dissolved in distilled water, for a period of 7 days. The resulting condition was termed "DSS-colitis." Control animals were fed distilled water ad libitum. The mortality rate in the control group and the CO-treated group was 10% (2/20) and 14% (2/14), respectively. These animals were excluded from the statistical analysis. In the other groups, no mortality occurred during 7 days of 5% DSS treatment.

Experimental Reagents and Treatment Protocol. Cobalt protoporphyrin (CoPPIX), zinc protoporphyrin (ZnPPIX, Porphyrin Products, Logan, Utah) and biliverdin dihydrochloride (ICN Biomedicals Inc., OH) were dissolved in a small amount 0.2 M NaOH, subsequently adjusted to a pH of 7.4 with 1 M HCl, and diluted in 0.9% NaCl. The stock solutions (CoPPIX and ZnPPIX=1 mg/ml, biliverdin=10 mM) were aliquoted and kept at −70° C. until used. Light exposure was limited as much as possible. CoPPIX (5 mg/kg), ZnPPIX (20 mg/kg) and biliverdin (50 μmol/kg) were administered to the mice intraperitoneally (i.p.) 24 hours before induction of DSS-colitis and daily thereafter. Desferoxamine (DFO) was prepared in imidazole buffer (50 mM imidazole, 220 mM NaCl, pH 7.4). DFO was injected subcutaneously (s.c.) twice daily (125 mg/kg) or infused i.p. (130 mg/kg/day; pumping rate 0.5 μl/hour for 8 days) by miniosmotic Alzet™ pumps (Alza Corporation, Palo Alto, Calif.) (Postma et al., Exp. Parasitol. 89(3):323-30 1998). The pumps were installed i.p. 24 hours before induction of colitis. When animals were sacrificed at day 7 of DSS treatment, the pumps were removed and evaluated to determine if DFO application had taken place.

CO gas was administrated exogenously by putting animals in a CO exposure chamber (Otterbein et al., Nat. Med. 6(4): 422-8, 2000). Briefly, CO at a concentration of 1% (10,000 parts per million (ppm)) in compressed air was mixed with balanced air (21% oxygen) in a stainless steel mixing cylinder before entering the exposure chamber. CO concentrations were controlled by varying the flow rates of CO in a mixing cylinder before delivery to the chamber. Because the flow rate is primarily determined by the $O_2$ flow, only the CO flow was changed to deliver the final concentration to the exposure chamber. A CO analyzer (Interscan Corporation, Chatsworth, Calif.) was used to measure CO levels continuously in the chamber. Mice were placed in the chamber 24 hours before the induction of the colitis and were kept in the exposure chamber during the whole period of the experiment (total of 8 days). CO concentration was maintained between 250 and 400 ppm at all times. Animals were removed daily from the chamber to assess weight and stool.

Evaluation of Symptoms of Colitis. All animals were evaluated clinically on a daily basis. The evaluation of each animal included a measurement of weight, hemoccult positivity and examination of stool for the presence of gross blood and stool consistency. The disease activity index (DAI) was calculated by scoring percent weight loss, intestinal bleeding (no blood; occult blood=hemoccult+; gross blood) and stool consistency (normal stool=well-formed pellets; loose stool=pasty and semiformed stools; diarrhea=liquid stool that stuck to the anus) (Table 1).

TABLE 1

Scoring of the Disease Activity Index (DAI)

| Score | Weight loss | Stool consistency | Bleeding |
|---|---|---|---|
| 0 | None | Normal | Normal |
| 1 | 0-10% | | |
| 2 | 10-15% | Loose stools | Hemoccult+ |
| 3 | 15-20% | | |
| 4 | >20% | Diarrhea | Gross Bleeding |

The animals were sacrificed, and the whole colon from the colo-cecal junction to the anal verge was removed and gently cleaned of stool. The distal part of the colon was fixed in 10% formaldehyde and embedded in paraffin for staining with hematoxylin and eosin. The transverse sections were graded in blinded fashion for severity of mucosal injury on a scale of 0-4 as follows: Grade 0: intact crypt; Grade 1: loss of the basal one-third of the crypt; Grade 2: loss of the basal two-thirds of the crypt; Grade 3: loss of the entire crypt with the surface epithelium remaining intact; Grade 4: loss of both crypt and surface epithelium (erosion). In addition, the percentages of the respective injured surface areas for each tissue section were scored on a scale of 1-4 as follows: 1=1% to 25%; 2=26% to 50%; 3=51% to 75%; and 4=76% to 100%. The product of the two scores gave the crypt score for each section. The means of all sections were then calculated for each animal.

Western Blot Analysis. Tissue samples from the distal colon of the animals were removed and snap frozen with liquid nitrogen. The frozen tissue was ground thoroughly and homogenized in Ripa buffer supplemented with proteinase inhibitors. The protein concentration was determined by the Bio-Rad Dc Protein Assay™ according manufacturers instructions (Bio-Rad, Hercules, Calif.). Electrophoresis was performed under denaturing conditions according to Laemmli with 10% polyacrylamide gels by loading 35 μg protein. Proteins were transferred onto a polyvinyldifluoridine membrane (Immobilon P™; Millipore, Bedford, Mass.) by electroblotting. Proteins were then detected with rabbit polyclonal antibodies directed against human HO-1 (StressGen, Victoria, Canada) or β-tubulin (Boehringer Mannheim, Mannheim, Germany). Proteins were visualized using HRP-conjugated donkey anti-rabbit IgG or goat anti-mouse IgG (Pierce) and the ECL assay (Amersham Life Science, Arlington Heights, Ill.), according to manufacturer's instructions.

Semi-Quantitative PCR. RNA was extracted using RNeasy Mini Kits (Qiagen Inc., CA, USA) and reverse transcribed into cDNA with the RNA PCR Kit (TaKaRa, PanVera, Madison, Wis., USA). A total of 2 μl of cDNA was amplified in a 50 μl reaction mix containing 10 μM dNTPs, 50 pg of 5'-prime and 3'-prime oligos, 2.5 U of LA-Taq polymerase (TaKaRa) and MgCl2, specific to each primer pair used. The primers for murine and human HO1 (372 bp) (5': TGA AGG AGG CCA CCA AGG AGG T (SEQ ID NO:1); 3': AGG TCA CCC AGG TAG CGG GT (SEQ ID NO:2)) and β-actin (525 bp) (5': GCC ATC CTG CGT CTG GAC CTG G(SEQ ID NO:3); 3': TAC TCC TGC TTG CTG ATC CAC A (SEQ ID NO:4)) were obtained from Life Technologies, NY, USA. PCR reactions were performed after a 4 min denaturation at 94° C. a repeating the cycle 94° C., 55° C. and 72° C. each for 1 min for number of cycles specific for each primer pair in a Peltier Thermal Cycler PTC-200 (MJ Research, Las Vegas, Nev., USA). PCR products (10-20 μl) were analyzed in an ethidium bromide-stained 1% agarose gel.

Statistical Analysis. Percent body weight loss and DAI score data were summarized as mean±standard deviation of mice untreated or treated with CoPP, ZnPP, biliverdin, CO or DFO. Significance was calculated using the Mann-Whitney test and defined as $p<0.05$. Time to occurrence of symptoms was calculated using Kaplan-Meier life tables. Differences between groups were tested using a log-rank test and the mean time to occurrence, with a 95% confidence interval reported.

Results

DSS Induces Acute Hemorrhagic Colitis and HO-1 Expression. The C57/BL6 mice exposed to 5% DSS in the drinking water showed the first clinical symptoms by days 2 and 3, with the development of loose stools and hemoccult positive stools. By days 5 to 6, most of the animals developed the complete picture of a hemorrhagic colitis with diarrhea and gross bleeding. In the control group, 2 deaths occurred (out of 20 subjects, 10%) before the termination of the 7-day trial. Both of these mortalities occurred on day 6. These animals were excluded from the statistical analysis.

Figure 1B:
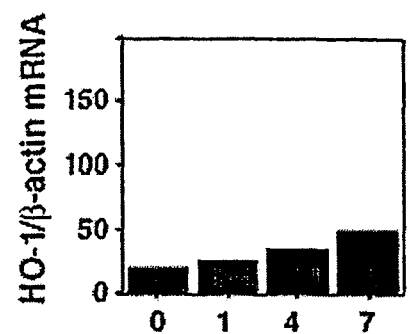
FIG. 1B is a bar graph illustrating the changing ratio of HO-1:β-actin mRNA levels after induction of DSS-colitis in control animals. X-axis: days.
Figure 1C:
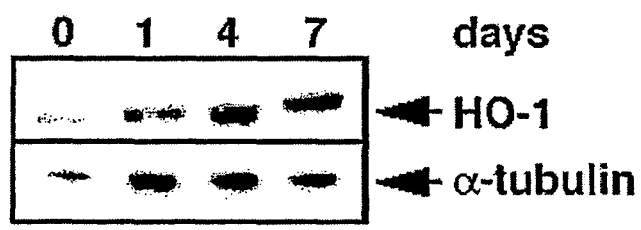
FIG. 1C is a photograph of a Western blot showing an increase in HO-1 protein levels after induction of DSS-colitis in control animals. α-tubulin was used as a internal reference.

Induction of DSS-colitis leads to a marked elevated level of HO-1 mRNA over time (FIGS. 1A-1B). An elevated level of HO-1 protein expression was also observed (FIG. 1C). After only 24 hours, a slight increase in HO-1 protein level was visible; it thereafter increased consistently to maximum levels at 7 days.

Treatment with CoPP Induces HO-1 in the Intestinal Tissue. Daily administration of CoPP (5 mg/kg) i.p. (starting 24 hours before exposing the animals to DSS via the drinking water) induced HO-1 in the colonic tissue of the animals. The CoPP-treated animals showed consistently high levels of HO-1 protein in the intestine over the entire 7 day period of the experiment, whereas non-treated animals exhibited slowly increasing HO-1 levels that reached a maximum at day 7 (FIGS. 2A and 2B versus FIGS. 1A and 1B). The level of HO-1 in the non-treated animals at day 7 was below the level of HO-1 observed in the CoPP-treated animals.

Figure 2A:
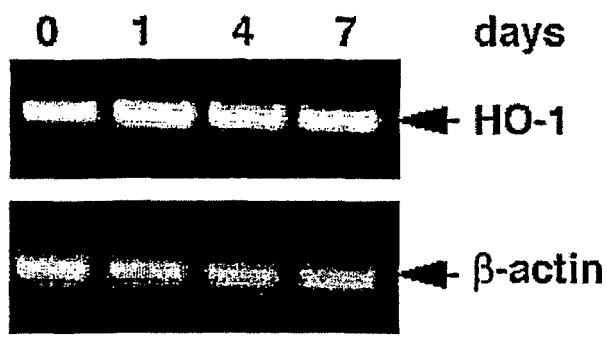
FIG. 2A is a photograph of a gel showing the results of semi-quantitative PCR analysis of HO-1 and β-actin mRNA levels after induction of DSS-colitis in animals treated with cobalt protoporphyrin (CoPP).
Figure 2B:
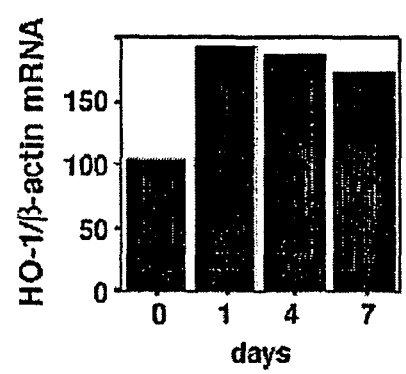
FIG. 2B is a bar graph illustrating the changing ratio of HO-1:β-actin mRNA levels after induction of DSS-colitis in animals treated with CoPP.
Figure 2C:
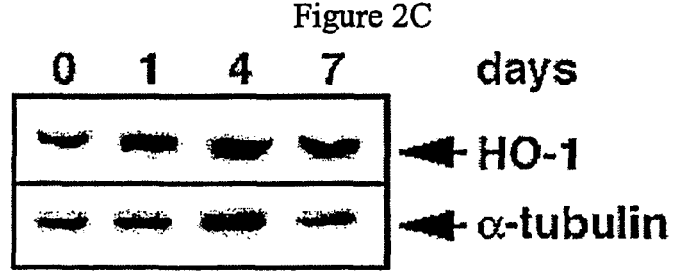
FIG. 2C is a photograph of a Western blot showing an increase in HO-1 protein levels after induction of DSS-colitis in animals treated with CoPP. α-tubulin was used as a loading control.
Figure 3A:
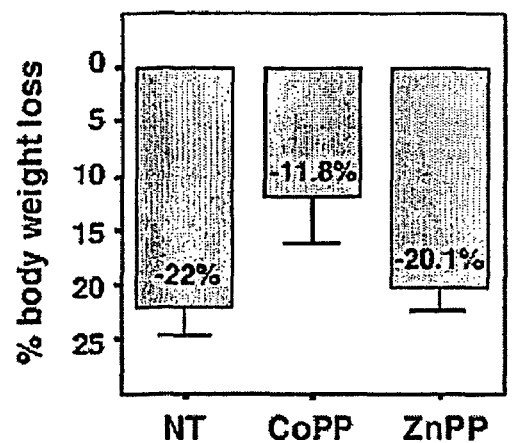
FIG. 3A is a bar graph that illustrates the effect of cobalt protoporphyrin treatment on weight loss associated with DSS-colitis, as observed on day 7 of the experiment. NT=no treatment; CoPP=cobalt protoporphyrin; ZNPP=zinc protoporphyrin.
Figure 3B:
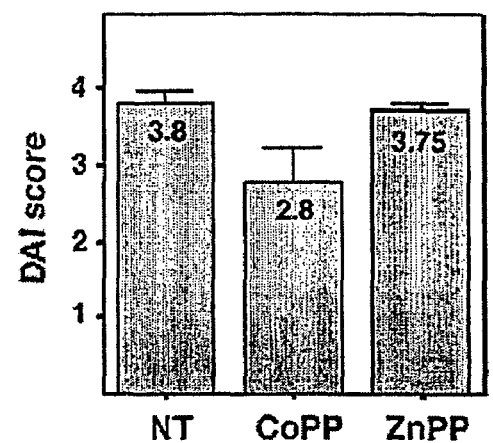
FIG. 3B is a bar graph that illustrates the effect of cobalt protoporphyrin treatment on the DSS-colitis disease activity index (DAI), as observed on day 7 of the experiment.
Figure 3C:
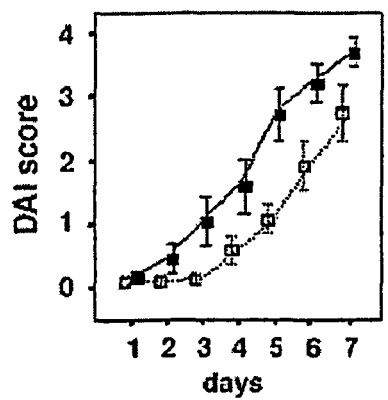
FIG. 3C is a line graph that illustrates the effect of cobalt protoporphyrin treatment on the DSS-colitis DAI over a period of 7 days.
Figure 3D:
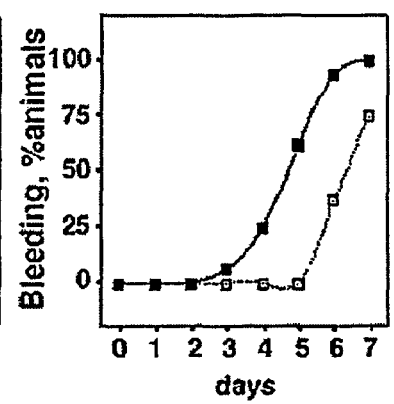
FIG. 3D is a line graph that illustrates the effect of cobalt treatment on intestinal bleeding associated with DSS-colitis over a period of 7 days.
Figure 3E:
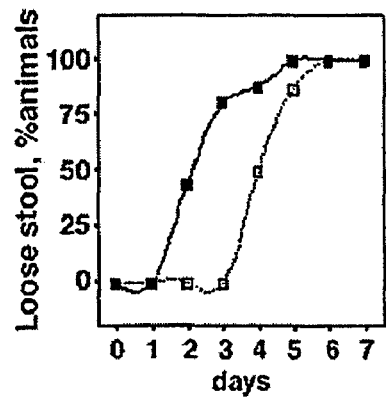
FIG. 3E is a line graph that illustrates the effect of cobalt protoporphyrin induction of HO-1 on stool abnormalities associated with DSS-colitis over a period of 7 days.

HO-1 Induction Ameliorates DSS-Colitis and Reduces Associated Colonic Lesions. The constant induction of HO-1 by CoPP treatment ameliorated DSS-colitis as observed clinically and morphologically. At day 7, the mean total percent body weight loss was significantly lower in the CoPP-treated group (n=12) as compared to the non-treatment group (n=20) (−11.8% versus −22%; $p<0.001$; FIG. 3A). Further, the DAI, which factors in weight loss, stool consistency, and intestinal bleeding, showed a significant difference between the two groups (2.8 with CoPP-treatment and 3.8 in non-treated animals, $p<0.001$; see FIG. 3B). During the course of disease development, a significant difference in the DAI between CoPP-treated and untreated groups was observed beginning on day 2 (difference in DAI=0.4, $p<0.05$). Maximum protection conferred by CoPP occurred at day 5 (difference in DAI=1.64; $p<0.001$). Toward the end of the 7 days, the difference had lessened (difference in DAI=1.04; $p<0.001$; FIG. 3C). The time required for animals to develop symptoms, e.g., occurrence of loose stool and gross intestinal bleeding, was prolonged significantly in the group in which HO-1 was induced with CoPP ($p<0.02$ and $p<0.005$, respectively; FIGS. 3D and 3E). Animals treated with CoPP developed loose stool at a mean of 4.6 days (95% confidence interval: 4.1 to 5.1 days) as compared to non-treated animals, which developed loose stool at 3 days (95% confidence interval 2.4 to 3.6 days). Bleeding was observed in CoPP-treated animals after a mean of 6.9 days (95% confidence interval: 6.3 to 7.4 days) as compared 5.1 days for non-treated animals (95% confidence interval: 4.6 to 5.6 days). A control group treated with zinc protoporphyrin (ZnPP), a blocker of HO-1 enzymatic activity, showed no significant changes in the natural course of DSS colitis as compared to untreated animals (FIGS. 2A-2B). Thus, it appears that the protective effect of CoPP is based on the specific induction of HO-1 by this compound.

Figure 4A:
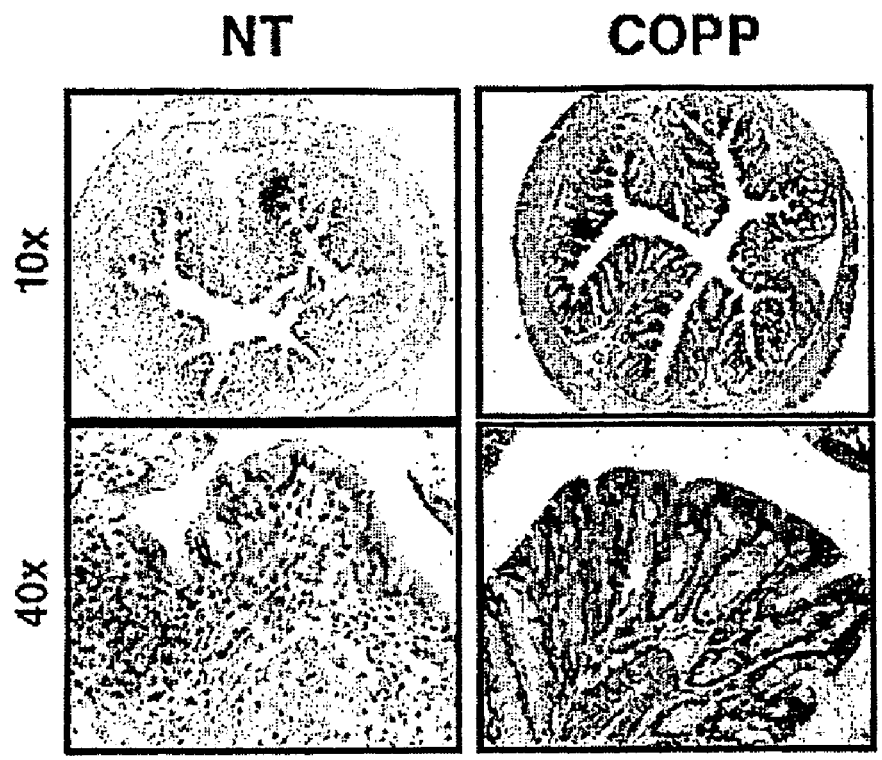
FIG. 4A is a set of four photomicrographs of cryptal structures at 10× (top row) and 40× (bottom row) magnification in untreated control animals (NT, left column) and CoPP-treated animals (COPP, right column).
Figure 4B:
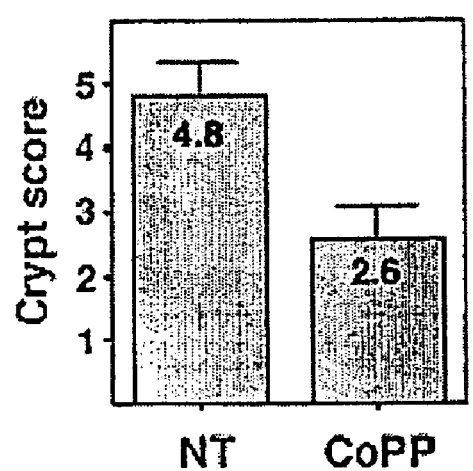
FIG. 4B is a bar graph illustrating the relatively decreased damage to mucosal glands in animals treated with CoPP as compared to untreated controls, as measured by crypt scores.

Histologically, the animals with DSS-colitis alone showed progressive loss of the cryptal structure, which led to complete destruction of the mucosal glands by day 7 (FIG. 4A). Mixed inflammatory infiltration consisting of mainly macrophages and neutrophils and some lymphocytes appeared in the lamina propria and submucosa. Sporadically, crypt abscess and erosions of the surface epithelium were observed (FIG. 4A). In contrast, CoPP treatment samples showed remaining cryptal structures and intact epithelial surface, although increasing separation between the base of the crypt and muscularis mucosa, along with mild inflammatory infiltrate, was observed at day 7 as well (FIG. 4A). Evaluation of the colonic damage revealed that the CoPP group had a significantly lower crypt score in comparison to the non-treatment group (2.6 versus 4.8; p<0.05), which indicates less extensive and severe destruction of the mucosal glands (FIG. 4B). The clinical disease activity supported by the pathologic changes showed a significantly better course and outcome of the CoPP treated animals.

Exogenously Applied Biliverdin Ameliorates DSS-Colitis. The protective effects of biliverdin/bilirubin, iron/ferritin, and CO against DSS-colitis were investigated. In the first group (n=12), daily treatment with biliverdin injected i.p. was found to be protective against DSS-colitis. Percent weight loss (FIG. 5A) and the DAI (FIG. 5B) were significantly reduced after 7 days as compared to control animals (percent weight loss: 16.5% versus 22%; DAI score 3.3 versus 3.8; p<0.01). As with CoPP treatments, the time to the development of symptoms (e.g., loose stool and gross intestinal bleeding) was prolonged significantly (p<0.01 and p<0.05, respectively) (FIGS. 5D and 5E). Animals treated with biliverdin developed loose stool at a mean of 4.4 days (95% confidence interval: 4 to 4.9 days) as compared to non-treated animals at 3 days (95% confidence interval: 2.4 to 3.6 days). Bleeding occurred in biliverdin-treated animals after a mean of 6.2 days (95% confidence interval: 5.4 to 6.9 days) as compared to non-treated animals, which exhibited bleeding at 5.1 days (95% confidence interval: 4.6 to 5.6 days).

Figure 6A:
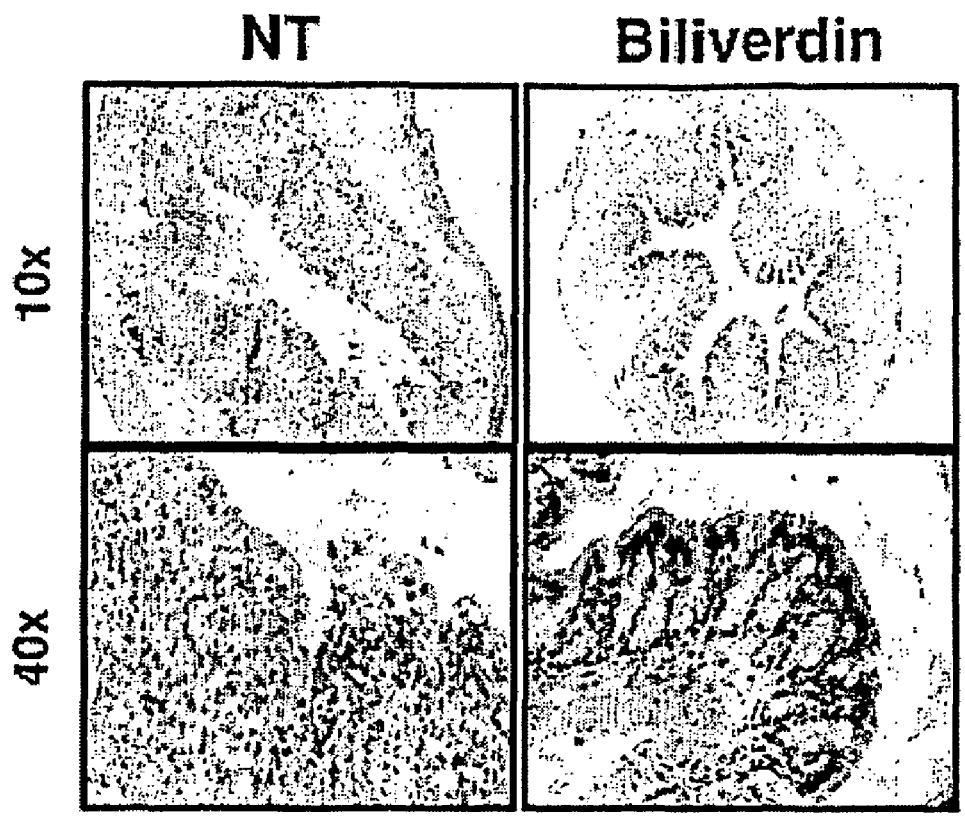
FIG. 6A is a set of four photomicrographs of cryptal structures at 10× (top row) and 40× (bottom row) magnification in untreated control animals (NT, left column) and biliverdin-treated animals (right column).
Figure 6B:
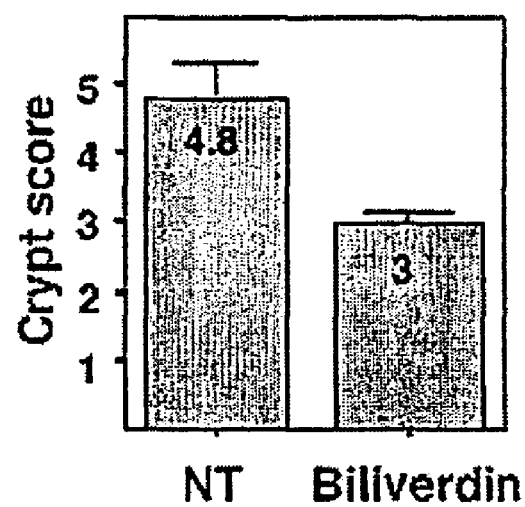
FIG. 6B is a bar graph illustrating the relatively decreased damage to mucosal glands in animals treated with biliverdin as compared to untreated controls, as measured by crypt scores.

Using light microscopy, it was observed that the biliverdin treatment group had a preserved cryptal structure (FIG. 6A). The crypt score was also significantly better in comparison to the non-treatment group (3 versus 4.8; p<0.05; FIG. 6B). Overall, biliverdin did not mediate protection to the same extent as CoPP/HO-1, but the difference between the effects of CoPP/HO-1 and biliverdin did not reach significance.

The continuous exposure of animals to 200-400 ppm CO (200 ppm, n=6; 400 ppm, n=6) did not have an effect compared to the control (FIGS. 5A-B).

DFO, an iron chelator, was used to assess the potential function of endogenous ferritin. Subcutaneous injections of 125 mg/kg DFO (n=4) administered twice daily to animals showed no protective effect. Further, intraperitoneally-placed osmotic pumps (n=4) were also used. The pumps delivered 130 mg/kg/d DFO at a constant pumping rate of 0.5 µl/hour. While this dose has previously been proven to efficiently remove endogenous iron from mice (Postma et al., Exp. Parasitol. 89(3):323-30, 1998), no protective effect was observed (FIGS. 5A-5B).

Conclusions

These results indicate that upregulation of HO-1, e.g., by administration of CoPP or biliverdin, alone or in combination with CO, is useful in the treatment of colonic inflammation, e.g., colitis and associated colonic lesions.

Example 2

Cardiac Transplantation

In these experiments, CoPP, biliverdin, and CO were tested in a cardiac transplantation mouse model.

Materials and Methods

Animals. Male DBA/2 (H-$2^d$), B6AF1 (H-$2^{k/d,b}$) and FVB (H-$2^q$) mice were purchased from Jackson Lab. Inc. (Bar Harbor, Me.). They were maintained in the institutional specific-pathogen free facility, which has an appropriate light cycle with free access to water and chow ad libitum, and used for experiments at age of 6-10 weeks.

Cardiac transplantation. DBA2/J and B6AF1 mice were used as donor and recipient, respectively. Heterotopic heart transplantation was carried out according to the procedure of Corry and Russell (Corry et al., Transplant Proc. 5(1):733-5, 1973). In brief, the heart was excised from donor mice after ligation of the pulmonary vein, and the inferior and superior vena cavas. Under a microscope, the graft aorta and pulmonary artery were anastomosed to the recipient's abdominal aorta and inferior vena cava, respectively. Secondary heart grafting into the neck was performed using a cuff technique as described previously (Matsuura et al., Transplantation 51(4): 896-8, 1991). Briefly, the heart graft was harvested from either DBA2/J (donor strain) or FVB (third-party strain) mice. The right jugular vein and the right common carotid artery of recipient were dissected, and a cuff (polyethylene or polyimide) was connected to these vessels. The graft aorta and pulmonary artery were sleeved over the cuff on the recipient's common carotid artery and the jugular vein, respectively, and fixed with a ligature. After transplantation, beating of the graft was monitored by daily palpation, and scored +1 to +4 according to the strength of graft contractions. Graft rejection was defined as cessation of beating, and was confirmed by direct inspection followed by histological examination.

Cells and Culture Medium. Primary murine leukocytes were isolated by mincing the spleen followed by osmotic lysis of red blood cells. T cells were further enriched by passing through a nylon-wool mesh column, and purified using the MACS Pan T cell isolation kit (Miltenyi Biotec Inc., Auburn, Calif.) according to the manufacture's instructions. Purity of CD3+ T cells was more than 95%, as determined by flow cytometry. The Jurkat cell line was maintained in RPMI 1640 culture media (Bio Whittaker Inc., Walkersville, Md.) supplemented with 2 mM 1-glutamine, 100 U/ml penicillin, 100 µg/ml streptomycin, and 10% fetal calf serum. For murine primary cell culture, 2-ME (50 µM) was also added to the media.

Experimental Reagents and Treatment Protocol. Cobalt protoporphyrin (CoPPIX), zinc protoporphyrin (ZnPPIX, Porphyrin Products, Logan, Utah) and biliverdin dihydrochloride (ICN Biomedicals Inc., OH) were dissolved in a small amount 0.2 M NaOH, subsequently adjusted to a pH of 7.4 with 1 M HCl, and diluted in 0.9% NaCl. The stock solutions (CoPPIX and ZnPPIX=1 mg/ml, biliverdin=10 mM) were aliquoted and kept at −70° C. until used. Light exposure was limited as much as possible.

Donor and recipient mice were treated either with CoPPIX (5 mg/kg/day), ZnPPIX (5 mg/kg/day) or biliverdin (administered once, twice or three times per day at a dose of 50 µmol/kg/dose). All reagents were administered by intraperitoneal (i.p.) injection. Donor animals were treated for 2 days, starting from 2 days before graft harvest (day-2 and day-1). Treatment of recipient mice was initiated one day before transplantation, and continued until 13 days post-transplant (day-1 to day 13). For the experiments using donor splenocyte infusion (DSI) on day-7 (DSI (D-7)), treatments of recipient animals (either with CoPPIX or ZnPPIX) started from day-8 and were terminated on day 6. Recipients received no further treatment. Spleen cells ($2 \times 10^7$) isolated from DBA/2J mice as described herein were used for DSI treatment. The cells were injected via the penile vein with 200 µl of 0.9% saline solution.

Bilirubin assay. Biliverdin at 50 µmol/kg was injected i.p. into B6AF1 mice. Blood was drawn before and 15, 30, 60, 120, 240, and 360 minutes after biliverdin injection. Serum was collected by centrifugation of blood samples, and the total bilirubin level was measured using a total bilirubin assay kit (Sigma Aldrich, St. Louis, Mo.). Measurement of total bilirubin was performed according to the kit protocol, and was duplicated for each sample. This experiment was repeated four times.

Con A and anti-CD3 mAb mediated proliferation assay. B6AF1 splenocytes or purified T cells were prepared according to the herein-described method and used as responder cells. Responders ($2.5 \times 10^5$/well) were stimulated with either Con A (1 µg/ml) or anti-CD3 mAb (1 µg/ml) and cultured in a 96 well round bottom plates. Purified T cells ($5 \times 10^4$/well) were cultured in anti-CD3 mAb (10 µg/ml) coated 96 well flat bottom plates in the presence of anti-CD28 mAb (1 µg/ml). Cells were cultured with or without biliverdin (at various concentrations) for 48 hours at 37° C., 95% air with 5% $CO_2$. They were pulsed with $^3$H-thymidine (1 µCi/well) 16 hours before termination of cell culture and $^3$H-thymidine incorporation was measured by using a β-counter. These proliferation assays were performed in triplicate and were repeated 3 times.

Mixed lymphocyte culture (MLC). Irradiated (25Gy, $^{137}$Cs) DBA/2 splenocytes ($5 \times 10^5$/well) were co-cultured with responders ($5 \times 10^5$/well) in a 96 well round bottom plates for 3 days at 37° C., 95% air with 5% $CO_2$. When using cells from cardiac recipients as responders, the co-culture period was 3 days without any further in vitro treatment. $^3$H-thymidine (1 µCi/well) was added 16 hours before termination of cell culture, and $^3$H-thymidine incorporation was measured.

IL-2 assay. B6AF1 leukocytes ($2.5 \times 10^5$ cells/well) were stimulated by anti-CD3 mAb (1 µg/ml), and cultured in 96 well round bottom plates with or without biliverdin (50 or 100 µM). Forty-eight hours later, culture supernatant (100 µl) was collected and stored at −80° C. until use. All cultures were performed in triplicates. IL-2 levels in the supernatants were measured by enzyme-linked immunosorbent assays (ELISA) using an IL-2 assay kit (Quantikine® M, R&D Systems, Inc), following kit instructions. Measurements of each supernatant sample for IL-2 were performed in duplicate. The experiment was repeated 4 times.

Flow cytometric analysis (IL-2R expression). B6AF1 leukocytes ($5 \times 10^5$ cells/well) were stimulated with anti-CD3 mAb (1 µg/ml) and cultured in 96 well round bottom plates with or without biliverdin (100 µM). Six and 24 hours after stimulation, cells were harvested, washed, and stained with fluorochrome conjugated isotype control Abs, or specific anti-CD4 and/or anti-CD25 mAbs (all antibodies obtained from BD Pharmingen). Non-stimulated naïve leukocytes were used as a negative control. Following Abs staining, cell samples were analyzed using a FACSort™ flow cytometer and CellQuest™ software (BD Biosciences, Palo Alto, Calif.). Ten thousand CD4+ T cells were acquired for each sample and their CD25 expression was examined. The experiment was repeated 3 times.

HO activity assay. DBA/2J mice were given either no treatment or CoPPIX or ZnPPIX at a dose of 5 mg/kg, i.p. (n=10 per group). One day after the treatment, the animals were sacrificed, the spleen and the heart were excised, and tissue samples were frozen at −80° C. Frozen tissue samples were homogenized in ice-cold sucrose and Tris-HCl buffer. The microsomal pellet was obtained after centrifugation and re-suspended in $MgCl_2$-potassium phosphate buffer. Sample protein was then incubated with the reaction mixture containing rat liver cytosol, hemin, glucose-6-phosphate, glucose-6-phosphate dehydrogenase and NADPH (Sigma-Aldrich Corporation, St. Louis, Mo.) for 60 minutes at 37° C. The generated bilirubin was measured by reacting with diazotized surfanilic acid to yield azobilirubin using spectrophotometer.

Protein extraction and Western blot. DBA/2 mice were injected i.p. with CoPPIX at a dose of 5 mg/kg. Non-treated animals served as naïve controls. One, 2, 4, and 7 days following treatment, the heart and the spleen were excised from the animals, and samples were snap-frozen in liquid nitrogen. Protein extracts were prepared from the obtained tissues, electrophoresed under denaturing conditions (10% polyacrylamide gels) and transferred onto polyvinyldifluoridine membranes (Immobilon™ P, Millipore, Bedford, Mass.). HO-1 was detected using the rabbit anti-human HO-1 polyclonal antibody (Stress Gen Biotechnologies Corp., Victoria, Canada); α-actin was detected using the goat anti-mouse α-actin mAb (1A4, Sigma-Aldrich Corporation). Primary antibodies were detected using horseradish peroxidase conjugated donkey anti-rabbit or goat anti-mouse IgG secondary antibodies (Pierce, Rockford, Ill.). Protein was visualized using the Enhanced Chemi Luminescence (ECL™) Assay kit (Amersham Life Science Inc., Arlington Heights, Ill.), according to the manufacturer's instructions, and stored in the form of photo radiographs (Biomax™ MS, Eastman Kodak, Rochester, N.Y.). The amount of HO-1 expression was normalized with α-actin expression, and was quantified by using the ImageQuant™ software (Molecular Dynamics, Sunny Vale, Calif.).

Nuclear protein extraction and electrophoretic mobility shift assay (EMSA). Jurkat T cells were cultured in 10% FCS supplemented RPMI 1640 with 50 nM phorbol myristyl acetate (PMA) and 2 µM ionomycin (both reagents from ICN Biomedicals) in the presence or absence of 100 µM biliverdin. Following 0, 2, and 4 hrs of stimulation, cells ($30 \times 10^6$ cells for each group at each time points) were collected, washed twice with PBS, and pelleted. Nuclear and cytoplasmic extracts were prepared according to a modified Shapiro's method (Shapiro et al., DNA 7(1):47-55, 1988). Protein concentrations were determined by the Bradford assay. The following oligonucleotides (Invitrogen, Calsbad, Calif.) were used for EMSA:

NFAT, (coding) 5'-GCCCACAGAGGAAAATTTGTTTCA TACAG-3' (SEQ ID NO:5),
(non-coding) 5'-CTGTATGAAACAAATTTTCCTCTGTC-CGC-3' (SEQ ID NO:6); and
NF-κB, (coding) 5'-AGCTTAGAGGGGACTTTCCGA GAGGA-3' (SEQ ID NO:7),
(non-coding) 5'-TCCTCTCGGAAAGTC-CCCTCTAA GCT-3' (SEQ ID NO:8).

Oligonucleotides were radioactively labeled with [$^{32}$P] ATP. The EMSA reactions were assembled as previously described (Usheva et al., Proc. Natl. Acad. Sci. USA 93(24):13571-6, 1996). Digital images from the EMSA radiographs were obtained using an image scanner.

Statistics. Cardiac graft survival was plotted by the Kaplan-Meier method, and a log-rank test was applied to compare statistical significance. Expression levels of HO-1/α-actin protein are expressed as mean±standard deviation. Other data are expressed as mean±standard error of the mean (mean±SEM). Intergroup statistical analysis was performed by one-way ANOVA, and Fisher's PSLD was used for a post-hoc test. A comparison was considered statistically significant when the p-value was <0.05.

Results

Figure 7A:
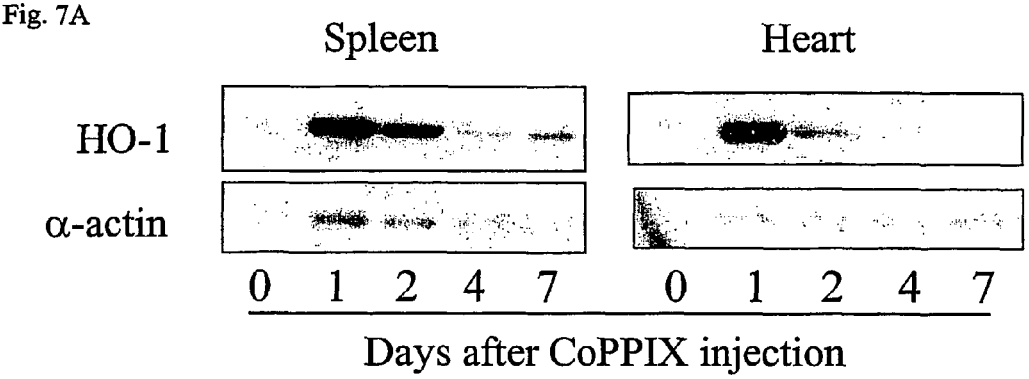
FIG. 7A is a set of photographs showing the results of Western blot analysis of HO-1 (top row) and α-actin (bottom row) protein expression in spleen (left column) and heart (right column) at 0, 1, 2, 4, and 7 days after CoPPIX administration.
Figure 7B:
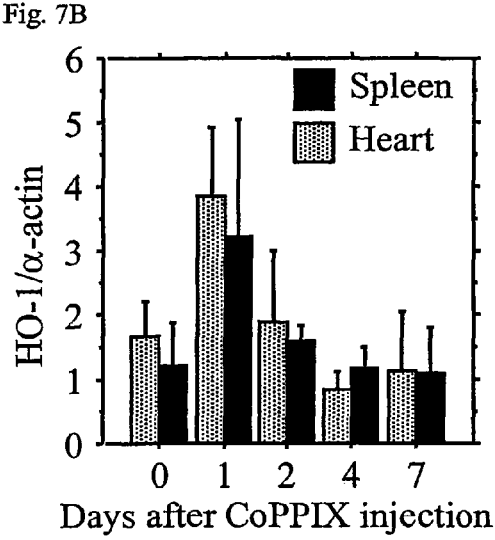
FIG. 7B is a bar graph illustrating the increase in HO-1 expression levels at 0, 1, 2, 4, and 7 days after CoPPIX administration.
Figure 7C:
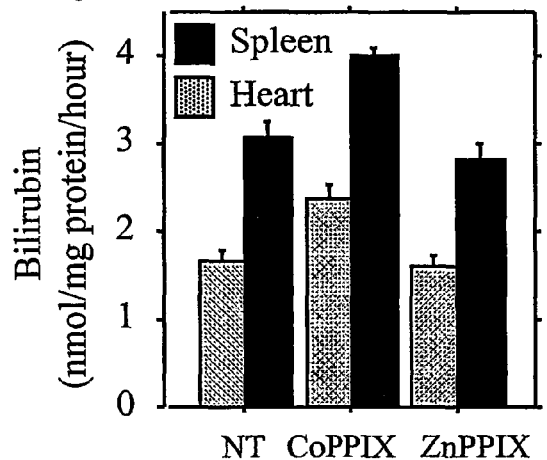
FIG. 7C is a bar graph illustrating the effect of treatment with CoPPIX or ZnPPIX on bilirubin levels.
Figure 7D:
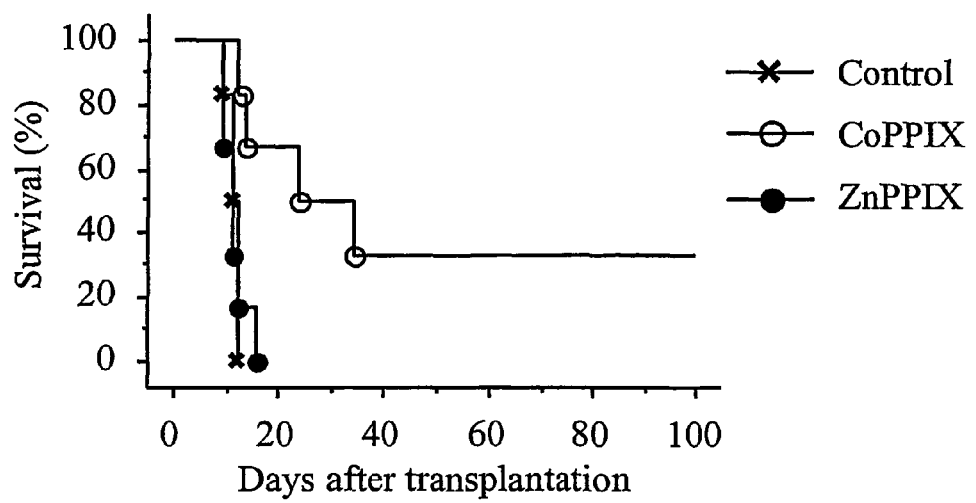
FIG. 7D is a line graph illustrating the percent survival of cardiac allografts in animals treated with CoPPIX or ZnPPIX.

Induction of HO-1 expression and enzymatic function prolongs cardiac allograft survival. As is shown in FIGS. 7A-7C, administration of CoPPIX up-regulated HO-1 protein expression in the heart and spleen of adult mice. Maximal HO-1 expression was detected one day after CoPPIX injection (FIG. 7A). HO-1 enzymatic activity was also significantly enhanced by CoPPIX, while this was not the case for ZnPPIX, which is known to inhibit HO-1 function (FIG. 1B). Based on these data, the effect of induction of enzymatically active HO-1 expression by CoPPIX on cardiac allograft rejection was evaluated. ZnPPIX was used as a control reagent. Both CoPPIX and ZnPPIX were administered daily to the donor from day-2 and to the recipient from day-1 to day 13 post-transplant. Untreated B6AF1 recipients rejected DBA/2 cardiac allografts at a median survival time (MST) of 11.5 days (FIG. 7D). Induction of HO-1 expression by CoPPIX administration resulted in a significant prolongation of graft survival (p<0.005 versus control). Two of 6 grafts (33.3%) survived long-term, i.e., >100 days, while the MST of the other 4 rejected grafts was 18 days. In contrast, administration of ZnPPIX did not result in prolongation of graft survival as compared to untreated controls; these grafts were rejected promptly with a MST of 11 days.

Figure 8A:
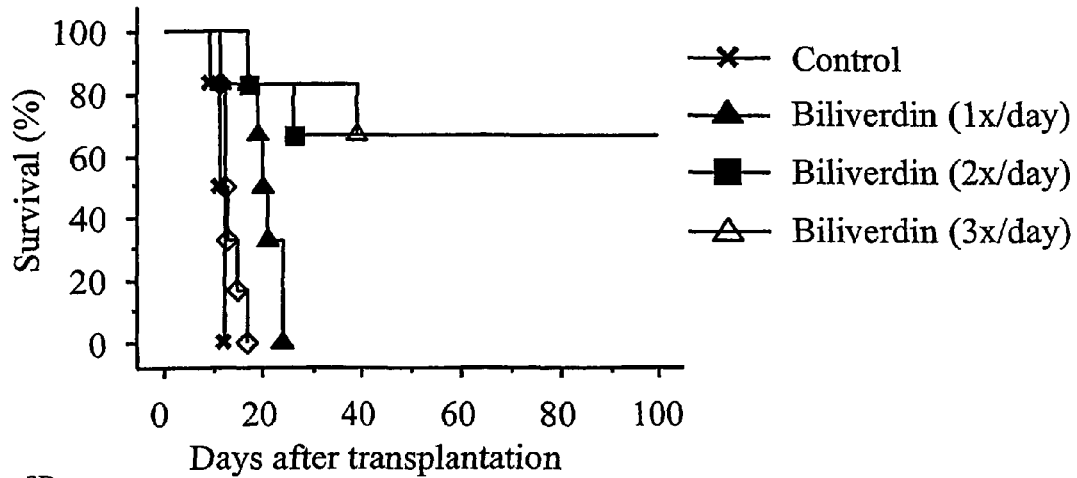
FIG. 8A is a line graph illustrating the % survival of cardiac allografts in animals treated with biliverdin on three different dosage schedules.
Figure 8B:
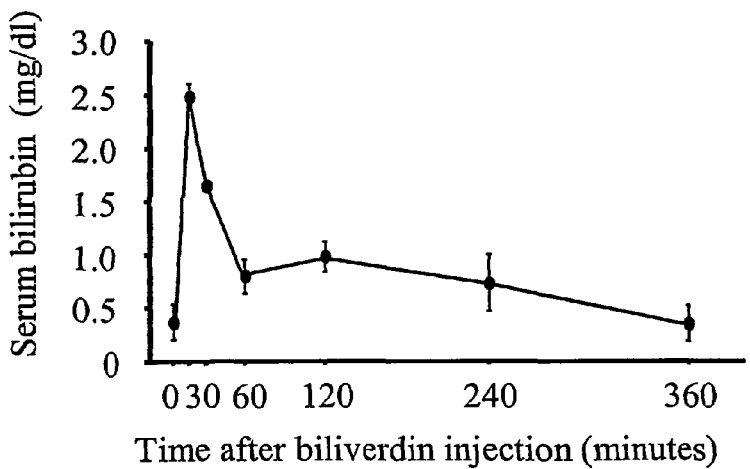
FIG. 8B is a line graph illustrating the increase in serum bilirubin levels with time after administration of biliverdin.
Figure 8C:
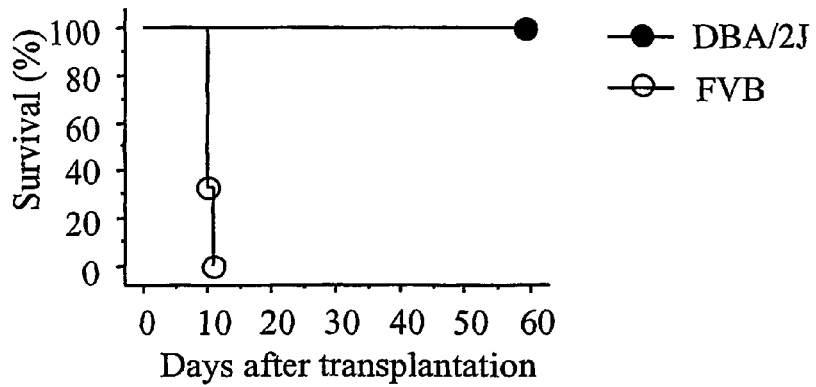
FIG. 8C is a line graph illustrating percent survival in mice challenged by second set transplantation using cardiac allografts from donor (DBA/2J) or third party (FVB) mouse strain.

Biliverdin induces donor specific tolerance to cardiac allograft. As is shown in FIGS. 8A-8C, administration of biliverdin (50 μmol/kg) using the same treatment schedule as CoPPIX, i.e., one dose per day, prolonged graft MST to 20.5 days (p<0.01 when compared to control) (FIG. 8A). To determine the approximate half-life of exogenously administered biliverdin, serum bilirubin level was analyzed after a single 50 μmol/kg injection. Upon administration of biliverdin, serum bilirubin levels peaked rapidly to reach a maximal level at 15 minutes with a return to basal levels 4 to 6 hours thereafter (FIG. 8B). We thus tested the effects of administering biliverdin two (every 12 hours) or three (every 8 hours) times per day at 50 μmol/kg per dose. These two treatment schedules significantly increased graft survival, with 4 of 6 (66.7%) grafts surviving for more than 100 days (both p<0.001 versus control, FIG. 2A). These recipients who accepted the allografts for long-term by biliverdin treatment were challenged by second set transplantation using cardiac allografts from either the donor (DBA2/J) or third party (FVB) strain mouse (n=3 for each strain). As shown in the FIG. 8C, the recipients harboring the initial graft accepted the secondary heart graft from the donor strain for more than 60 days, whereas they rejected third party graft within 11 days. These data suggest that administration of biliverdin is capable of inducing tolerance in the MHC class I plus class II mismatched mouse heart transplantation.

Figure 9:
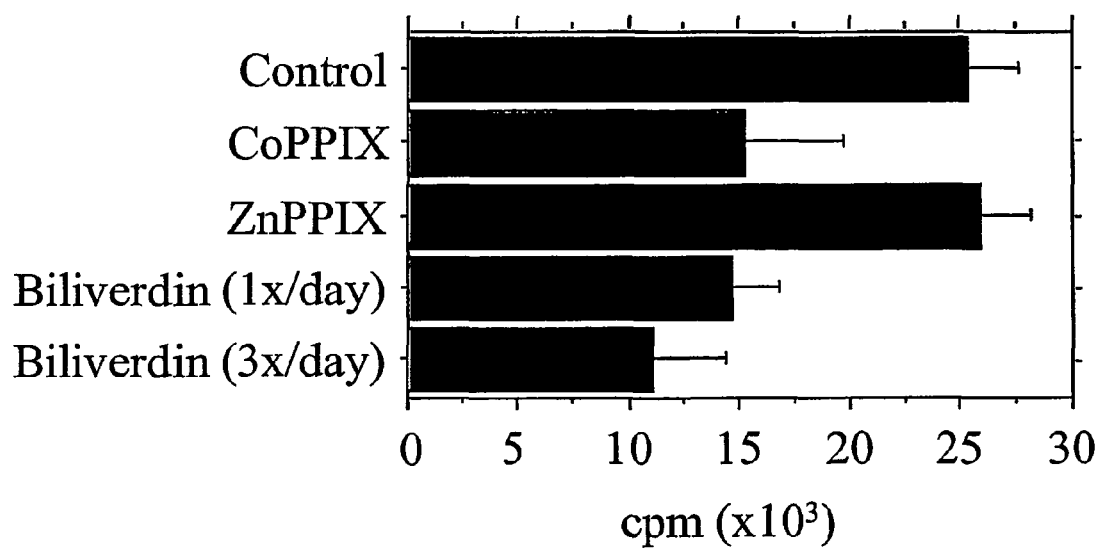
FIG. 9 is a bar graph illustrating the effect on proliferation of splenocytes in animals treated with CoPPIX, ZnPPIX, or biliverdin (1×/day or 3×/day).

Induction of HO-1 expression or biliverdin administration suppresses the T cell mediated alloimmune response in vivo. As shown in FIG. 9, the immune response of cardiac allograft recipients under different treatments, i.e., no treatment (n=4), CoPPIX (n=4), ZnPPIX (n=4) or biliverdin (50 μmol/kg/lx daily and 50 μmol/kg/3× daily; n=4 for each group) was assessed. Recipient splenocytes harvested 5 days after cardiac transplantation were used as responder cells in an in vitro culture with DBA/2 splenocytes as feeder cells. Proliferation was measured at 72 hours (FIG. 9). HO-1 induction by CoPPIX in vivo inhibited splenocyte proliferation in a significant manner, as compared to controls (p<0.05), whereas ZnPPIX administration did not. The proliferation of the splenocytes from biliverdin-treated recipients was significantly suppressed, both in recipients receiving one and in those receiving three doses of biliverdin per day, when compared to the control (p<0.01).

Figure 10A:
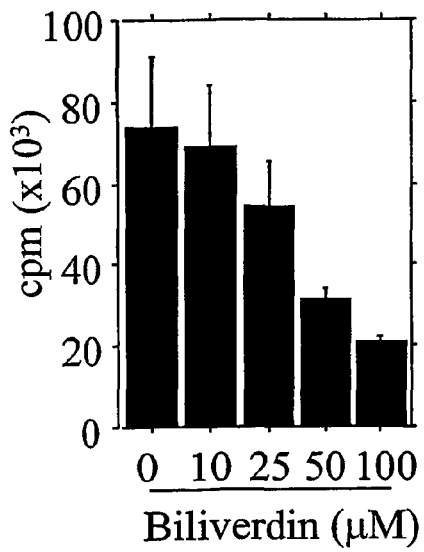
FIG. 10A is a bar graph illustrating the effect of different doses of biliverdin on proliferation of splenocytes stimulated with ConA.
Figure 10B:
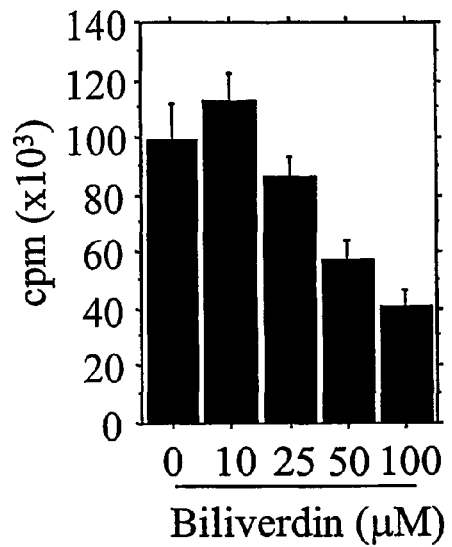
FIG. 10B is a bar graph illustrating the effect of different doses of biliverdin on proliferation of splenocytes stimulated with anti-CD3 mAb.
Figure 10C:
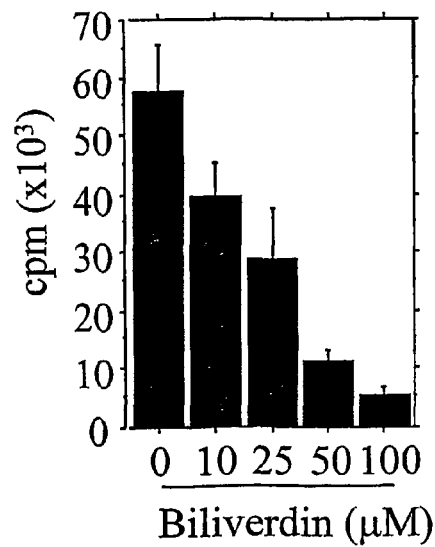
FIG. 10C is a bar graph illustrating the effect of different doses of biliverdin on proliferation of splenocytes stimulated with irradiated DBA/2 splenocytes.
Figure 10D:
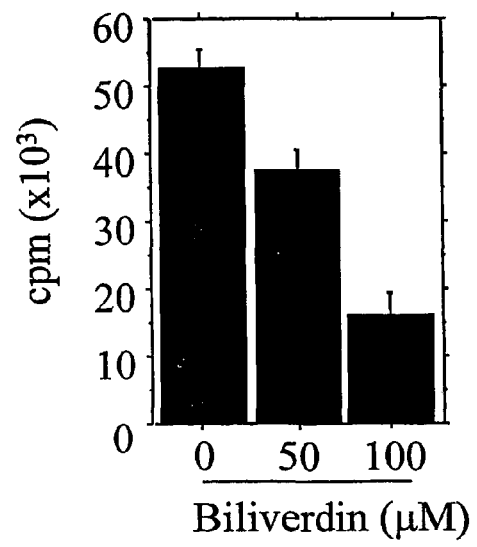
FIG. 10D is a bar graph illustrating the effect of different doses of biliverdin on proliferation of splenocytes co-stimulated with anti-CD3 mAb plus anti-CD28.

Biliverdin suppresses T cell proliferation in vitro. To assess whether biliverdin has a suppressive effect on T cell proliferation in vitro, naïve B6AF1 splenocytes were stimulated with ConA, anti-CD3 mAb or irradiated DBA/2 splenocytes in the presence or absence of biliverdin. Biliverdin suppressed leukocyte proliferation in all cases in a dose-dependent manner (FIGS. 10A-10C). A significant suppressive effect was achieved at concentrations of 50 μM and 100 μM for ConA or anti-CD3 mAb driven T cell proliferation and at 10 μM in the case of alloantigen mediated T cell activation (FIG. 10C). Further, the suppressive effect of biliverdin appeared to act directly on T cells in that proliferation of purified B6AF1 mouse T cells (purity over 95%) in response to anti-CD3 mAb plus anti-CD28 mAb co-stimulation, a combination shown to stimulate T cells in an antigen presenting cell independent manner, was also suppressed by biliverdin (FIG. 10D).

Biliverdin suppresses IL-2 production by blockade of nuclear translocation of NFAT and NF-κB in T cells. IL-2 production by splenocytes following anti-CD3 mAb stimulation was significantly suppressed in a dose-dependent manner by biliverdin treatment in vitro (FIG. 11A). Addition of exogenous recombinant IL-2 (50 U/ml) into culture wells 6 or 24 hours after biliverdin treatment overcame the suppressive effect of biliverdin (FIG. 11B). Moreover, biliverdin at a concentration of 100 μM did not affect the expression of the IL-2 receptor α-chain (IL-2Rα, CD25) of anti-CD3 mAb stimulated splenic CD4+ T cells. Representative results are shown after 6 hours of culture compared to the non-treatment control (FIG. 11C); similar results were seen after 24 hours. As one theory, not meant to be limiting, biliverdin may exert its effect on T cells by interfering directly with the signal transduction pathway leading to IL-2 synthesis, but not by down-regulation of IL-2Rα surface expression or blocking the signaling pathways involved in IL-2 driven proliferation.

To investigate whether the activation of transcription factors involved in IL-2 transcription/expression, i.e., NF-κB and NFAT, were modulated by biliverdin, Jurkat T cells were stimulated by the combination of PMA and ionomycin. The level of nuclear translocation of NF-κB and NFAT was examined by measuring DNA-binding activity of nuclear extracts by EMSA. PMA plus ionomycin stimulation induced the activation of NF-κB and NFAT nuclear translocation and DNA binding, as assessed 2 and 4 hours after stimulation, respectively. Biliverdin inhibited DNA binding of both NF-κB and NFAT (FIG. 11D), suggesting that it suppresses IL-2 production via inhibition of its transcription, possibly by blocking NFAT and NF-κB activation.

Figure 12A:
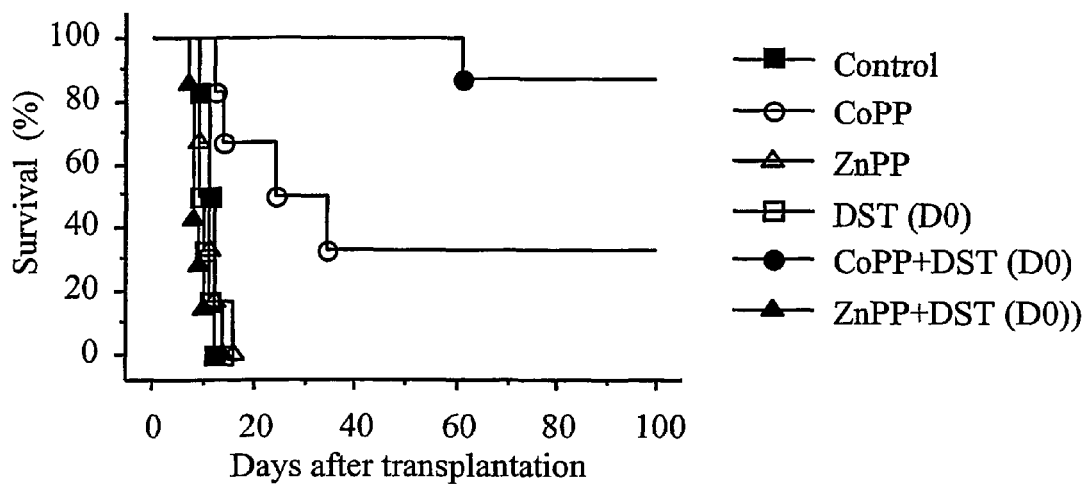
FIG. 12A is a line graph illustrating percent graft survival in animals treated with CoPP or ZnPP alone (donor treated on day-2 (D-2) and day-1 (D-1), recipient treated from day-1 (D-1) to day +13 (D13)), DSI alone (recipient treated at day 0 (D0)), or CoPP or ZnPP (donor treated on D-2 and D-1, recipient treated from D-1 to D13) plus DSI (recipient treated at D0).

Induction of HO-1 by CoPP cooperates with donor splenocyte infusion (DSI) to achieve long-term acceptance of cardiac allografts. When DSI was given to a B6AF1 recipient immediately after transplantation (day 0), a DBA/2J heart allograft was rejected promptly, similar to the untreated control (FIG. 12A). Induction of HO-1 expression by CoPPIX administration to the donor from day-2 and to the recipient from day-1 to day 13 post-transplant together with DSI (D0) significantly (p<0.001) prolonged graft survival (7 of 8 (87.5%) survived long-term for more than 100 days) when compared to DSI (D0) or CoPPIX treatment alone. Conversely, treatment with ZnPPIX plus DSI (D0) had no significant graft prolongation effect as compared to the control or DSI (D0) alone. These data suggest that induction of HO-1 expression helps to achieve long-term allograft survival.

Figure 12B:
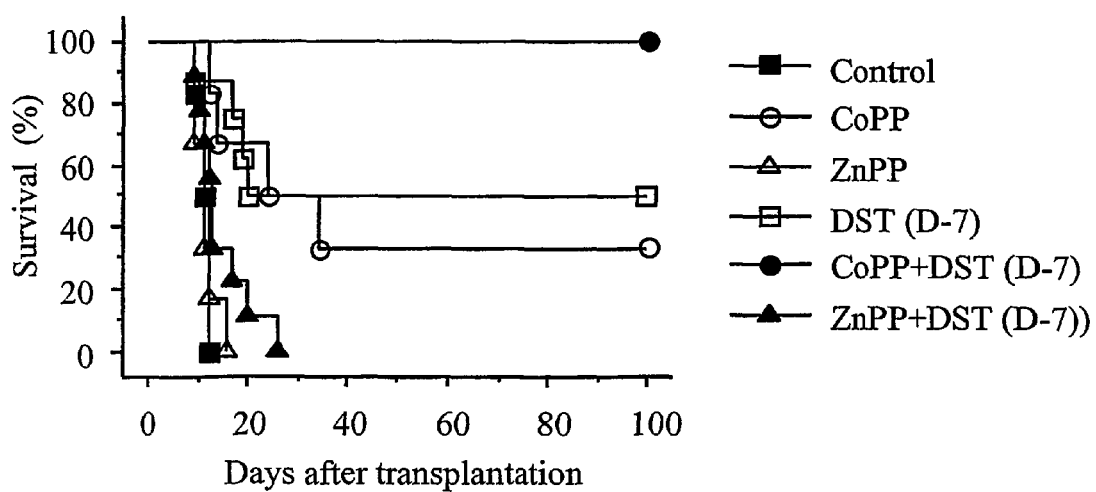
FIG. 12B is a line graph illustrating percent graft survival in animals treated with CoPP or ZnPP alone (donor treated on day-2 (D-2) and day-1 (D-1), recipient treated from day-8 (D-8) to day +6 (D6)), DST alone (recipient treated at D-7), or CoPP or ZnPP (donor treated for D-2 and D-1, recipient treated from D-8 to D6) plus DSI (recipient treated at day-7 (D-7)).

Enzymatic activity of HO-1 is essential for donor splenocyte infusion (DSI) mediated long-term allograft acceptance. DSI alone given 7 days before heart grafting (D-7) led 50% (4/8) of the allografts to survive for more than 100 days (FIG. 12B). The induction of HO-1 expression by administration of CoPPIX to the donor for 2 days (day-1 and day-2) and to the recipient from day-8 (one day before DSI) to day 6 plus DSI (D-7) allowed all of the cardiac allografts (100%, 7/7) to survive over 100 days. The treatment period and the dose are identical to other CoPPIX treatment protocols used in the present study. Importantly, when ZnPPIX, an inhibitor of HO-1 enzymatic activity, was administered to both donor and recipient under the same protocol used for the CoPPIX treatment as mentioned former, the graft prolongation effect of DSI (D-7) was completely abrogated such that none (0/9) of allografts underwent long-term survival (MST: 13 days). These results suggest the importance of HO-1 activity upon DSI mediated long-term allograft survival.

Conclusions

These results indicate that the administration of CoPPIX and/or biliverdin can contribute to long-term allograft survival. The effect of CoPPIX administration appears to synergize with the administration of DSI, suggesting that treatment to induce HO-1 expression, e.g., by administration of CoPPIX, in addition to DSL would further increase allograft survival.

Example 3

Over-Expression of H-Ferritin Protects Rat Livers from Ischemia Reperfusion Injury (IRI) and Prevents Hepatocellular Damage upon Transplantation into Syngeneic Recipients Expression of the ferritin heavy chain (H-ferritin) gene was evaluated for potential cytoprotective effects that could be used in a therapeutic manner, e.g., to suppress ischemia reperfusion injury (IRI) of transplanted organs.

Materials and Methods

TNF-α induced apoptosis. Primary bovine aortic endothelial cells (BAEC) or murine 2F-2B EC (ATCC) were cotransfected with β-galactosidase plus control (pcDNA3 or pcDNA3/HO-1) or pcDNA3/H-Ferritin. Apoptosis was induced by TNF-α plus Act.D and quantified.

Etoposide and serum deprivation-induced apoptosis. Murine 2F-2B cells were cotransfected with β-galactosidase plus control (pcDNA3) or pcDNA3/H-ferritin and treated with etoposide (200 µM, 8 h) or subjected to serum deprivation (0.1% FCS, 24 hours).

H-ferritin toxicity. Murine 2F-2B cells were cotransfected with β-galactosidase plus increasing amounts of pcDNA/H-ferritin (0.1-200 ng/well). As controls, pcDNA3 and pcDNA3/HO-1 were used. EC apoptosis was induced by TNF-α plus Act.D, and the apoptosis of β-galactosidase-transfected EC was quantified.

Cold ischemia in vitro model Livers were harvested from SD rats, exposed to ischemia (24 hours, 4° C., University of Wisconsin (UW) solution (Oxford Textbook of Surgery, Morris and Malt, Eds., Oxford University Press, 1994) and perfused ex vivo with syngeneic blood. Livers were transduced with recombinant adenovirus encoding H-ferritin, and controls were either non-transduced or transduced with β-galactosidase. Bile production was measured using standard methods at 30, 60, 90 and 120 minutes.

Cold ischemia in vivo orthotopic transplantation model Livers were harvested from SD rats, exposed to ischemia (24 hours, 4° C., University of Wisconsin (UW) solution (Oxford Textbook of Surgery, Morris and Malt, Eds., Oxford University Press, 1994) and perfused ex vivo with syngeneic blood. The livers were then transduced with recombinant adenovirus encoding H-ferritin (controls were either non-transduced or transduced with β-galactosidase) and transplanted into syngeneic recipients. Eight to ten animals were analyzed per group.

Results

Figure 13A:
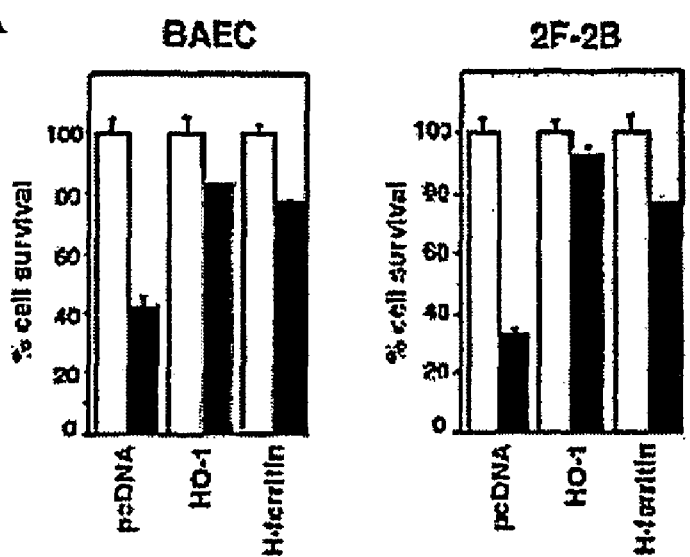
FIG. 13A is a pair of bar graphs illustrating percent cell survival in BAEC (left panel) or murine 2F-2B EC (ATCC; right panel) cotransfected with β-galactosidase plus control (pcDNA3 or pcDNA3/HO-1) or pcDNA3/H-Ferritin. Black bars indicate EC treated with TNF-α and Act.D. Gray bars represent EC treated with Act.D. One representative experiment out of six is shown. All results shown are the mean±SD from duplicate wells.
Figure 13B:
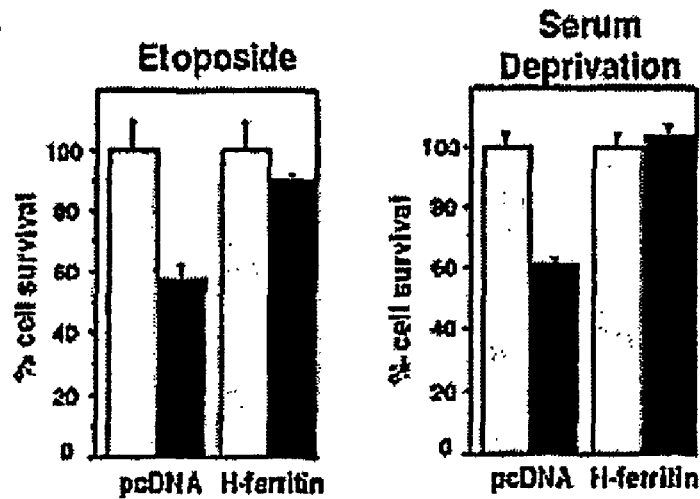
FIG. 13B is a pair of bar graphs illustrating percent cell survival in murine 2F-2B cells cotransfected with β-galactosidase plus control (pcDNA3) or pcDNA3/H-ferritin. Gray bars represent untreated EC and black bars represent EC treated with etoposide (200 µM, 8 h; left panel) or subjected to serum deprivation (0.1% FCS, 24 hours; right panel). One representative experiment out of three is shown. All results shown are the mean±SD from duplicate wells.
Figure 13C:
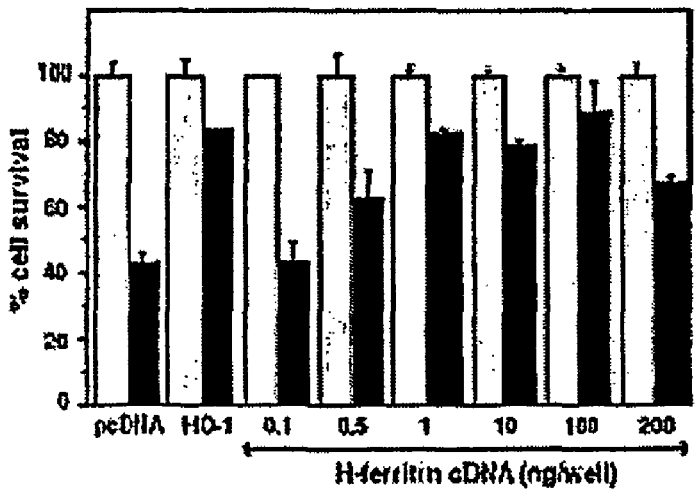
FIG. 13C is a bar graph illustrating percent cell survival in murine 2F-2B cells cotransfected with β-galactosidase plus increasing amounts of pcDNA/H-ferritin as indicated. Cells transfected with pcDNA3 or pcDNA3/HO-1 were used as controls. Black bars indicate EC treated with TNF-α and Act.D. Gray bars represent EC treated with Act.D. One representative experiment out of three is shown. All results shown are the mean±SD from duplicate wells.

H-ferritin protects endothelial cells from undergoing apoptosis. Control EC (transfected with pcDNA3) showed 60-70% apoptotic cells after exposure to TNF-α in the presence of the transcription inhibitor Actinomycin D (Act.D) (FIG. 13A-13C). Expression of H-ferritin suppressed TNF-α mediated EC apoptosis (10% apoptotic EC) (FIG. 13A-13C). This protective effect was observed in the EC line 2F-2B as well in primary bovine aortic EC (BAEC) (FIG. 13A). The anti-apoptotic effect of H-ferritin was also observed with other pro-apoptotic stimuli such as etoposide or serum deprivation (FIG. 13B). This effect was dose-dependent, showing protection from 1 ng to 100 ng of the pcDNA3/H-ferritin expression vector per $3 \times 10^5$ cells (FIG. 13C). Levels of pcDNA3/H-ferritin over 100 ng may be toxic as evidenced by an increasing number of apoptotic cells in TNF-α/Act.D stimulated cells as well as in control cells treated with pcDNA3/H-ferritin plus Act.D only (FIG. 13C).

Figure 14A:
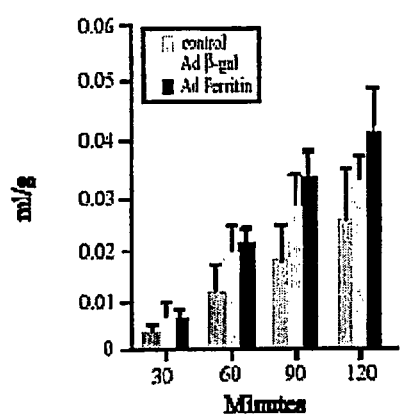
FIG. 14A is a bar graph illustrating bile production in livers harvested from SD rats, exposed to ischemia (24 hours, 4° C., UW solution) and perfused ex-vivo with syngeneic blood. Bile production is shown as mean±standard deviation from n=4. Notice that bile production at 120 minutes was significantly higher in livers transduced with H-ferritin versus non-transduced ($p<0.001$) or β-galactosidase transduced livers ($p<0.02$).

Recombinant adenovirus mediated H-ferritin expression protects livers from ex-vivo reperfusion injury. Rat livers exposed to prolonged cold ischemia (UW solution, 4° C., 24 hours) showed severe signs of injury once re-perfused ex-vivo with whole syngeneic blood. Injury was evidenced by the relative low increase in portal blood flow (from 0.63±0.076 ml/min/g at time 0 to 1.13±0.23 at ml/min/g at 120 min) and bile production (from 0.00338±0.0078 ml/g at time 0 to 0.025±0.01 mug at 120 min)(FIG. 14A) following reperfusion as well as by a significant increase in ALT release (from 7.2±4.9 IU/l at time 0 to 173±71 IU/l at 120 min). Similar results were obtained in β-galactosidase recombinant adenovirus transduced livers in that there was a similar level of portal blood flow (from 0.626±0.079 m/min/g at time 0 to 1.035±0.105 ml/min/g at 120 min) and relative low level of bile production (from 0.0005±0.0002 ml/g at time 0 to 0.03±0.0085 ml/g at 120 min) as well as significant ALT release (from 12.5±10.5 IU/l at time 0 to 148±92 IU/l at 120 min). Unlike untreated or β-galactosidase transduced groups, H-ferritin transduced livers showed significantly (p<0.01) greater increases in portal blood flow (from 0.62±0.099 ml/min/g at time 0 to 1.3721±0.133 ml/min/g at 120 min) and bile production (from 0.00621±0.0029 mug at time 0 to 0.043±0.0088 at 120 min)(FIG. 14A). Further, ALT release in the H-ferritin transduced livers remained at relatively low levels (from 9.3±4.51 U/l at time 0 to 68.6±14.8 IU/l at 120 minutes). At 2 hours of reperfusion, myeloperoxidase activity, a marker of neutrophil mediated oxidative stress injury, was significantly inhibited (p<0.05) in H-ferritin transduced livers (0.736±0.58 units/g), as compared to untreated (1.35±0.227 units/g) or β-galactosidase transduced (3.12±0.9 units/g) livers. These results support the notion that over-expression of H-ferritin protects livers from IRI despite prolonged periods of cold ischemia. Livers transduced with the H-ferritin gene also had a significantly better preservation of their histological detail, as compared to non-transduced (p<0.05) or β-galactosidase (p<0.05) transduced livers, as assessed by standard Suzuki's pathological scoring.

Figure 14B:
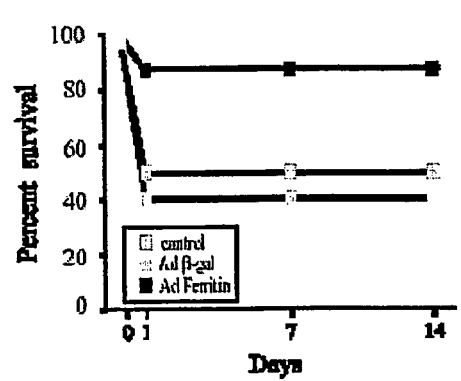
FIG. 14B is a bar graph illustrating recipient survival in a Kaplan Mayer format. Livers transduced with control β-galactosidase or H-ferritin adenoviruses were transplanted into syngeneic recipients. Eight to ten animals were analyzed per group. Prolonged survival in recipients receiving H-ferritin recombinant adenovirus transduced livers was significantly enhanced as compared to recipients transplanted with non-transduced or β-galactosidase recombinant adenovirus transduced livers ($p<0.001$).
Figure 14C:
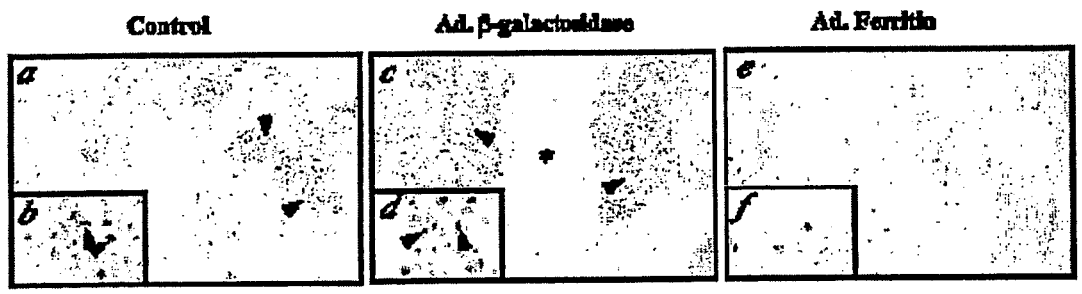
FIG. 14C is a set of photomicrographs of apoptosis in non-transduced livers or livers transduced with control α-galactosidase or H-ferritin adenoviruses transplanted into syngeneic recipients. Apoptosis was detected 24 hours after transplantation as described herein. Apoptotic cells are signaled with black arrows. Magnifications are 100× (a, c, e) or 400× (b, d, f).

Recombinant adenovirus mediated H-ferritin expression prevents IRI following orthotopic liver transplantation. Livers from SD rats exposed to prolonged cold ischemia (U.W. solution, 4° C., 24 hours) showed severe signs of hepatocellular damage following transplantation into syngeneic SD recipients. This was evidenced by the high serum levels of AST (3928±1455 IU/L) 24 hours post-transplant. Similar results were obtained in liver transplant recipients transduced with a β-galactosidase recombinant adenovirus (4887±500 IU/L). In marked contrast, in animals bearing liver transplants transduced with the H-ferritin recombinant adenovirus, AST release (1368±550.8 IU/L) was significantly inhibited as compared to β-galactosidase/untreated groups (p<0.05). That H-ferritin transduced livers were protected from IRI is strongly supported by the demonstration that up to 90% of H-ferritin transduced livers survived for longer than 14 days when transplanted into syngeneic SD recipients. In marked contrast, only 40-50% of non-transduced or α-galactosidase transduced livers survived longer than 14 days when transplanted into syngeneic SD recipients (FIG. 14B). The relative number of cells undergoing apoptosis in H-ferritin transduced livers transplanted into syngeneic recipients was significantly reduced as compared to non-transduced or β-galactosidase-transduced livers transplanted under the same conditions (FIG. 14B). Prolonged survival in recipients receiving H-ferritin recombinant adenovirus-transduced livers was significantly enhanced as compared to recipients transplanted with non transduced or β-galactosidase recombinant adenovirus transduced livers (p<0.001). This finding is consistent with the hypothesis that the anti-apoptotic effect of H-ferritin may contribute to its overall cytoprotective function in transplanted livers.

Model for the cytoprotective action of ferritin. As shown in FIG. 15, upon ischemia and reperfusion, free heme is internalized by EC. HO-1 action on heme releases $Fe^{2+}$, which catalyzes the conversion of hydrogen peroxide ($H_2O_2$) into $OH^-$ and $OH^-$, through the Fenton reaction. These trigger signal transduction pathways that promote inflammation and apoptosis. Ferritin binds $Fe^{2+}$ and prevents it from reacting with $H_2O_2$, thus blocking this process.

Conclusions

These results demonstrate an anti-apoptotic function of H-ferritin and suggest that an increase in H-ferritin activity, e.g., by administration of exogenous ferritin or by increased expression of the H-ferritin gene, can be used in a therapeutic manner. By its ability to suppress liver IRI, expression of the H-ferritin gene may result in the safer use of liver transplants despite prolonged periods of cold ischemia. As one theory, not meant to be limiting, the protective effect of H-ferritin appears to be associated with its ability to inhibit endothelial cell (EC) and hepatocyte apoptosis in vivo and in vitro.

Example 4

Enhanced Islet Graft Survival

The ability of exogenously administered biliverdin or CoPP to enhance syngeneic islet transplantation was evaluated.

Materials and Methods

Animals. Male DBA/2, B6AF1 and DBA/1 mice 6-8 week of age (Jackson) are used in the experiments. Mice were kept for 2 weeks at 4 mice/cage and fed normal laboratory chow before using for the experiment.

Treatment protocol. Recipients were rendered diabetic using streptozotocin (STZ, 225 mg/kg). Five days after STZ administration, animals with two consecutive blood glucose levels exceeding 350 mg/dl are used as recipients. Islets (500) are transplanted under the kidney capsule of the recipients.

Reagents. Cobalt protoporphyrin (CoPPIX, Porphyrin Products, Logan, Utah), biliverdin dihydrochloride and bilirubin (ICN Biomedicals Inc., OH) were dissolved in a small amount of 0.2 M NaOH, subsequently adjusted to a pH of 7.4 with 1 M HCl, and diluted in 1×PBS. The stock solutions (CoPPIX=2 mg/ml, biliverdin=3.2 mg/ml, bilirubin=0.5 mg/ml) were aliquoted and kept at −70° C. until used. Light exposure was limited as much as possible.

Induction of HO-1/Administration of biliverdin/bilirubin. When given to the donor, CoPPIX (20 mg/kg) was given 24 hours before islet isolation to induce HO-1 expression. To verify HO-1 expression in different organs after CoPP treatment, tissue samples are collected 24 hours after treatment and snap frozen in liquid nitrogen. Immunohistological analysis of HO-1 expression is performed using an anti-HO-1 antibody. CoPPIX (20 mg/kg) was administrated to the recipient intraperitoneally (i.p.) on day-1, 1, 3, 5 and 7. Biliverdin (50 µmol/kg) or bilirubin (8.5 µmol/kg) was given intraperitoneally to the donor one hour before islet isolation. For the recipient, biliverdin (50 µmol/kg) or bilirubin (8.5 mmol/kg) was administered intraperitoneally either daily or twice per day from day-1 until day 13. No further treatment was given afterwards.

Measurement of Glucose level. Glucose levels were tested twice weekly after transplantation. Glucose levels of <200 mg/dl were considered normoglycemic. Grafts were considered rejected when two consecutive glucose levels were >300 mg/dl.

Tolerance test. The first graft was removed from a number of animals that had islets surviving long-term (longer than 100 days) by doing a nephrectomy. Islets syngeneic with the original donor were transplanted under the contralateral kidney capsule without further treatment. If those second transplanted islets also survived longer than 100 days without further treatment, the recipients were considered tolerant. Antigen-specific tolerance was assessed by transplanting islets of a third-party donor (DBA/1) that does not share either class I or class II antigens with the original donor.

Pathology. Hematoxylin and eosin (H&E) and insulin staining were performed on grafts that survived long-term (longer than 100 days).

Semi-Quantitative PCR. RNA was extracted using Rneasy™ Mini Kits (Qiagen Inc., CA, USA) and reverse transcribed into cDNA with the RNA PCR Kit (TaKaRa, PanVera, Madison, Wis., USA). A total of 2 µg of cDNA was amplified in a 50 µl reaction mix containing 10 µM dNTPs, 50 µg of 5'-prime and 3'-prime oligos, 2.5 U of LA-Taq polymerase (TaKaRa) and $MgCl_2$, specific to each primer pair used. The primers for murine and human HO-1 (372 bp) (5': TGA AGG AGG CCA CCA AGG AGG T (SEQ ID NO:1); 3': AGG TCA CCC AGG TAG CGG GT (SEQ ID NO:2)) and β-actin (525 bp) (5': GCC ATC CTG CGT CTG GAC CTG G (SEQ ID NO:3); 3': TAC TCC TGC TTG CTG ATC CAC A (SEQ ID NO:4)) were obtained from LifeTechnologies, NY, USA. PCR reactions were performed after a 4 min denaturation at 94° C. a repeating the cycle 94° C., 55° C. and 72° C. each for 1 min for number of cycles specific for each primer pair in a Peltier Termal Cycler PTC-200 (MJ Research, Las Vegas, Nev., USA). PCR products (10-20 µl) were analyzed in an ethidium bromide-stained 1% agarose gel.

Results

Figure 16:
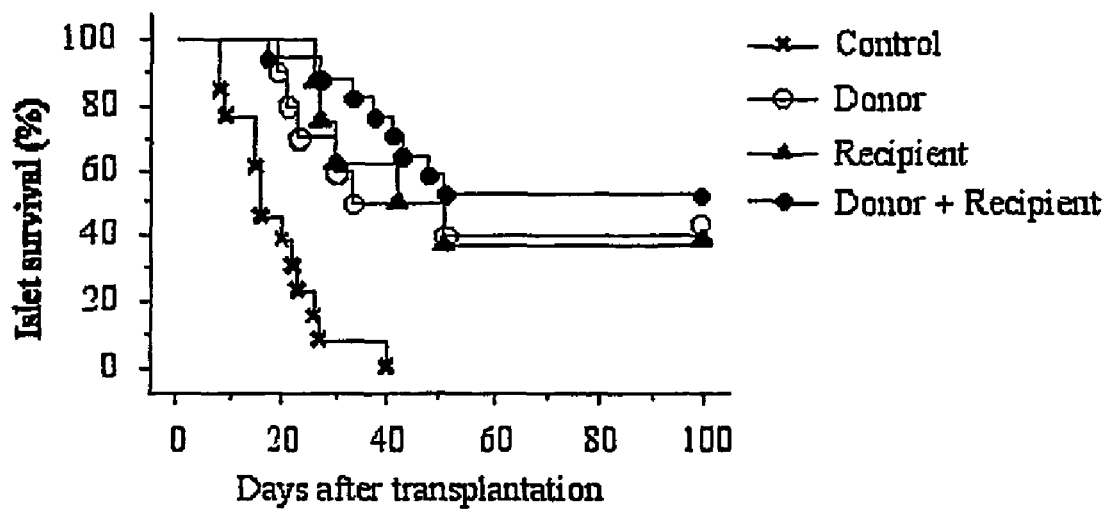
FIG. 16 is a line graph illustrating the effect on islet transplant survival of treatment of the donor, recipient, or both with CoPP.

HO-1 in allogeneic islet transplantation. When CoPP was given to the donor animal, HO-1 expression was observed in several different tissues such as heart, kidney, pancreas, liver and spleen. HO-1 expression in isolated islets was verified by semi-quantitative PCR analysis. Islet transplantation was done from DBA/2 ($H-2^d$) to B6AF1 ($H-2^{b/a}$) mice. Subsequently, HO-1 was induced with CoPP for allogeneic transplantation. HO-1 was induced in the donor from one day before taking the islets and in the recipient on days −1, 1, 3, 5 and 7 with regard to transplantation. This protocol led to prolongation of survival in general but also to some islets surviving long-term (longer than 100 days) despite the absence of any treatment after day 7 after transplantation. In addition, inducing HO-1 only in the donor without treatment of the recipient led not only to prolonged survival and function of the islets in the recipient but also to an occasional long-term surviving graft. Survival results with treatment of the donor and recipient and the recipient alone are also shown (FIG. 16). In the tolerance test, all five animals that had been transplanted with syngeneic islet (DBA/2) accepted the $2^{nd}$ graft indefinitely (longer than 100 days) while the third party grafts (n=3) were rejected rapidly.

Figure 17:
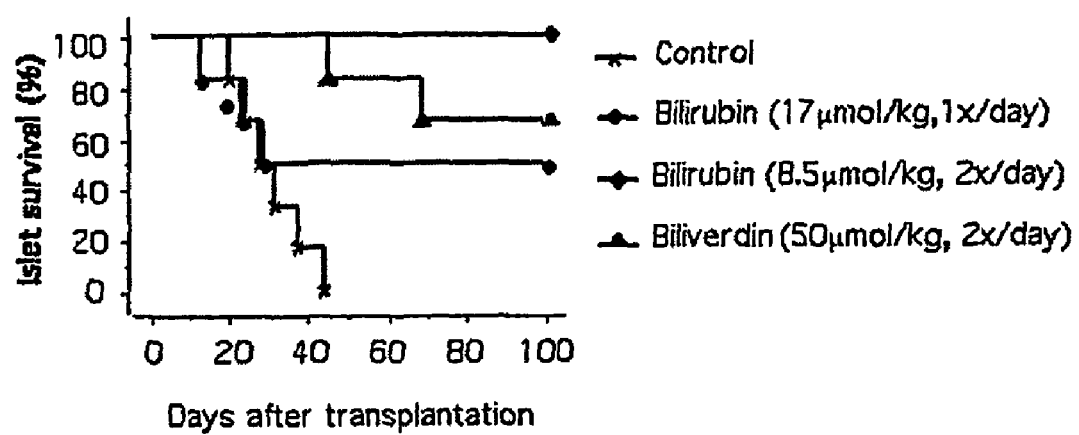
FIG. 17 is a line graph illustrating the effect on islet transplant survival of treatment of the donor and recipient with bilirubin or biliverdin.

Induction of long-term survival of allogeneic islets by administration of biliverdin or bilirubin. Administration of biliverdin or bilirubin to the DBA/2 donor and B6AF1 recipient led to 66.7% to 100% long-term survival, even though there was no treatment given after day 13 post-transplantation. The half-life of bilirubin after administration of biliverdin was only 2.5 to 3.5 hours. Thus, giving one dose of bilirubin to the donor and recipient was compared to giving two (every twelve hours) doses per day. The single dose led to prolongation of survival of the islets and 50% long-term survival while 2 dose led to 100% long-term survival. Treatment of the recipient only with biliverdin or bilirubin also led to a significant percentage of long-term surviving islets (FIG. 17). Antigen specific tolerance was also seen in some of the long-term survival animals treated with biliverdin or bilirubin.

The ability of exogenously administered biliverdin to protect transplanted islet was evaluated in the minimal mass model. Syngeneic islet transplantation was carried out in the DBA/2 mouse. Islets (140) were transplanted under the kidney capsule of diabetic mice. Test animals were treated with 50 µmol/kg biliverdin twice daily from day-1 until day 7. The controls were treated with vehicle only. Biliverdin treated animals returned to normoglycemia in 7.7±5.5 days; animals in control group remain hyperglycemic (>52 days).

Conclusion

Treatment of the donor and/or recipient of a syngeneic islet transplant with biliverdin or CoPP enhances graft survival and successful treatment of diabetic hyperglycemia.

Example 5

Inhibition of Neointimal Formation

The effect of administration of CoPP or biliverdin on formation of neointimal tissue was evaluated.

Materials and Methods

Animals. Adult male Lewis Rats (LEW/CrlBR; Charles River Laboratories, Wilmington, Mass.) weighing 350-400 g were used in the balloon injury model. Animals were housed in accordance with the guidelines from the American Association for Laboratory Animal Care and research protocols were approved by the institutional animal care and use committee of the Beth Israel Deaconess Medical Center, Boston, Mass.

Balloon Injury model. After the exposure of the left common carotid and the left external carotid arteries, a 2F Fogarty catheter (Edwards Lifesciences LLC, Irvine, Calif.) was introduced via the external carotid artery and was advanced into the left common carotid artery, inflated to 2 atmospheres of pressure and pulled back to the point of bifurcation, then deflated. This procedure was repeated three times.

Experimental reagents and design. Biliverdin dihydrochloride (ICN Biomedicals Inc., Aurora, Ohio) was dissolved in a small amount of 0.2 M NaOH, subsequently adjusted to a pH of 7.4 with 1 M HCl and diluted in PBS. The stock solution was kept at −70° C. until used. Light exposure was limited as much as possible.

Local biliverdin delivery. After proximal ligation of the common carotid artery (CCA) and distal ligation of the internal carotid artery (ICA) a polyethylene catheter was introduced into the external branch of the carotid artery and the CCA was flushed. 50 µl of PBS or Biliverdin diluted in PBS at concentrations of 1 and 0.1 mM was infused and incubated for 1 hour prior to or immediately after the injury, shaded from the light. Biliverdin was removed, the CCA flushed two times with 0.9% NaCl, and blood flow was restored through the CCA and ICA.

Systemic biliverdin treatment. Biliverdin was injected intraperitoneally at a dose of 50 µmol/kg. The first dose was injected 3 hours before, the second dose immediately after the surgical procedure.

Results

Figure 18:
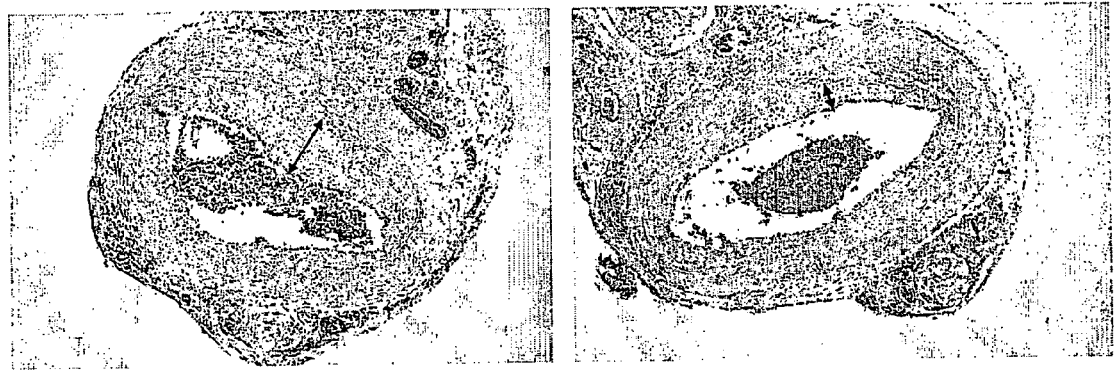
FIG. 18 is a pair of photomicrographs illustrating the effect of pre-treatment with biliverdin on neointimal formation in rat carotid arteries after balloon injury.

Histomorphometric analysis. Carotid arteries were harvested 14 days after balloon injury, either fixed in 10% formalin and imbedded in paraffin or quick-frozen in 2-methylbutane. Serial sections of 5 µm in a distance of 200 µm were stained with hematoxylin-eosin stain. Images of 6 sections of each vessel were taken at a resolution of 768×512 pixels with a Zeiss microscope (Axioskop™, Zeiss, Iowa City, Iowa). Images were analyzed by manual segmentation, tracing intima and media in each section. Areas and diameters were calculated by digital imaging software (AxioVision™, Carl Zeiss, Jena, Germany) as number of pixels corresponding to those areas and diameters. Intima media ratio (area, diameter) and luminal cross-sectional area narrowing were used to assess neointimal formation. The person in charge of histomorphometric analysis was blinded to the treatment. 24 sections from each group were statistically analyzed with StatView® software version 5.0 using ANOVA. As is shown in FIG. 18, local pre-treatment of rat carotid arteries instilling biliverdin into the common carotid artery for one hour as well as systemic treatment with biliverdin at two time points significantly inhibits neointimal formation (arrows) after balloon injury.

Conclusion

Treatment with biliverdin or CoPP can significantly reduce arterial injury following balloon injury, e.g., restenosis.

Example 6

Endotoxic Shock

The anti-inflammatory protective effects of biliverdin were evaluated in an animal model of endotoxic shock.

Materials and Methods

Treatment Protocol. Endotoxin (lipopolysaccharide/LPS; Sigma; *E. coli* serotype 0128:B7; 3 mg/kg, i.v.) was administered to male Sprague-Dawley, resulting in an acute non-lethal inflammation. In rats, a sublethal dose of LPS results in a moderate lung inflammation characterized by neutrophil accumulation and protein accumulation in the airspace, both markers of lung inflammation. The pro-inflammatory cytokine TNF-alpha increases very rapidly in the serum, peaking by 60-90 minutes. This is followed by increases in IL-10, a prototypical anti-inflammatory cytokine that peaks 8-12 hr later.

Administration of Biliverdin. Biliverdin (Frontier Scientific: prepared in PBS following solubilization in NaOH) was administered i.p. at 50 mmol/kg 17 hours prior to, one hour prior to, and eight hours after LPS administration.

Bronchoalveolar Lavage. A bronchoalveolar lavage (BAL) was performed 24 hours after LPS administration. Serum cytokines were measured using commercially available ELISA kits (R&D Systems Inc.) per the manufacturer's instructions. Total protein was determined via a standard Bradford assay based on a standard curve. BAL was performed using standard methods; briefly, a tracheostomy was performed and 8 ml (approximately 35 ml/kg) of PBS was instilled three times. Total cell count was determined as well as differential analysis of cell type and morphology via Diff-Quik® Fixative (American Scientific Products) staining of a sample of the lavagate.

Results

Figure 19:
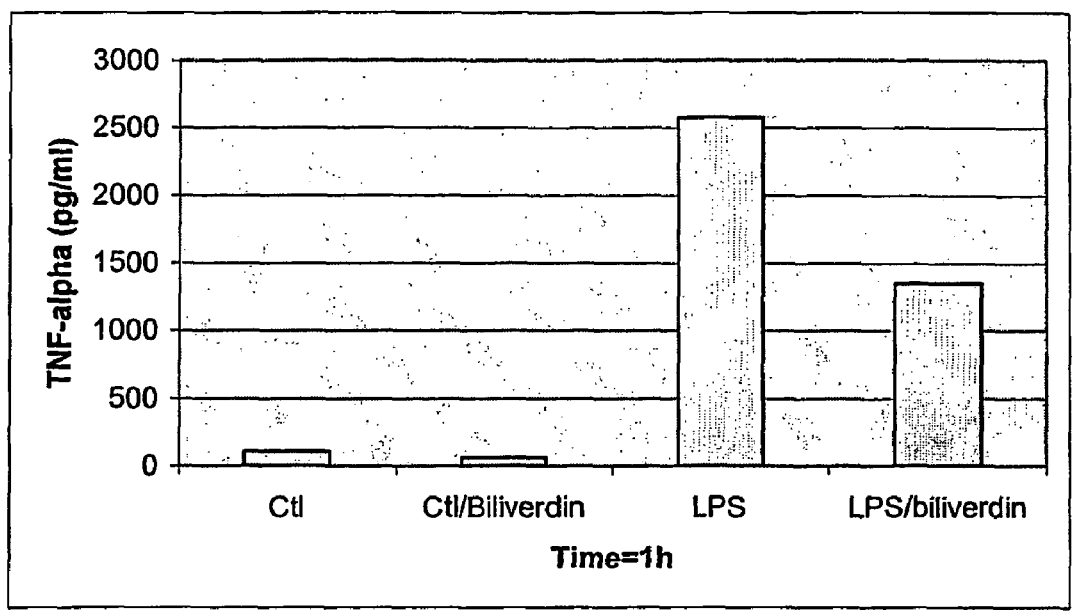
FIG. 19 is a bar graph illustrating the effect of biliverdin pre-treatment on LPS-induced TNF-α production in rats. Ctl=control
Figure 20:
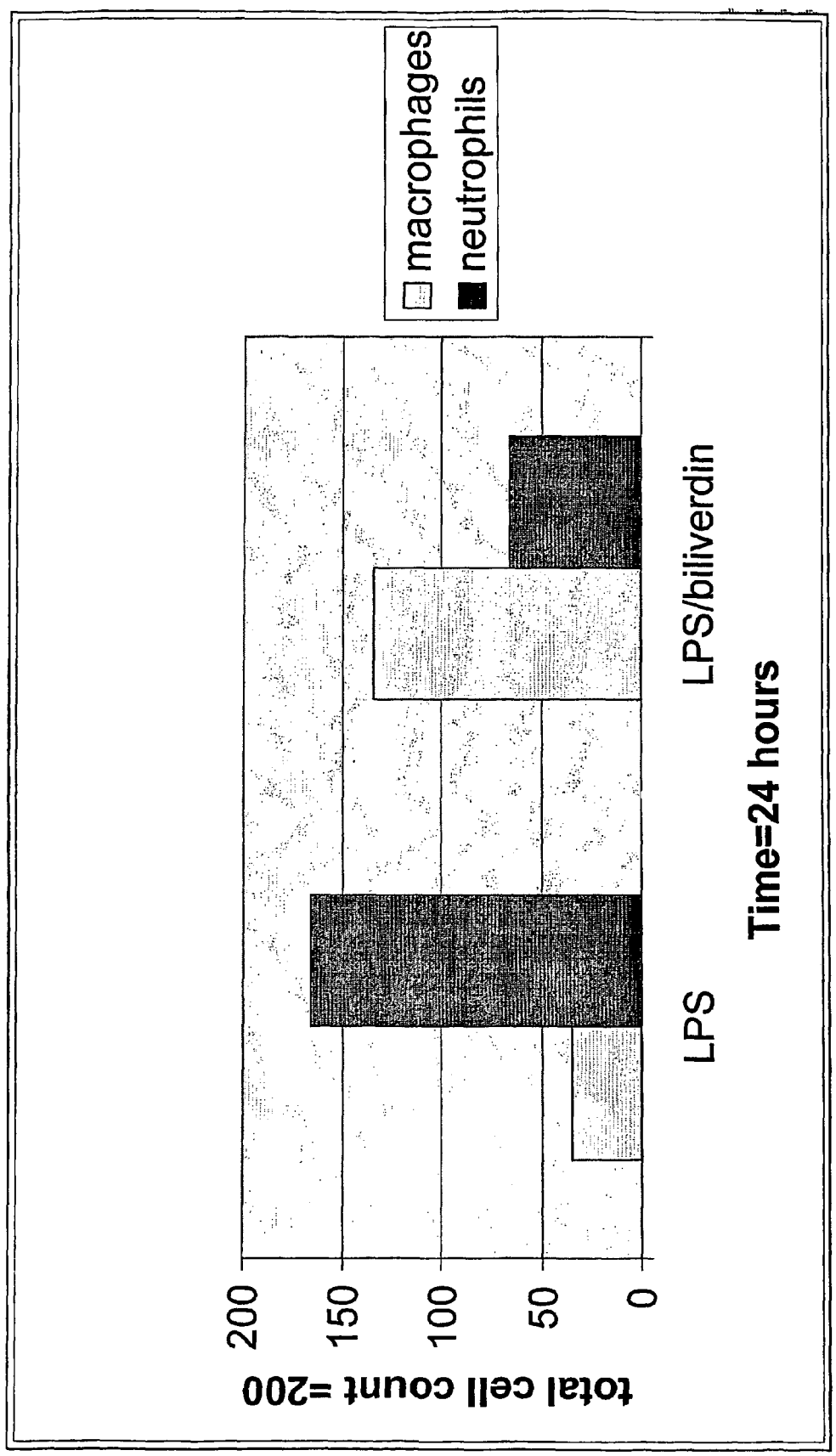
FIG. 20 is a bar graph illustrating the effect of biliverdin pre-treatment on neutrophil accumulation in the lungs of rats treated with LPS. In untreated control rats, 200 of 200 cells are macrophages, no neutrophils are present.
Figure 21:
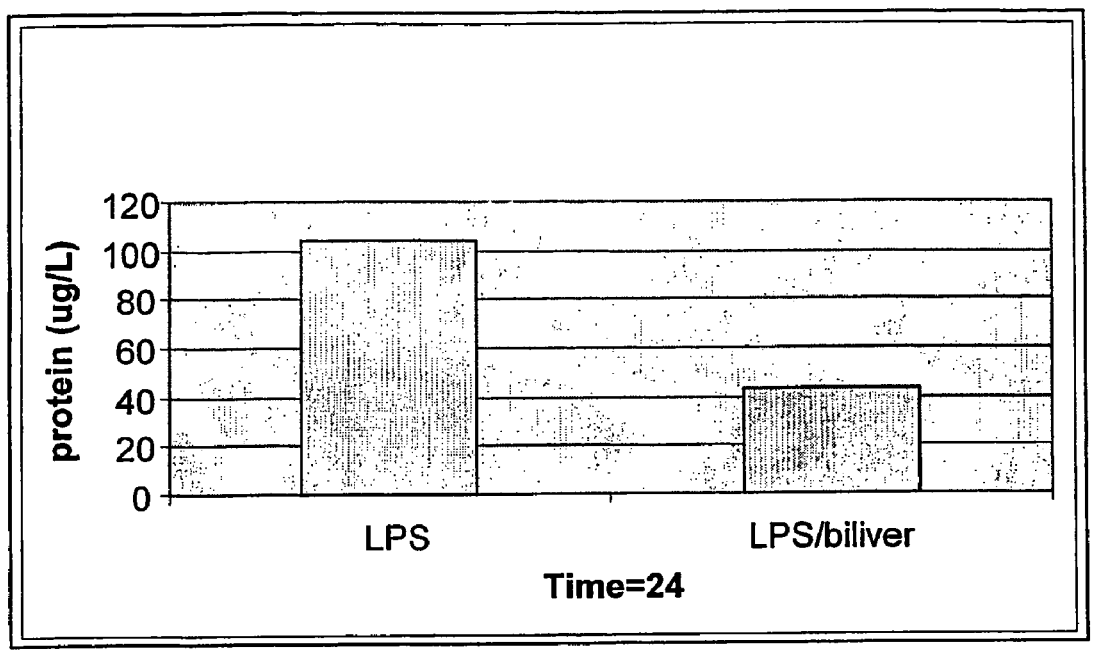
FIG. 21 is a bar graph illustrating the effect of biliverdin pre-treatment on protein accumulation in the lungs of rats treated with LPS. Normal baseline levels are around 30.
Figure 22:
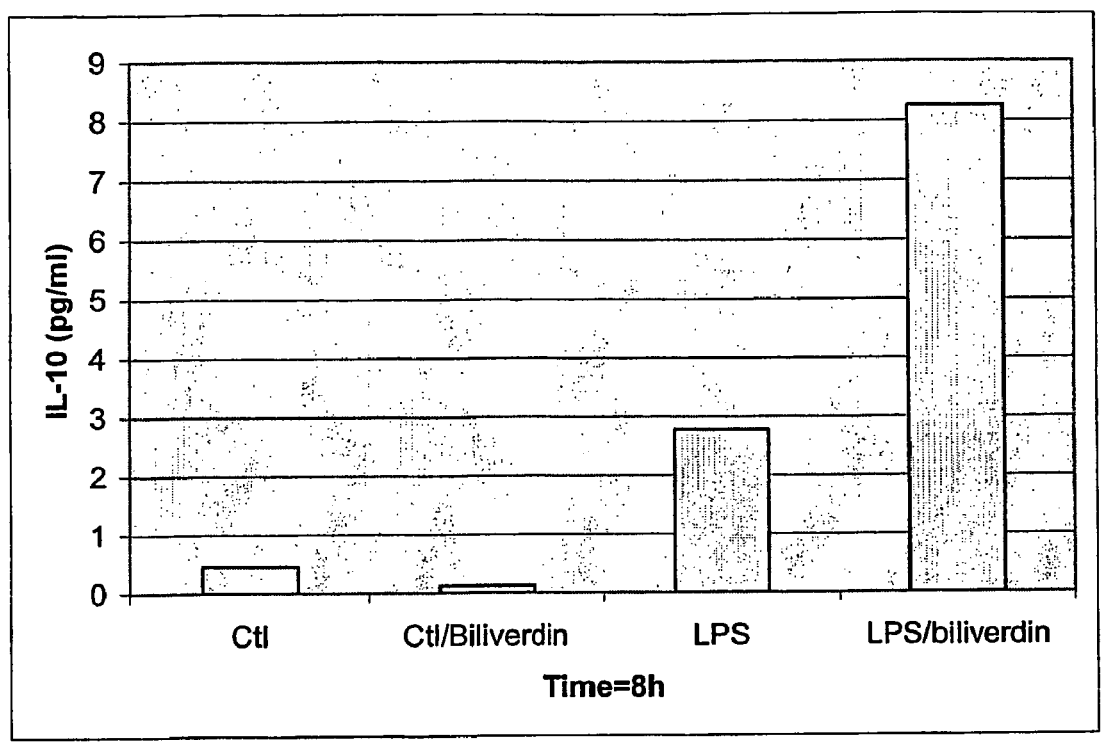
FIG. 22 is a bar graph illustrating the effect of biliverdin pre-treatment on IL-10 levels in rats treated with LPS.

Biliverdin administration reduced levels of LPS-induced TNF-alpha (FIG. 19) as well as levels of neutrophil (FIG. 20) and protein (FIG. 21) accumulation in the airspace. Biliverdin administration also resulted in an augmentation of the anti-inflammatory cytokine, IL-10 (FIG. 22).

Conclusions

Biliverdin is a potent anti-inflammatory agent, as evidenced by its ability to reduce the inflammatory effects associated with endotoxin administration in rats.

Example 7

Hepatitis

The effect of treatment with biliverdin was evaluated in a mouse model of hepatitis.

Materials and Methods

Male mice (C57BL/6J) were administered biliverdin (50 mmol/kg, i.p.) 16 hours and 1 hour prior to i.p. injection of a cocktail including 0.3 ug/mouse TNF-α (mouse TNF-α; Gibco) and 250 mg/kg, i.p. D-Galactosamine (Sigma), which induces fulminant hepatitis within 6-10 hours. Control mice received PBS vehicle. Serum samples were taken via cardiac puncture 6-8 hours later and analyzed for alanine aminotransferase (ALT) per an ALT assay kit from Sigma Chem. Co. following the manufacturer's directions.

Results

Biliverdin reduced serum ALT levels by more than 90% as compared to vehicle treated controls (about 1000 IU/ml in control versus 100 IU/ml in treated animals). As a reference, a normal ALT level is 20-30 IU/ml.

Conclusions

Biliverdin treatment is effective in reducing the liver injury and symptoms associated with hepatitis, including acute hepatitis.

Example 8

Small Intestine Transplantation

The effect of treatment with biliverdin was assessed in an animal model of small intestine transplantation.

Materials and Methods.

Animals. Inbred male LEW (RT1) rats weighing 200-300 grams were purchased from Harlan Sprague Dawley, Inc. (Indianapolis, Ind.), and maintained in a laminar flow animal facility at the University of Pittsburgh. Animals were fed with a standard diet ad libitum.

Small Intestinal Transplantation. Orthotopic small intestinal transplantation (SITx) was performed in syngeneic Lewis rats. SITx with caval drainage was performed using a previously described procedure (Murase et al., in Handbook of Animal Models in Transplantation Research, Cramer et al., Eds. CRC Press, Boca Raton, Fla., pp. 203-213 (1994)). The entire donor small intestine from the ligament of Treitz to the ileocecal valve was isolated on a vascular pedicle consisting of the portal vein and the superior mesenteric artery in community with a segment of aorta. The graft was perfused via the aortic segment with 5 ml chilled Ringer's lactate solution, and the intestinal lumen was irrigated with 20 ml of cold saline solution containing 0.5% neomycin-sulfate (Sigma, St. Louis, Mo.). End-to-side anastomoses between the graft aorta and the recipient infrarenal aorta, and between the graft portal vein and recipient vena cava, were performed with 10-0 Novafil™ suture. The cold ischemic time was 1 hour. The entire recipient intestine was removed and the enteric continuity was restored by proximal and distal end-to-end intestinal anastomoses. Recipient animals were given 20 mg/day prophylactic cefamandole nafate for 3 postoperative days. Transplanted recipients were given water 3 hours after surgery, and were fed 24 hours after surgery.

SYBR green real time RT-PCR. The effects of administration of biliverdin on transplant-induced pro-inflammatory and anti-inflammatory gene expression were assessed in muscularis extracts by RT-PCR Biliverdin (50 mmol/kg, i.p.) was administered to both the donor and recipient three hours preoperatively. The muscularis externae was collected from normal intestine and transplanted grafts 4 hours postoperatively and snap frozen in liquid nitrogen. This time point falls within the range of maximum inflammatory mediator expression that occurs between 3 and 6 hours following abdominal incision. Total RNA extraction was performed using the guanidium-thiocyanate phenol-chloroform extraction method as described previously (Eskandari et al., Am. J. Clin. Pathol. 75(3):367-370, 1997). RNA pellets were resuspended in RNA-secure resuspension solution (Ambion Inc., Austin, Tex.), followed by removal of potentially contaminating DNA by treatment with DNase I (DNA-Free Kit, Ambion Inc., Austin, Tex.). Equal aliquots (5 μg) of total RNA from each sample were quantified by spectrophotometry (wavelength 250 nm) and aliquoted at a concentration of 40 ng/μl. Peak mRNA expression was quantified in duplicate by SYBR Green two-step, real-time RT-PCR. GAPDH was used as the endogenous reference. Aliquoted RNA was subjected to first-strand complementary DNA (cDNA) synthesis using random hexamers (PE applied Biosystems, Foster City, Calif.) and Super Script II™ (Life Technologies, Rockville, Md.). Primer sequences were obtained from the literature or designed according to published sequences (Table 2). A PCR reaction mixture was prepared using SYBR Green PCR Core Reagents (PE Applied Biosystems). Each sample was estimated in duplicate using the conditions recommended by the manufacturer. The reaction was incubated at 50° C. for 2 min to activate the uracil N'-glycosylase and then for 12 min at 95° C. to activate the Amplitaq Gold™ polymerase followed by 40 cycles of 95° C. for 15 sec and 60° C. for 1 min on an ABI PRISM 7700™ Sequence Detection System (PE Applied Biosystems, Foster City, Calif.). Real-time PCR data were plotted as the $\Delta R_n$ fluorescence signal versus the cycle number. An arbitrary threshold was set to the mid-linear portion of the log $\Delta R_n$ cycle plot. The threshold cycle ($C_T$) was defined as the cycle number at which the $\Delta R_n$ crosses this threshold. Quantification of mRNA expression was normalized to GAPDH and calculated relative to control using the comparative $C_T$ method (Schmittgen et al., J. Biochem. Biophys. Methods 46(1-2):69-8, 2000).

To exclude PCR amplification of contaminating genomic DNA, RT-negative controls (samples containing RNA that was not reverse transcribed) were included in each PCR reaction. Melting curve analyses were performed for each reaction to ensure amplification of specific product. In addition, the primers were subjected to gel electrophoresis to confirm the absence of non-specific bands and to confirm that the amplicons were of the correct size. Efficiency of PCR-amplification of target cDNA was examined to measure colinearity of dilution. Serial 3-fold dilutions of cDNA were performed in triplicate. Standard curves were generated by plotting $C_T$ value against relative input copy number. Slopes of the standard curves of −3.2±0.3 with correlation coefficients of 0.99 were considered to be acceptable, having corresponding efficiencies of 100±10%.

zontal mechanical organ chambers that were continuously superfused with pre-oxygenated KRB maintained at 37° C. One end of each strip was attached by ligature to a fixed post and the other to an isometric force transducer (WPI, Sarasota, Fla.). Strips were allowed to equilibrate for 1 hour, after which they were incrementally stretched to the length at which maximal spontaneous contraction occurred ($L_o$). After a second equilibration period of 30 minutes, contractility-response curves were generated by exposing the tissues to increasing concentrations of the muscarinic agonist bethanechol (0.3 to 300 μM) for 10 minutes, followed by a 10-minute wash period. Contractile activity was calculated by integrating the area under the trace, normalized by converting the weight and length of the strip to square millimeters of tissue (1.03 mg/mm$^2$), and reported as g/s/mm$^2$.

Measurement of Intestinal Blood Flow. Intestinal microvascular blood flow was monitored by placing the flat probe of a laser Doppler flowmeter (BLF 21D, Transonic Systems, Ithaca, N.Y.) on the serosal surface of the graft jejunum and ileum adjacent to the mesenteric border. Blood flows in SMA and marginal artery (MA) were also analyzed.

TABLE 2

Primer summary

| Primer | Sequence 5' to 3' | SEQ ID NO | Source |
|---|---|---|---|
| GAPDH | ATGGCACAGTCAAGGCTGAGA | 9 | NM_017008 |
|  | CGCTCCTGGAAGATGGTGAT | 10 |  |
| IL-6 | GCCCTTCAGGAACAGCTATGA | 11 | M26744 |
|  | TGTCAACAACATCAGTCCCAAGA | 12 |  |
| IL-1β | CACCTCTAAGCAGAGCACAG | 13 | Li & Wang, Brain Research |
|  | GGGTTCCATGGTGAAGTCAAC | 14 | Protocols 2000; 5, 211-217 |
| TNFα | GGTGATCGGTCCCAACAAGGA | 15 | Fink et al. Nature Med 1998; 4; |
|  | CACGCTGGCTCAGCCACTC | 16 | 1329-1333. |
| ICAM-1 | CGTGGCGTCCATTTACACCT | 17 | NM_012967 |
|  | TTAGGGCCTCCTCCTGAGC | 18 |  |
| iNOS | GGAGAGATTTTTCACGACACCC | 19 | NM_012611 |
|  | CCATGCATAATTTGGACTTGCA | 20 |  |
| COX-2 | CTCTGCGATGCTCTTCCGAG | 21 | AF233596 |
|  | AAGGATTTGCTGCATGGCTG | 22 |  |
| IL-10 | TGCAACAGCTCAGCGCA | 23 | Harness et al., J. Neurol. Sci. |
|  | GTCACAGCTTTCGAGAGACTGGAA | 24 | 2001; 187, 7-16. |

Motility Studies. The effect of administration of biliverdin on treatment on intestinal dysmotility in transplanted grafts was assessed both in vitro and in vivo. Tissues were harvested 24 or 48 hours post-operatively, which have been shown to be time points during which transplant-induced dysmotility peaks. In vitro circular muscle mechanical activity was measured as previously described (Eskandari et al., Am. J. Physiol. 273(3 Pt 1):G727-34, 1997). Rats were anesthetized and killed by exsanguination 24 hours post-operatively. A segment of mid-jejunum was pinned in a Sylgaard™ lined dissecting dish containing pre-oxygenated Krebs-Ringer-bicarbonate buffer (KRB; in mM: 137.4 Na$^+$, 5.9 K$^+$, 2.5 Ca$^{2+}$, 1.2 Mg$^{2+}$, 134 Cl$^-$, 15.5 HCO$_3^-$, 1.2 H$_2$PO$_4^-$, and 11.5 glucose) that was equilibrated with 97% O$_2$/3% CO$_2$. The intestine was opened along the mesenteric border and the mucosa removed by stripping with fine forceps. Full-thickness strips of muscularis (1×6 mm) were cut parallel to the circular muscle layer. Muscle strips were mounted in standard hori- Measurement of Intestinal Blood Flow. Microvascular blood flow for in grafts preserved for 6 hours was measured using a laser Doppler flowmeter (BLF 21D, Transonic Systems, Ithaca, N.Y.) equipped with a flat probe. Intestinal microvascular blood flow was monitored by placing the probe on the serosal surface of the graft jejunum and ileum adjacent to the mesenteric border. Blood flow in the superior mesenteric artery (SMA) and marginal artery (MA) were also measured.

Graft permeability. The preparation of everted gut sacs was performed in ice-cold modified Krebs-Henseleit bicarbonate buffer [KHBB (pH 7.4)] consisting of 10 mM HEPES, 137.0 mM NaCl, 5.36 mM KCl, 4.17 mM NaHCO3, 0.34 mM Na2HPO4, 0.44 mM KH2PO4, 0.41 mM MgSO47H$_2$O, 0.49 mM MgCl26H$_{20}$, 1.26 mM CaCl$_2$, and 19.45 mM glucose. One end of the gut segment was ligated with 4-0 silk. The resulting gut sac was everted using a thin plastic rod. A groove was cut into the tip of a 5 ml plastic syringe and 1.5 mL of KHBB was drawn into the syringe. The open end of the everted gut sac was secured to the groove using 4-0 silk, and the intestine was gently distended by injecting the KHBB from the syringe. The sac was suspended in a beaker holding 80 mL of a solution of KHBB maintained at 37° C. and containing fluorescein-isothiocyanate dextran (average M.W. 4000 Da; FD4; 20 mg/mL). The bathing solution was aerated by gently bubbling with a gas mixture containing 95% $O_2$ and 5% $CO_2$. At the beginning of the experiment, 1.0 mL of the bathing solution was removed to measure the initial concentration of FD4. Following a 30 min incubation, the length of the sac was measured, and 1.0 mL of the fluid within the gut sac was collected. The samples were cleared by centifugation at 1,000 rpm for 10 min at 4° C. Subsequently, 300 ul of the supernatant was diluted with 3.0 mL of phosphate buffered saline, and the fluorescence of the solution was measured using a Perkin-Elmer LS-50 fluorescence spectrophotometer (Palo Alto, Calif.) at an excitation wave length of 492 nm (slit width=10.0 nm) and an emission wavelength of 515 nm (slit width=10.0 mm).

Detection of Serum Mediators. Serum samples from the recipients transplanted with preserved intestine were taken at 3 and 12 hours after reperfusion and stored at −800 until evaluation. Serum IL-6 was determined using a rat enzyme-linked immunoassay (ELISA) kits as described by the manufacturer (R & D Systems, Inc., Cambridge, Mass.). To monitor the production of nitric oxide, the stable end products of NO metabolism, serum nitrite/nitrate levels, were measured 12 hours after engraftment using a commercially available test kit (Cayman, Ann Arbor, Mich.). In this assay system, nitrate is reduced to nitrite using nitrate reductase, and the nitrite concentration of the sample is subsequently measured using the Griess reaction.

Data Analysis. Results are expressed as mean plus or minus the standard error of the mean (SEM). Statistical analysis was performed using Student's t test or analysis of various (ANOVA) where appropriate. A probability level of $p<0.05$ was considered statistically significant.

Results

SITx without Preservation (Minor Injury)

Serum bilirubin levels and BVR expression in the graft. To assess how fast injected biliverdin (BV) is metabolized into bilirubin, sequential serum bilirubin levels were analyzed. Before BV treatment, serum bilirubin levels were undetectable. Thirty minutes after BV injection i.p., serum bilirubin levels reached a peak of 1.07±0.5 mg/dl compared to those of normal animals. By 2 hours after injection i.p., bilirubin levels returned to normal.

Circular muscle contractility. To determine the direct effects of SITx and BV on the muscular apparatus, the effects of SITx with and without BV treatment were investigated on spontaneous and bethanechol-stimulated jejunal circular muscle contractility using in vitro organ bath experiments. Tissues were harvested 24 hours after transplantation of the intestinal graft, a time point when intestinal motility associated with SITx is known to be maximally suppressed (Schwarz et al., Surgery 131:413-423 (2002)).

Control animals treated with BV demonstrated no change in their spontaneous muscle contractile activity. SITx results in a significant decrease in spontaneous muscle contractile activity, however, jejunal muscle strips harvested from grafts transplanted into recipient animals treated with BV demonstrated significantly greater spontaneous contractile activity as compared to untreated transplants.

Figure 25:
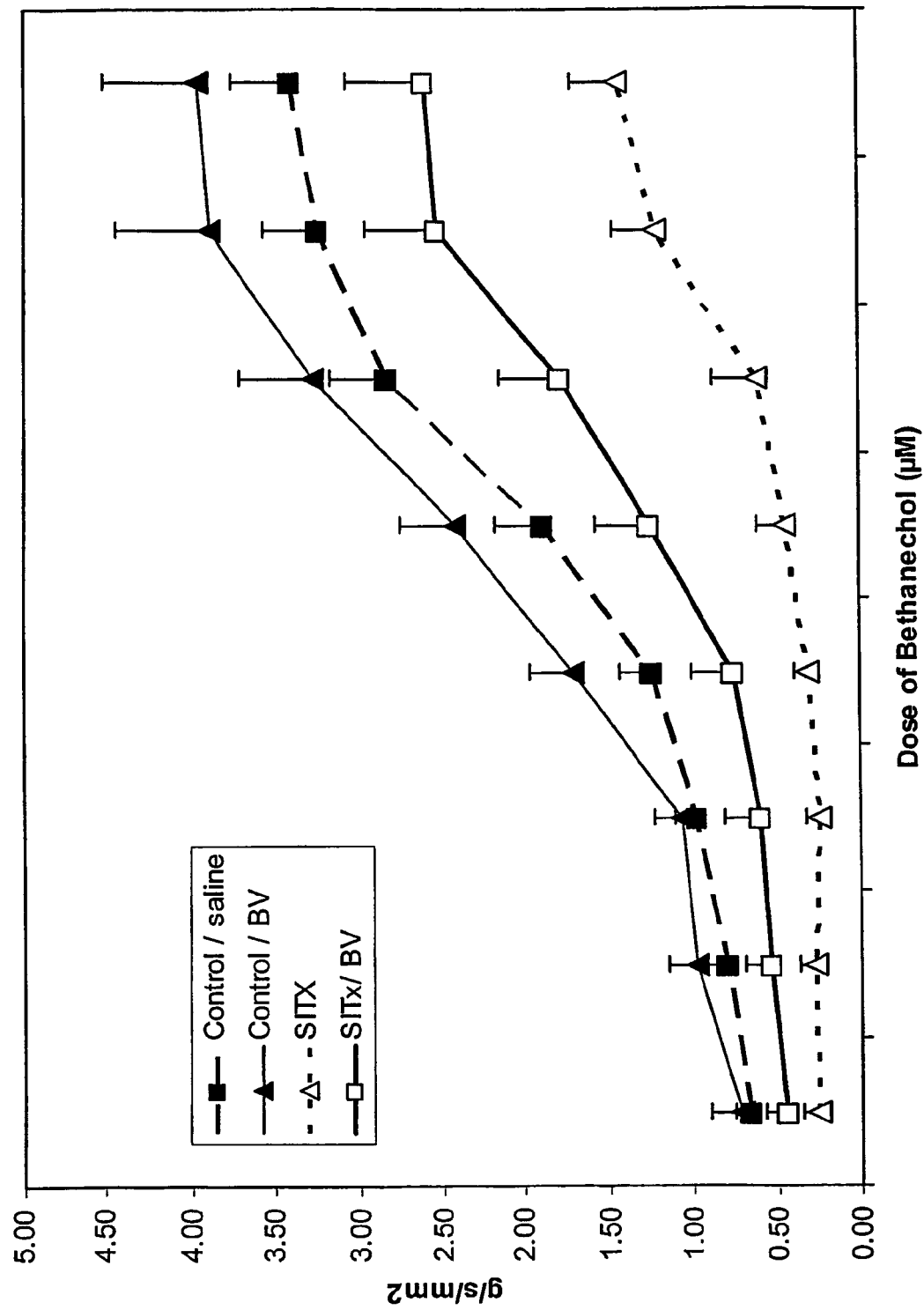
FIG. 25 is a line graph illustrating the effect of treatment with increasing doses of bethanechol on contractility response in transplanted small intestine. Jejunal circular muscle strips from control animals (filled triangles) and unoperated animals receiving BV treatment (filled squares) showed a dose-dependent increase in contractile area in response to bethanechol. This activity was significantly diminished in graft muscle taken 24 hours following transplantation (open triangles). Significant improvement was measured in transplanted animals treated with BV (open squares) (N=5 each).

The addition of bethanechol (0.3 to 300 μM) to the bathing superfusate elicited a concentration-dependent increase in circular muscle contractility. Control muscles from untreated and BV treated animals exhibited similar robust phasic and tonic contractions to bethanechol (100 μM), while muscles from the untreated transplanted intestine generated approximately 51% less contractility in response to bethanechol (1.7=0.4 g/mm2/s). However, bethanechol-stimulated muscle contractility generated by BV treated animals was significantly improved over the untreated graft muscles. These observations were reflected throughout the generation of the complete integrated contractile bethanechol dose-response curves for each of the four groups of animals. As shown in FIG. 25, BV therapy reduced the transplant-induced suppression in muscle contractility, restoring the muscle's response to pre-transplant levels.

Leukocyte Recruitment. Cellular inflammatory events in the small intestinal muscularis were characterized 24 hours after SITx. Myeloperoxidase (MPO) activity, as determined by Hanker-Yates histochemistry, was used to quantify the polymorphonuclear neutrophil (PMN) infiltrate in tissues from control and transplanted animals, with and without BV treatment. In unoperated controls with saline, MPO-positive cells were rare. BV injection into normal animals decreased MPO positive cells extravasation to 3.9±1.3 cells per ×200 field, but did not reach significance compared to saline controls. SITx resulted in a significant recruitment of PMNs into the intestinal muscularis. BV treatment significantly decreased the mean number of MPO positive cells.

Molecular Inflammatory Responses. Four hours following reperfusion, mRNA levels of various prototypical inflammatory mediators were determined by quantitative analysis.

Real time RT-PCR analysis revealed a significant increase in mRNA expression for the inflammation-related cytokines, IL-6, IL-10, TNFα and IL-1β in graft muscularis externa extracts 4 hours after reperfusion, when compared to unoperated saline-controls (FIG. 23A-D).

In graft muscularis extracts of recipient rats treated with BV, the mean-comparative expression of IL-6 and IL-1b expression was reduced on average by 24% (p=0.0099, N=5) and 30% (p=0.0040, N=5), respectively, compared to the saline-treated transplanted and reperfused graft at 4 hours (FIGS. 23A and 23D). However, unlike IL-6 and IL-1b, BV treatment did not significantly change the upregulation of TNF-α or IL-10 caused by transplantation (FIGS. 23B and 23C. BV treatment of unoperated animals also did not alter the basal mRNA expression of any of the cytokines.

Gene expression of inducible nitric oxide synthase (iNOS) and cyclooxygenase (COX-2) were quantified by real time RT-PCR. The results showed that both iNOS and COX-2, enzymes of the puissant smooth muscle inhibitors nitric oxide and prostanoids, were significantly upregulated in the muscularis of the transplanted grafts 70.4-fold and 5.2-fold, respectively (FIG. 24A-B). The mean relative mRNA expression of both enzymes was reduced by approximately 50% in BV treated rats (p=0.015 and p=0.032, N=5 each). BV treatment of unoperated control animals did not alter the mRNA expression of iNOS or COX-2. ICAM-1 gene expression, an adhesion molecule that plays an important role in the recruitment of circulating inflammatory cells into inflamed tissues, was also significantly increased 6.1±3.8-fold compared with controls. BV treatment significantly reduced ICAM-1 expression in the graft up to 30% (p=0.020) (FIG. 23C). BV treatment significantly reduced MnSOD expression in the graft as well (FIG. 23D).

HO-1 Induction During Intestinal I/R Injury. Since HO-1 regulates heme catalysis and BV production, exogenously provided BV may influence endogenous HO-1 induction in BV-treated recipients. In the normal intestine, HO-1 protein expression was absent. Ischemia/reperfusion injury was associated with a gradual increase of HO-1 expression in air-treated grafts, reaching maximum level between 6 and 24 hours following reperfusion. BV treatment did not have a significant effect on the intestinal HO-1 production.

SITx with 6 Hours Preservation (Severe Injury)

Figure 27:
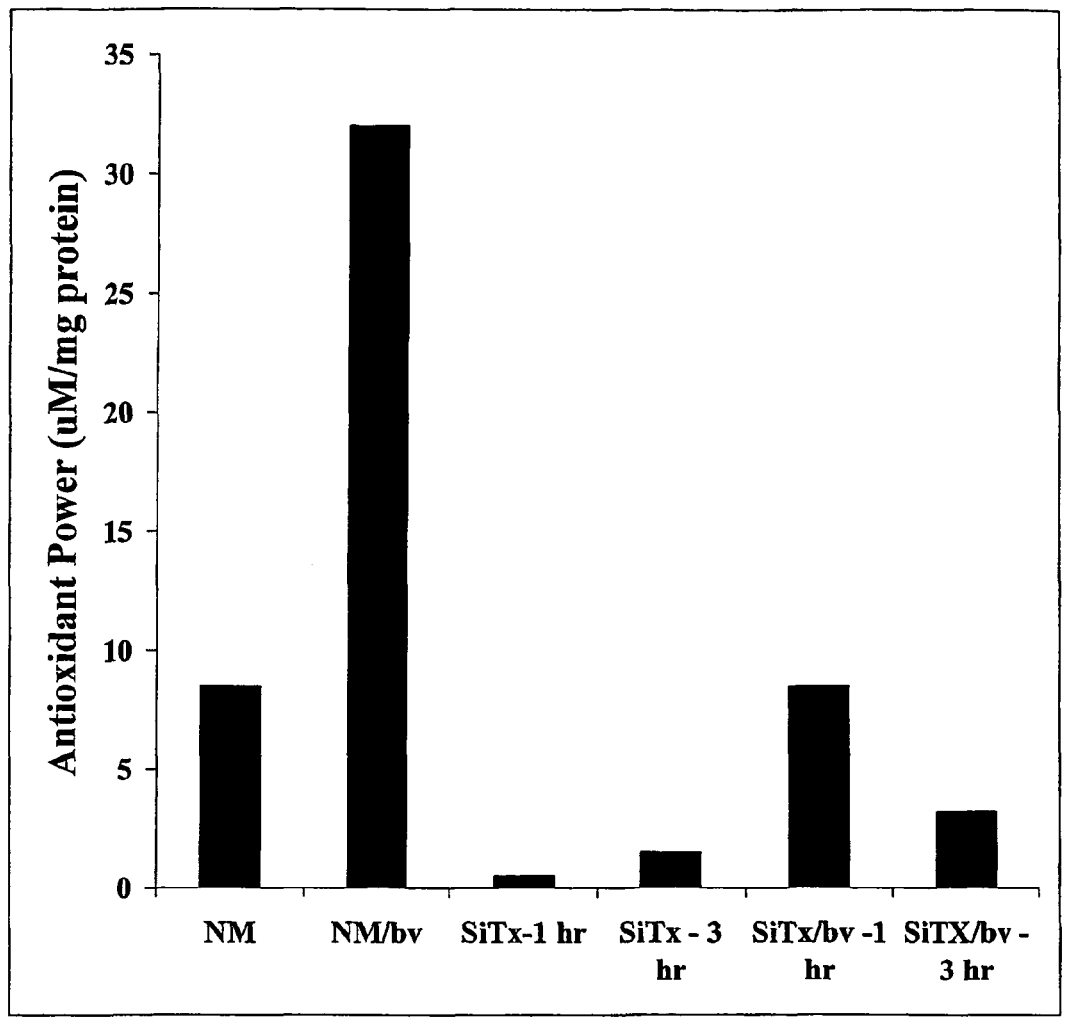
FIG. 27 is a line graph illustrating the effect of treatment with biliverdin on antioxidant capacity in a small intestine transplant model.

Antioxidant capacity after BV treatment. the total antioxidant capacity or antioxidant power within the graft specimens was quantitatively measured. Antioxidant levels in the graft were detected using Total Antioxidant Power® (Oxford Biomedical Research, Oxford, Mich.), according to the manufacturer's instructions. In this procedure, the evaluation of the antioxidant level in a sample is detected by evaluation of $Cu^+$ derived from $Cu^{++}$ by the combined action of all antioxidants present in the sample. As is shown in FIG. 27, BV treatment increased the antioxidant capacity of the transplanted intestine to normal levels.

Serum inflammatory mediators. The decreased expression of IL-6 and iNOS mRNA (FIGS. 23A and 24B) was also reflected in protein production after transplantation of cold-preserved grafts; saline and BV treated controls serum IL-6 concentrations were low. Transplantation caused a significant increase in serum IL-6 protein concentrations (5131.4±3169.1 pg/mL) 3 hours after engraftment and the serum IL-6 increase was significantly less in animals that had received BV therapy (1652±306.9 pg/mL, p=0.0347). Because of the importance of nitric oxide as a regulator of gastrointestinal motility, the molecular expression of iNOS was followed by measuring nitric oxide metabolites in the serum of the transplanted animals. In saline and BV treated controls, mean serum nitrite/nitrate (NO) levels were 17.3±7.4 and 18.4±3.2 µM, respectively. SITx resulted in a significant elevation of serum NO products to 34.4±15.2 µM 12 hours after engraftment. BV treatment significantly decreased transplantation-induced serum NO levels by 53% to 18.2±3.9 µM.

Figure 26B:
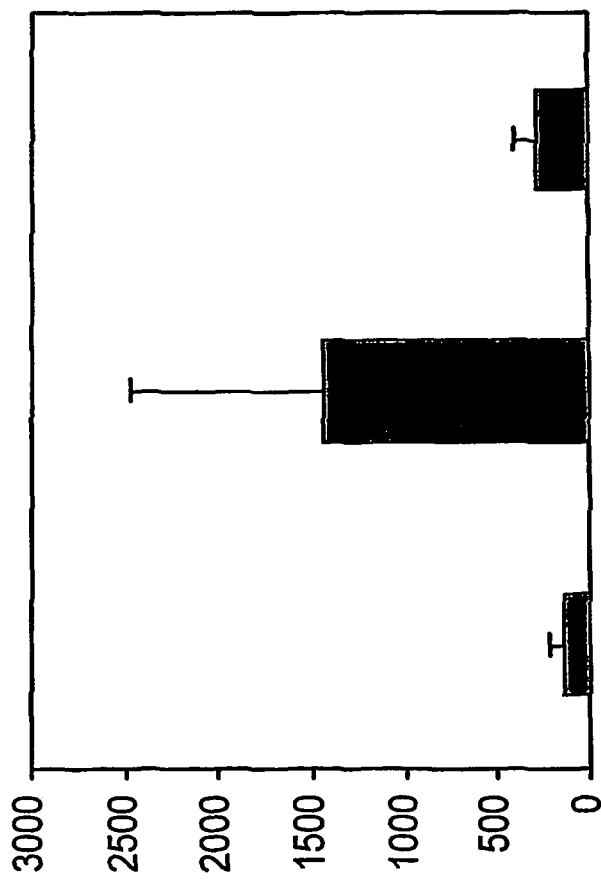
FIGS. 26A-26B are bar graphs illustrating the effect of treatment with biliverdin on permeability and blood flow, respectively, in a small intestine transplant model.
Figure 26A:
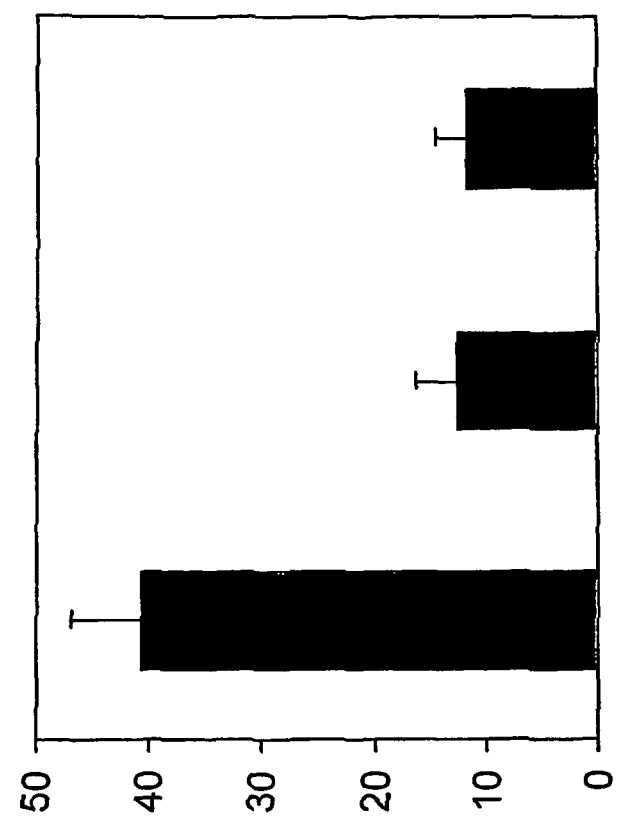

Graft permeability. Loss of intestinal barrier function causes increase of graft permeability. Graft permeability was determined by the everted gut sac method using 4 Kd Fluorescein isothiocyanate dextran. A striking increase in permeability was seen in untreated grafts (1.44±1.0 ml/cm/min). In BV treated grafts, there was a minimal increase of intestinal permeability, or about a 60% inhibition of the increase, to 2.82% 1.3 ml/cm/min (FIG. 26A).

Blood microcirculation. Blood flow following transplantation is dramatically decreased. Administration of BV had no effect on microvascular blood flow following transplantation (FIG. 26B).

Animal survival. Six hours of cold preservation in UW of the intestinal graft induced intestinal dysfunction in untreated recipients; 3 out of 14 control animals died within 24 hours and an additional 3 animals died 5 and 7 days after SITx due to bowel obstruction secondarily to intestinal I/R injury. In contrast, all BV-treated animals recovered smoothly from SITx. Overall animal survival for 14 days follow-up was 57.1% (8/14) in saline control and 100% (8/8) in BV-treated group (p<0.05).

Conclusions

The above data indicated that BV treatment results in the blunting of the proinflammatory responses within the graft intestinal muscularis following transplantation, enhancing small intestine graft function and recipient survival.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an inflammatory disorder in a patient in need thereof, wherein the method comprises
    administering to said patient a composition comprising a pharmaceutically acceptable carrier and at least one agent selected from the group consisting of: heme oxygenase-1 (HO-1), bilirubin, biliverdin, ferritin, iron, desferoxamine, salicylaldehyde isonicotinoyl hydrazone, iron dextran, and apoferritin, wherein the composition is administered in an amount sufficient to treat the inflammatory disorder; and wherein the inflammatory disorder is localized in the gastrointestinal tract and is selected from the group consisting of: amoebic dysentery, bacillary dysentery, schistosomiasis, *campylobacter* enterocolitis, *yersinia* enterocolitis, *enterobius vermicularis*, radiation enterocolitis, ischaemic colitis, eosinophilic gastroenteritis, ulcerative colitis, indeterminate colitis, and Crohn's disease.

2. The method of claim 1, wherein the composition comprises ferritin.

3. The method of claim 1, wherein the composition comprises biliverdin.

4. The method of claim 3, wherein biliverdin is administered to the patient at a dosage of about 1 to 1000 micromoles/kg/day.

5. The method of claim 1, wherein the inflammatory disorder is ulcerative colitis.

6. The method of claim 1, wherein the composition comprises bilirubin.

7. The method of claim 1, wherein the composition comprises ferritin.

8. The method of claim 1, wherein the composition comprises at least one of desferoxamine (DFO) or salicylaldehyde isonicotinoyl hydrazone (SIH).

9. The method of claim 1, wherein the composition comprises iron dextran.

10. The method of claim 1, wherein the composition comprises apoferritin.

11. The method of claim 2, wherein the composition comprises iron.

12. The method of claim 1, wherein the inflammatory disorder is ulcerative colitis.

13. The method of claim 1, further comprising the step of administering a pharmaceutical composition comprising carbon monoxide to the patient.

14. The method of claim 1, wherein the method comprises administering at least two of the agents.

15. The method of claim 1, wherein the at least one agent is administered orally.

16. A method of treating an inflammatory disorder in a patient in need thereof, wherein the method comprises
    administering to said patient a composition comprising a pharmaceutically acceptable carrier and at least one agent selected from the group consisting of: heme oxygenase-1 (HO-1), bilirubin, biliverdin, ferritin, iron, desferoxamine, salicylaldehyde isonicotinoyl hydrazone, iron dextran, and apoferritin, wherein the composition is administered in an amount sufficient to treat the inflammatory disorder, and wherein the inflammatory disorder is characterized by free radical damage.

17. The method of claim 16, wherein the composition comprises ferritin.

18. The method of claim 16, wherein the composition comprises biliverdin.

19. The method of claim 16, wherein biliverdin is administered to the patient at a dosage of about 1 to 1000 micromoles/kg/day.

20. The method of claim 16, wherein the inflammatory disorder is ulcerative colitis.

21. The method of claim 16, wherein the composition comprises bilirubin.

22. The method of claim 16, wherein the composition comprises ferritin.

23. The method of claim 16, wherein the composition comprises at least one of desferoxamine (DFO) or salicylaldehyde isonicotinoyl hydrazone (SIH).

24. The method of claim 16, wherein the composition comprises iron dextran.

25. The method of claim 16, wherein the composition comprises apoferritin.

26. The method of claim 16, wherein the composition comprises iron.

27. The method of claim 16, wherein the inflammatory disorder is selected from the group consisting of: amoebic dysentery, bacillary dysentery, schistosomiasis, *campylobacter* enterocolitis, *yersinia* enterocolitis, *enterobius vermicularis*, radiation enterocolitis, ischaemic colitis, eosinophilic gastroenteritis, ulcerative colitis, indeterminate colitis, and Crohn's disease.

28. The method of claim 27, wherein the inflammatory disorder is ulcerative colitis.

29. The method of claim 16, further comprising the step of administering a pharmaceutical composition comprising carbon monoxide to the patient.

30. The method of claim 16, wherein the method comprises administering at least two of the agents.

31. The method of claim 16, wherein the at least one agent is administered orally.

* * * * *